United States Patent
Martin et al.

(10) Patent No.: US 9,427,226 B2
(45) Date of Patent: Aug. 30, 2016

(54) LAPAROSCOPIC SUTURING INSTRUMENT WITH RACK DRIVE

(75) Inventors: David T. Martin, Milford, OH (US); Robert Brik, Brookline, MA (US); Benjamin D. Dickerson, Cincinnati, OH (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 1127 days.

(21) Appl. No.: 13/419,535

(22) Filed: Mar. 14, 2012

(65) Prior Publication Data
US 2013/0245648 A1    Sep. 19, 2013

(51) Int. Cl.
| A61B 17/06 | (2006.01) |
| A61B 17/04 | (2006.01) |
| A61B 17/00 | (2006.01) |
| A61B 17/29 | (2006.01) |

(52) U.S. Cl.
CPC ....... *A61B 17/0469* (2013.01); *A61B 17/0482* (2013.01); *A61B 2017/00398* (2013.01); *A61B 2017/06052* (2013.01); *A61B 2017/2913* (2013.01); *A61B 2017/2923* (2013.01); *A61B 2017/2936* (2013.01)

(58) Field of Classification Search
CPC .................. A61B 17/0469; A61B 2017/0472; A61B 2017/047; A61B 17/0482; A61B 17/0483
USPC ......................................... 606/139, 144–147
See application file for complete search history.

(56) References Cited

U.S. PATENT DOCUMENTS

| 4,935,027 A | * | 6/1990 | Yoon ............................ 606/146 |
| 5,797,927 A | * | 8/1998 | Yoon ............................ 606/144 |
| 5,993,466 A | * | 11/1999 | Yoon .................... A61B 17/062 606/144 |
| 5,993,467 A | * | 11/1999 | Yoon ............................ 606/147 |
| 6,056,771 A | | 5/2000 | Proto |
| 6,071,289 A | | 6/2000 | Stefanchik et al. |
| 6,086,601 A | * | 7/2000 | Yoon ............................ 606/148 |
| 6,126,665 A | * | 10/2000 | Yoon ............................ 606/144 |
| 6,159,224 A | * | 12/2000 | Yoon ............................ 606/147 |
| 6,783,524 B2 | * | 8/2004 | Anderson ...... A61B 17/320068 606/1 |

(Continued)

FOREIGN PATENT DOCUMENTS

| WO | WO 98/57585 | 12/1998 |
| WO | WO 2012/007941 | 1/2012 |

OTHER PUBLICATIONS

International Search Report dated Jun. 26, 2013 for PCT/US2013/03045.

(Continued)

*Primary Examiner* — Katrina Stransky
(74) *Attorney, Agent, or Firm* — Frist Brown Todd LLC

(57) ABSTRACT

A suture needle driving instrument comprises a shaft, an end effector, and a handle assembly. The end effector is located at the distal end of the shaft and includes a pair of grasping arms having a respective pair of jaws driven by a respective drive shaft. Each pair of jaws is operable to cooperate to grasp and release a suture needle. The handle assembly includes a control assembly that is operable to rotate the drive shafts to transfer the suture needle between the grasping arms. In some versions, the control assembly may include an actuatable rack. The rack may include one or more control features that selectively rotate the drive shafts as the rack is actuated. The rack may further include cam surfaces to selectively restrict the motion of the drive shafts as the rack is actuated. In some versions the rack may actuate vertically.

18 Claims, 39 Drawing Sheets

(56) References Cited

U.S. PATENT DOCUMENTS

| | | | |
|---|---|---|---|
| 6,866,671 B2* | 3/2005 | Tierney | A61B 19/2203 606/1 |
| 7,628,796 B2 | 12/2009 | Shelton, IV et al. | |
| 7,775,972 B2* | 8/2010 | Brock | A61B 17/0469 606/144 |
| 2007/0060931 A1* | 3/2007 | Hamilton | A61B 17/062 606/144 |
| 2008/0051631 A1* | 2/2008 | Dejima et al. | 600/114 |
| 2008/0228204 A1* | 9/2008 | Hamilton | A61B 17/0491 606/148 |
| 2010/0030238 A1* | 2/2010 | Viola | A61B 17/04 606/144 |
| 2010/0100125 A1 | 4/2010 | Mahadevan | |
| 2011/0313433 A1* | 12/2011 | Woodard et al. | 606/145 |
| 2012/0150199 A1* | 6/2012 | Woodard, Jr. | A61B 17/0469 606/147 |
| 2013/0178854 A1* | 7/2013 | Sholev et al. | 606/79 |

OTHER PUBLICATIONS

U.S. Appl. No. 13/295,186, filed Nov. 14, 2011, Woodard, Jr. et al.
U.S. Appl. No. 13/295,203, filed Nov. 14, 2011, Woodard, Jr. et al.
U.S. Appl. No. 13/295,210, filed Nov. 14, 2011, Woodard, Jr. et al.
U.S. Appl. No. 61/355,832, filed Jun. 17, 2010, Woodard, Jr.
U.S. Appl. No. 61/413,680, filed Nov. 15, 2010, Woodard, Jr.
International Preliminary Report on Patentability dated Sep. 16, 2014 for Application No. PCT/US2013/030345, 7 pages.

* cited by examiner

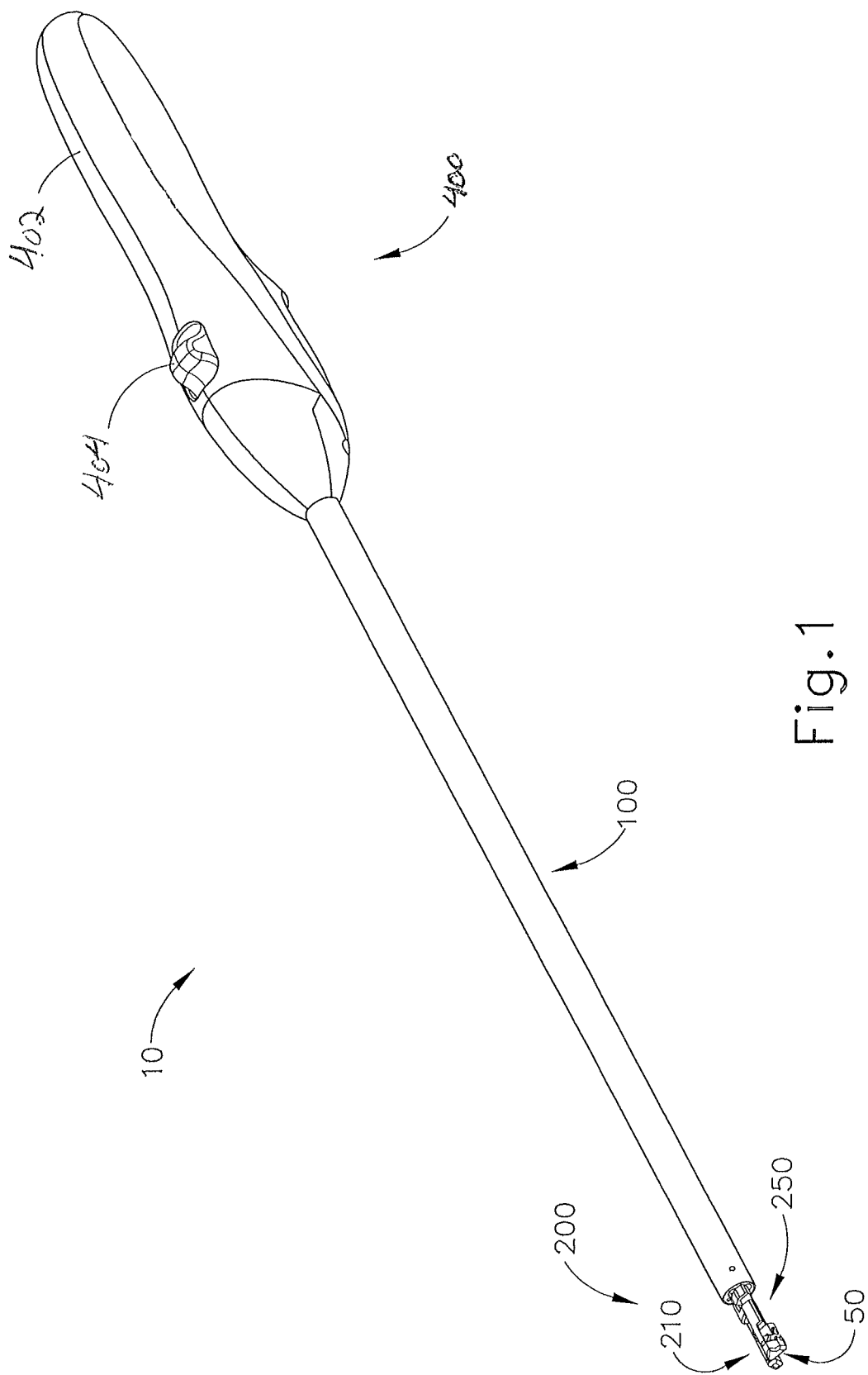

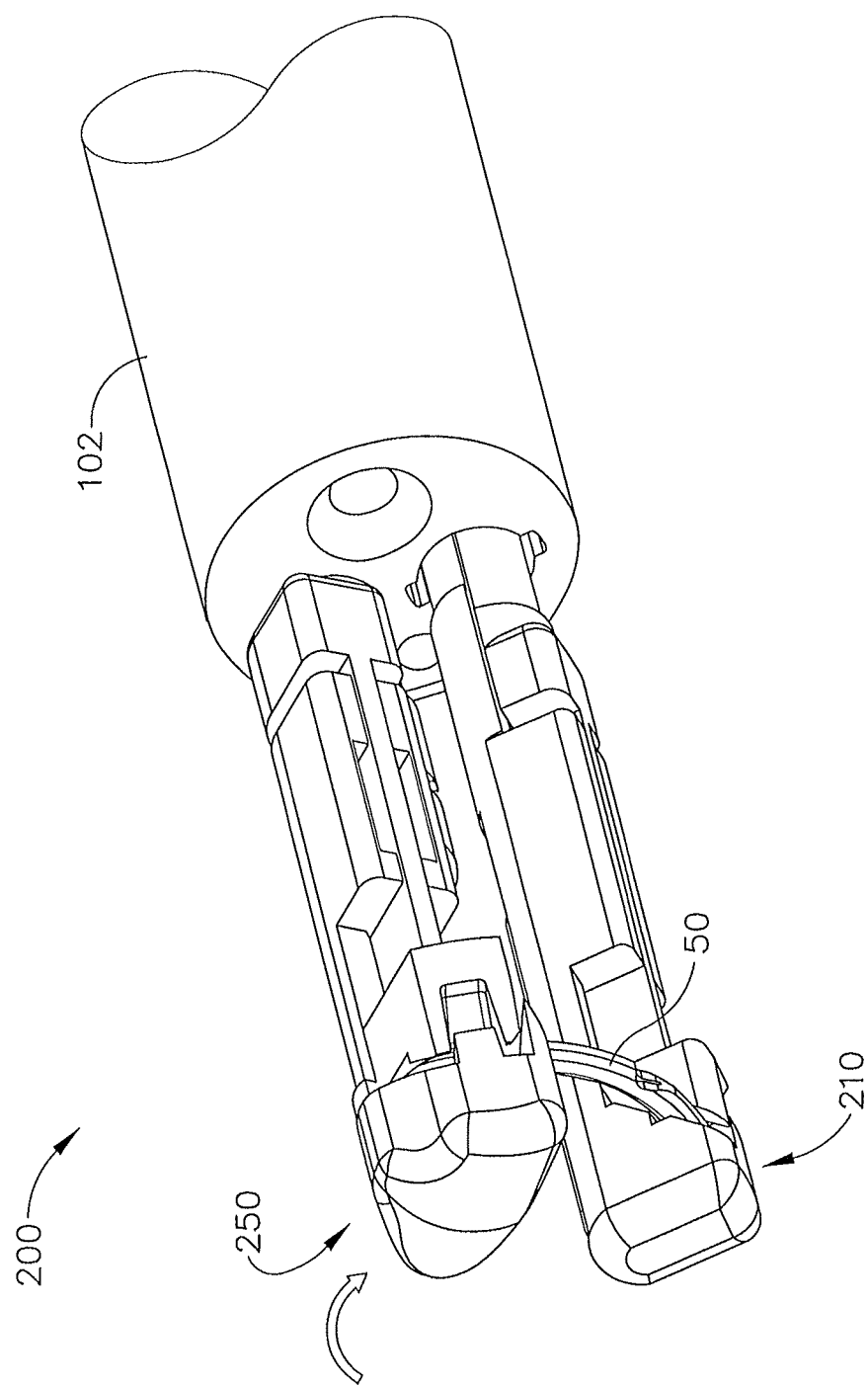

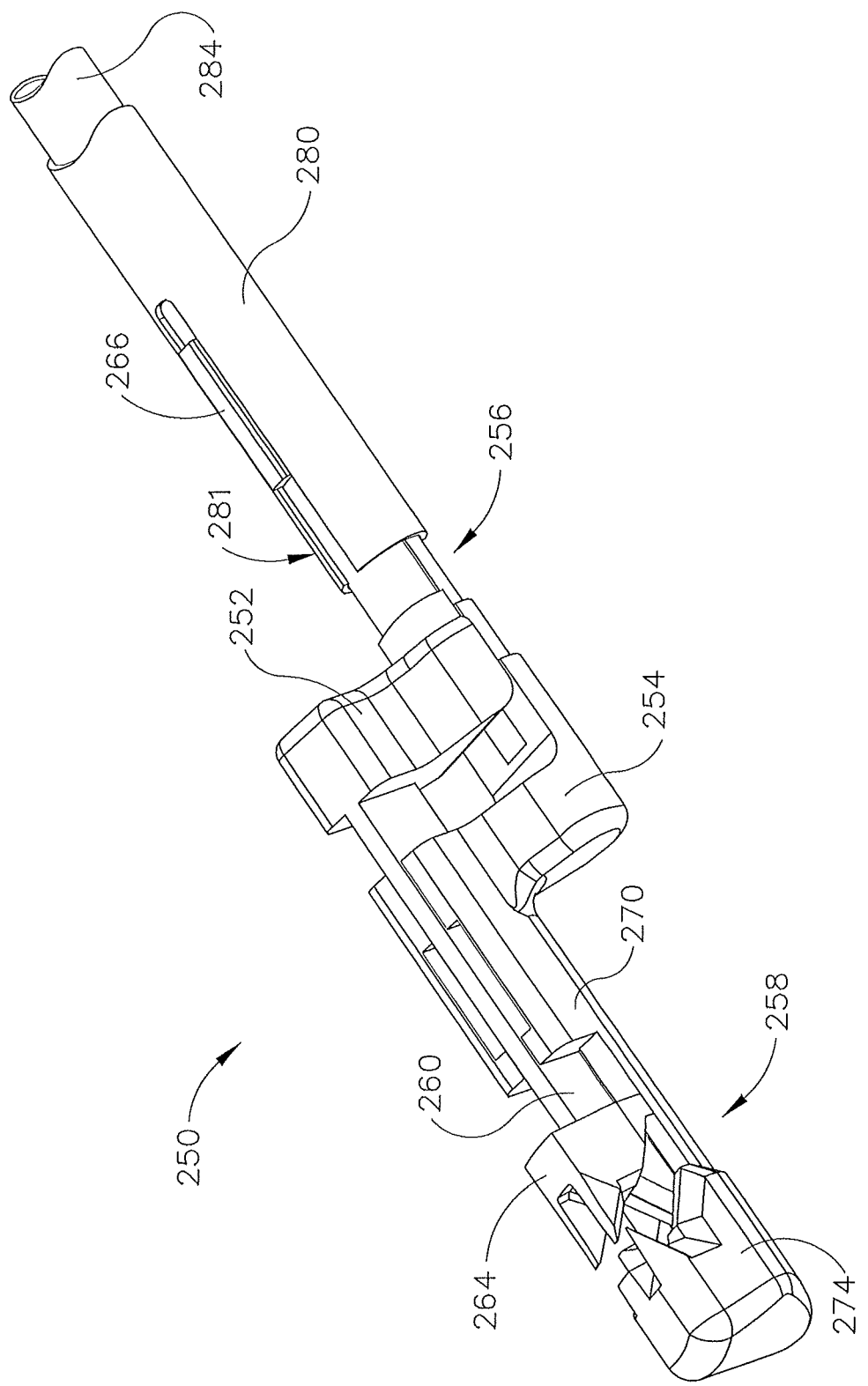

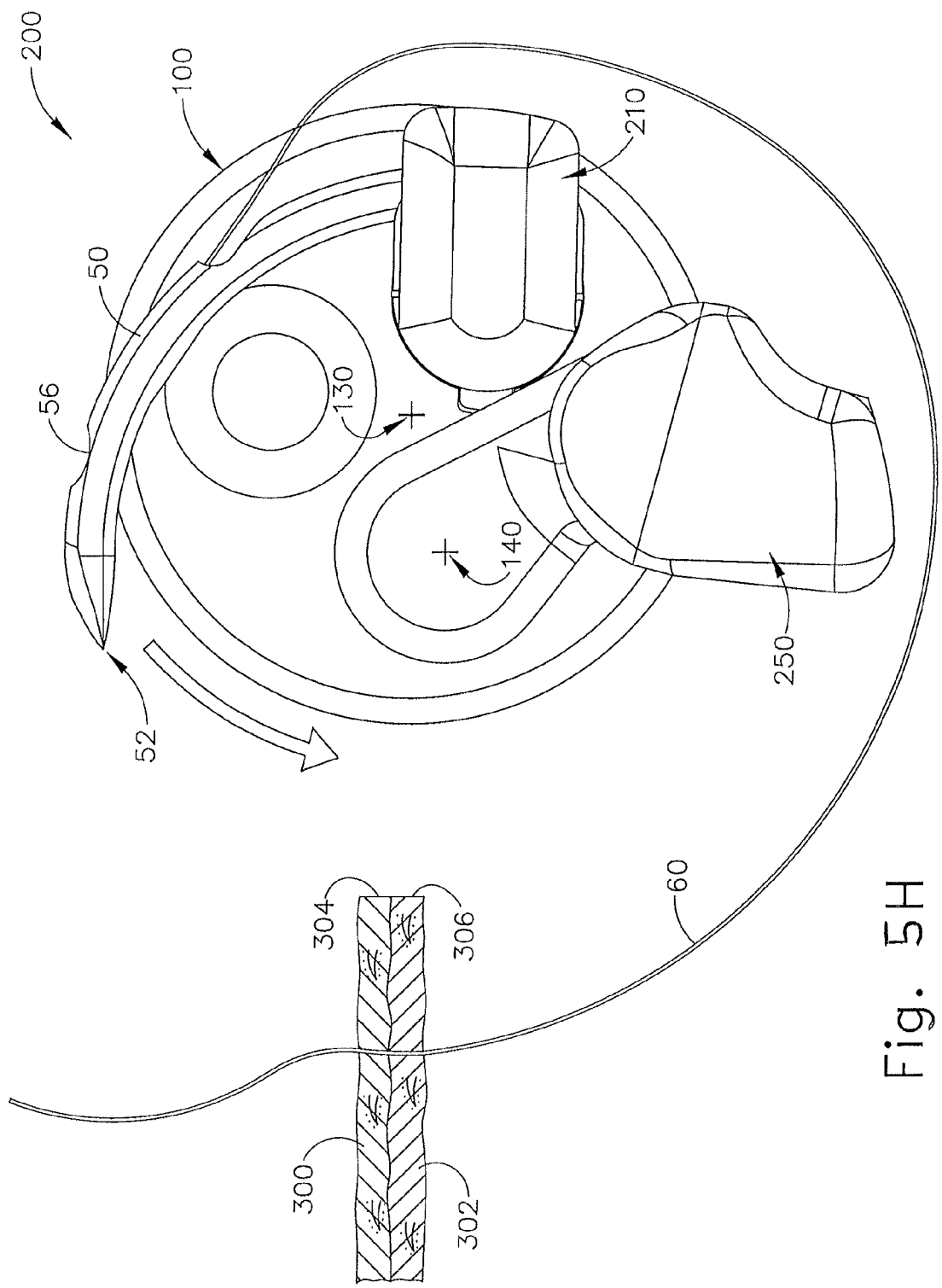

LAPAROSCOPIC SUTURING INSTRUMENT WITH RACK DRIVE

BACKGROUND

In some settings it may be desirable to perform a surgical procedure in a minimally invasive manner, such as through a trocar or other type of access cannula. Examples of trocars include the various ENDOPATH® EXCEL™ products by Ethicon Endo-Surgery, Inc. of Cincinnati, Ohio. Such trocars may present different inner diameters, such as those ranging from approximately 4.7 mm to approximately 12.9 mm, allowing a surgeon to choose a particular trocar based on a balance of considerations such as access needs and incision size. In some minimally invasive surgical procedures, at least two trocars may be inserted through the abdominal wall of the patient. An imaging device such as an endoscope may be inserted through one of the trocars to provide visualization of the surgical site. A surgical instrument may be inserted through another one of the trocars to perform surgery at the site. In procedures performed within the abdominal cavity, the cavity may be insufflated with pressurized carbon dioxide to provide more room for visualization and manipulation of instruments. In some settings, additional trocars may be used to provide access for additional surgical instruments. Minimally invasive surgery may also be performed through access portals such as the Single Site Laparoscopy Access System by Ethicon Endo-Surgery, Inc. of Cincinnati, Ohio, which provides ports for more than one surgical instrument through a single incision in a patient.

It may also be desirable to use sutures during some minimally invasive surgical procedures, such as to close an opening, to secure two layers of tissue together, to provide an anastomosis, etc. Such use of sutures may be in addition to or in lieu of using other devices and techniques such as clips, staples, electrosurgical sealing, etc. Performing suturing through trocars or other minimally invasive access ports may be more difficult than suturing in an open surgical procedure. For instance, manipulating a needle and suture with conventional tissue graspers through trocars may be relatively difficult for many surgeons. Thus, improved laparascopic surgical instruments may make suturing procedures performed through trocars relatively easier. Examples of surgical instruments configured to facilitate suturing through trocars include the LAPRA-TY® Suture Clip Applier, the Suture Assistant, and the ENDOPATH® Needle Holder, all of which are by Ethicon Endo-Surgery, Inc. of Cincinnati, Ohio. Additional suturing instruments are disclosed in U.S. Pat. No. 7,628,796, entitled "Surgical Suturing Apparatus with Anti-Backup System," issued Dec. 8, 2009, the disclosure of which is incorporated by reference herein; U.S. Pat. No. 6,071,289, entitled "Surgical Device for Suturing Tissue," issued Jun. 6, 2000, the disclosure of which is incorporated by reference herein; U.S. patent application Ser. No. 13/295,203, entitled "Laparoscopic Suturing Instrument with Dual-Action Needle Graspers," filed Nov. 11, 2011, now U.S. Pat. No. 8,702,732, issued Apr. 22, 2014, the disclosure of which is incorporated by reference herein; U.S. patent application Ser. No. 13/295,210, entitled "Laparoscopic Suturing Instrument with Perpendicular Eccentric Needle Motion," filed Nov. 11, 2011, now U.S. Pat. No. 8,906,043, issued Dec. 19, 2014, the disclosure of which is incorporated by reference herein; and U.S. Provisional Patent Application No. 61/355,832, entitled "Laparoscopic Suture Device," filed Jun. 17, 2010, the disclosure of which is incorporated by reference herein.

Exemplary suturing needles are disclosed in U.S. Pat. No. 6,056,771, entitled "Radiused Tip Surgical Needles and Surgical Incision Members," issued May 2, 2000, the disclosure of which is incorporated by reference herein; U.S. Pub. No. 2010/0100125, entitled "Suture Needle and Suture Assembly," published Apr. 22, 2010, the disclosure of which is incorporated by reference herein; U.S. Provisional Application Ser. No. 61/413,680, filed Nov. 15, 2010, entitled "Custom Needle for Suture Instrument," the disclosure of which is incorporated by reference herein; and U.S. patent application Ser. No. 13/295,186, entitled "Needle for Laparoscopic Suturing Instrument," filed on Nov. 14, 2011, now U.S. Pat. No. 9,125,646, issued Sep. 8, 2015, the disclosure of which is incorporated by reference herein.

While a variety of devices and methods have been made and used for suturing tissue, it is believed that no one prior to the inventor(s) has made or used the technology described herein.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 1 depicts a perspective view of an exemplary laparoscopic suturing instrument;

FIG. 2B depicts a perspective view of the end effector and needle of FIG. 2A, in a second operational configuration;

FIG. 4A depicts a first partial perspective view of a second needle grasping arm of the end effector of FIG. 2A

FIG. 5H depicts an end elevation view of the end effector and needle of FIG. 2A, during an exemplary eighth stage of operation;

Figure 2A:
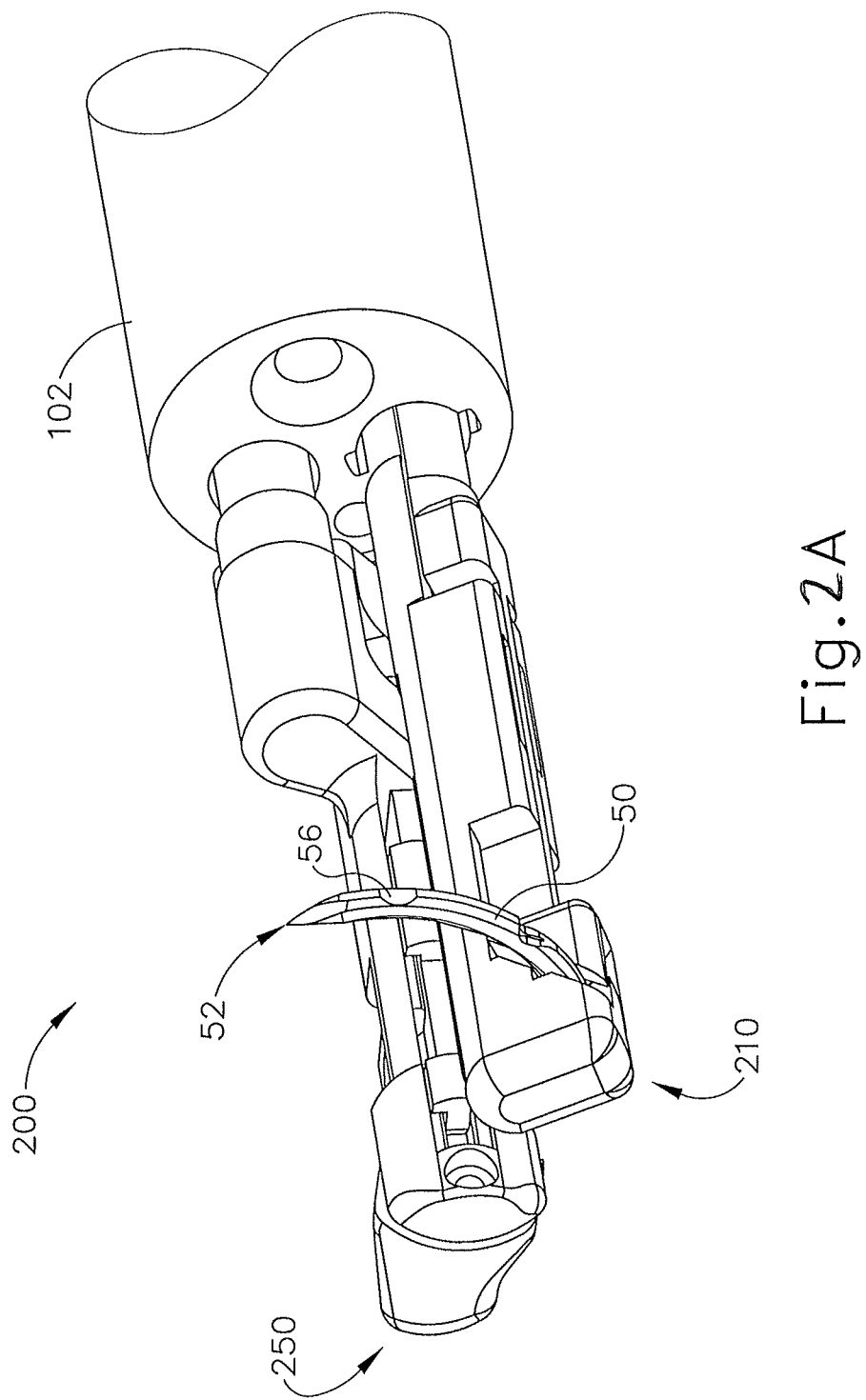
FIG. 2A depicts a perspective view of the end effector of the suturing instrument of FIG. 1 with a needle in a first operational configuration.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It should therefore be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview

FIG. 1 shows an exemplary laparoscopic suturing instrument (10). Instrument (10) of this example includes an exemplary handle portion (400), a shaft (100) extending distally from handle portion (400), and an end effector (200) at the distal end of shaft (100). Handle portion (400) of the present example includes a grip (402) and a toggle (404), though these are merely exemplary. By way of example only, handle portion (400) may be constructed in accordance with at least some of the teachings of U.S. Provisional Patent Application No. 61/355,832, the disclosure of which is incorporated by reference herein; and/or in accordance with at least some of the teachings of U.S. Pat. Pub. No. 2011/0313433, entitled "Laparoscopic Suture Device with Asynchronous In-Line Needle Movement," published Dec. 22, 2011, now U.S. Pat. No. 9,168,037, issued Oct. 27, 2015, the disclosure of which is incorporated by reference herein.

Shaft (100) of the present example has an outer diameter sized to permit shaft (100) to be inserted through a conventional trocar (not shown). Shaft (100) also has a length sized to permit end effector (200) to be positioned at a surgical site within a patient while also allowing handle portion (400) to be manipulated by a user (e.g., a surgeon) from a location outside the patient when shaft (100) is disposed in a trocar. Of course, shaft (100) need not necessarily be dimensioned for use through a trocar. For instance, instrument (10) may be used and/or configured for use in open surgical procedures.

In some versions, shaft (100) includes one or more articulating features, allowing end effector (200) to be articulated to various angles and positions relative to a longitudinal axis (130) (shown in FIGS. 5A-5H) defined by shaft (100). Merely illustrative examples of such articulation are taught in U.S. Provisional Application Ser. No. 61/355, 832, the disclosure of which is incorporated by reference herein. Various other suitable ways in which articulation may be provided will be apparent to those of ordinary skill in the art in view of the teachings herein. In addition or in the alternative, shaft (100) may be rotatable about longitudinal axis (130), relative to handle portion (400), to selectively position end effector (200) at various angular orientations about longitudinal axis (130). Of course, a user may rotate the entire instrument (10) about longitudinal axis (130) to selectively position end effector (200) at various angular orientations about longitudinal axis (130).

End effector (200) of the present example includes a first grasping arm (210) and a second grasping arm (250). As will be described in greater detail below, arms (210, 250) are configured to alternatingly throw and catch a curved suturing needle (50) along a path/plane that is substantially perpendicular to longitudinal axis (130) defined by shaft (100). Alternatively, arms (210, 250) may be configured to alternatingly throw and catch needle (50) along a path that is substantially parallel to longitudinal axis (130) defined by shaft (100); or along some other path.

In some versions, arms (210, 250) pass needle (50) back and forth from arm (210) to arm (250) and from arm (250) to arm (210) in an oscillating motion (i.e., back and forth in opposite directions), such that needle (50) does not traverse a circular path as needle (50) is being passed between arms (210, 250). Such action of needle (50) may be referred to as a "reverse reset." In some other versions, needle (50) may be passed between arms (210, 250) along a circular path in a single direction. Such action of needle (50) may be referred to as a "forward reset." By way of example only, arms (210, 250) may move in accordance with at least some of the teachings of U.S. Provisional Patent Application No. 61/355,832, the disclosure of which is incorporated by reference herein; and/or in accordance with at least some of the teachings of U.S. Pat. Pub. No. 2011/0313433, entitled "Laparoscopic Suture Device with Asynchronous In-Line Needle Movement," published Dec. 22, 2011, now U.S. Pat. No. 9,168,037, the disclosure of which is incorporated by reference herein. Regardless of whether arms (210, 250) move synchronously or asynchronously, arms (210, 250) may be configured to grip and/or compress tissue that is positioned between arms (210, 250) when arms are in approximated positions, which may facilitate passage of needle (50) through the tissue.

Needle (50) of the present example includes a sharp tip (52) (shown in FIG. 2A), a blunt end (54) (shown in FIG. 2C), and a pair of grasping regions (56, 58) (shown in FIGS. 2A, 2C) configured for grasping by arms (210, 250). In particular, grasping regions (56, 58) comprise scallops in the present example, though it should be understood that grasping regions (56, 58) may have various other configurations. A suture (60) (shown in FIGS. 5A-5H) is secured to a mid-region of needle (50). The configuration and relationship of suture (60) and needle (50) provides an exit of suture (60) from needle (50) at an angle that is generally tangent to or oblique relative to the curvature of needle (50). Such an angle may provide reduced drag forces and/or reduced tissue trauma as compared to drag forces and/or tissue trauma that might otherwise be encountered using a needle with a suture that exits at a generally perpendicular angle.

While the example described below includes just a single strand of suture (60) extending from needle (50), it should be understood that two or more strands (60) may extend from needle (50) (e.g., double leg suture, etc.). As yet another merely illustrative example, suture (60) may be secured to blunt end (54) of needle (50) instead of being secured to a mid-region of needle (50). In still other versions, end (54) includes a sharp tip instead of being blunt. It should also be understood that needle (50) may be straight instead of curved in some versions. By way of example only, needle (50) may be constructed in accordance with at least some of the teachings of U.S. Provisional Application Ser. No. 61/413,680; U.S. patent application Ser. No. 13/295,186, entitled "Needle for Laparoscopic Suturing Instrument," filed Nov. 14, 2011, now U.S. Pat. No. 9,125,646; U.S. Pat. No. 6,056,771, entitled "Radiused Tip Surgical Needles and Surgical Incision Members," issued May 2, 2000; and/or U.S. Pat. Pub. No. 2010/0100125, entitled "Suture Needle and Suture Assembly," published Apr. 22, 2010, the disclosures of which are incorporated by reference herein. Still other suitable configurations for needle (50) will be apparent to those of ordinary skill in the art in view of the teachings herein.

It should also be understood that needle (50) may be constructed using various techniques. By way of example only, needle (50) may be constructed using metal-injection-molding (MIM) processes. Needle (50) may also be formed from a sheet, wire, tube, extrusion, or other components that are bent, stamped, coined, milled, otherwise machined, and/or otherwise formed. Other suitable ways in which needle (50) may be constructed will be apparent to those of ordinary skill in the art in view of the teachings herein.

II. Exemplary End Effector

As noted above, end effector (200) comprises a pair of grasping arms (210, 250) that are operable to selectively grasp needle (50) during a suturing procedure. Grasping arms (210, 250) are exposed relative to an endcap (102) of shaft (100), shown in FIGS. 2A-2C. Each grasping arm (210, 250) extends along a respective axis that is parallel to yet offset from longitudinal axis (130) of shaft (100), shown in FIGS. 5A-5H. First grasping arm (210) maintains a fixed rotational position relative to shaft (100) during operation of instrument (10) in the present example. In some other versions, first grasping arm (210) is rotatable about its own longitudinal axis, relative to shaft (100). Second grasping arm (250) of the present example is rotatable about its longitudinal axis (140). Such motion can be seen in the series shown by FIGS. 2A-2C.

Figure 2C:
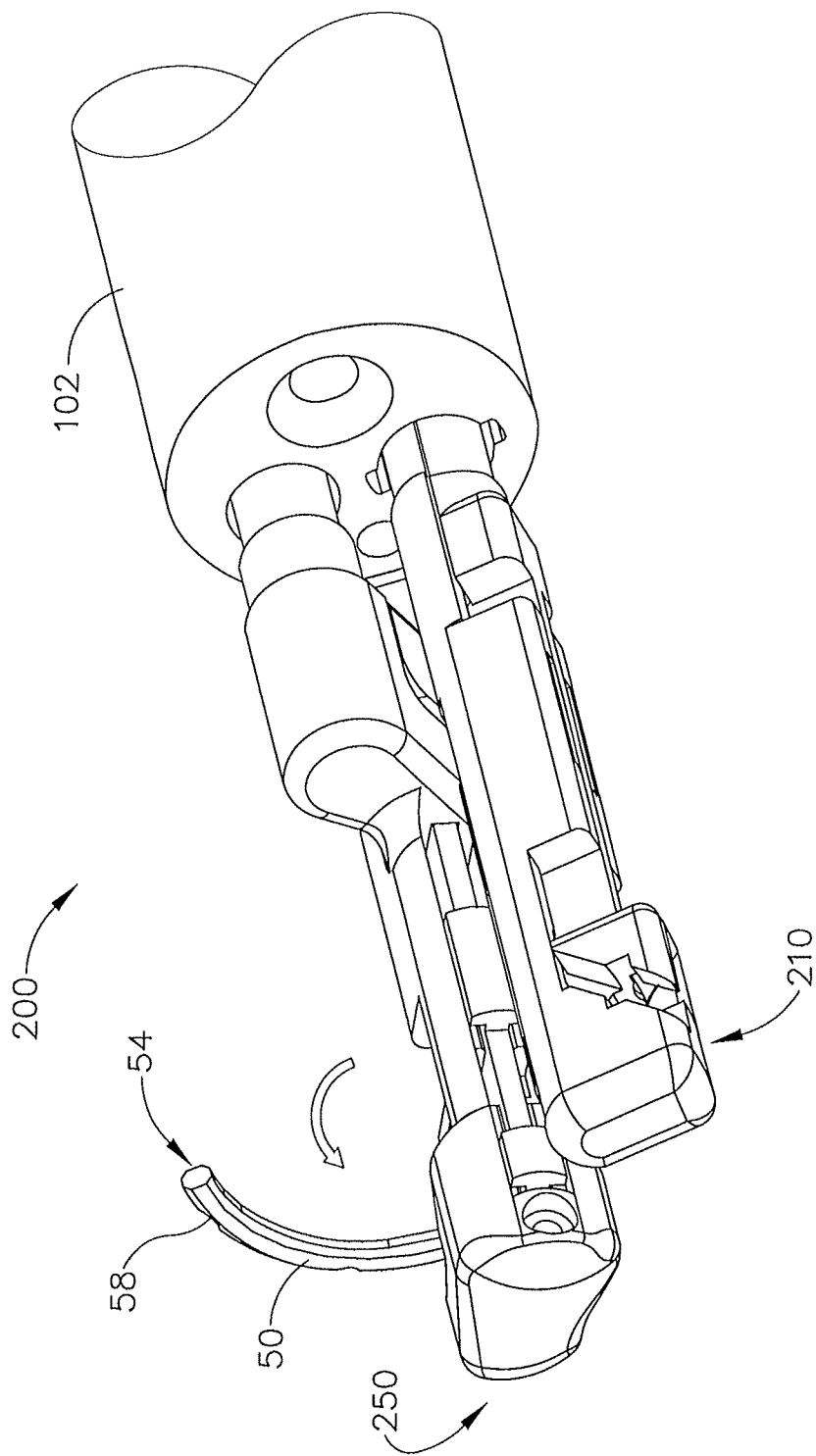
FIG. 2C depicts a perspective view of the end effector and needle of FIG. 2A, in a third operational configuration.

FIG. 2A shows first grasping arm (210) grasping needle (50), with second grasping arm (250) rotated away from needle (50), exposing sharp tip (52) of needle (50). FIG. 2B shows second grasping arm (250) rotated toward needle (50) to a position enabling second grasping arm (250) to grasp needle (50) and first grasping arm (210) to release needle (50). FIG. 2C shows second grasping arm (250) rotated away from first grasping arm (210), pulling needle (50) away from second grasping arm (250). After reaching this position, second grasping arm (250) may be rotated back to the position shown in FIG. 2B, to thereby pass needle (50) back to first grasping arm (210); then rotated back to the position shown in FIG. 2A to start the cycle over again.

In the examples described herein, needle (50) is driven along a plane that is substantially perpendicular to longitudinal axis (130) of shaft (100). In some other examples, needle (50) is driven along a plane that is oblique relative to longitudinal axis (130) of shaft (100) or substantially parallel to longitudinal axis (130) of shaft (100). During some uses of instrument (10), needle (50) may deviate from the desired perpendicular plane. Such deviation may be due to manufacturing tolerances, deflections caused by tissue or other structures, and/or for other reasons. Such deviation may be accentuated by using a needle (50) having a relatively great length. As will be described below, end effector (200) of the present example is configured to readily accommodate and correct such off-plane deviations. In other words, arms (210, 250) are operable to grasp needle (50) even in instances where needle (50) has deviated away from the expected perpendicular plane of motion; and arms (210, 250) are further operable to redirect a deviated needle (50) back onto the expected perpendicular plane of motion.

It should be noted that suture (60) is omitted from FIGS. 2A-2C for clarity. Various components of grasping arms (210, 250) will be described in greater detail below. Various ways in which grasping arms (210, 250) may be used will also be described in greater detail below. Other suitable components of and uses for grasping arms (210, 250) will be apparent to those of ordinary skill in the art in view of the teachings herein.

A. Exemplary First Grasping Arm

Figure 3A:
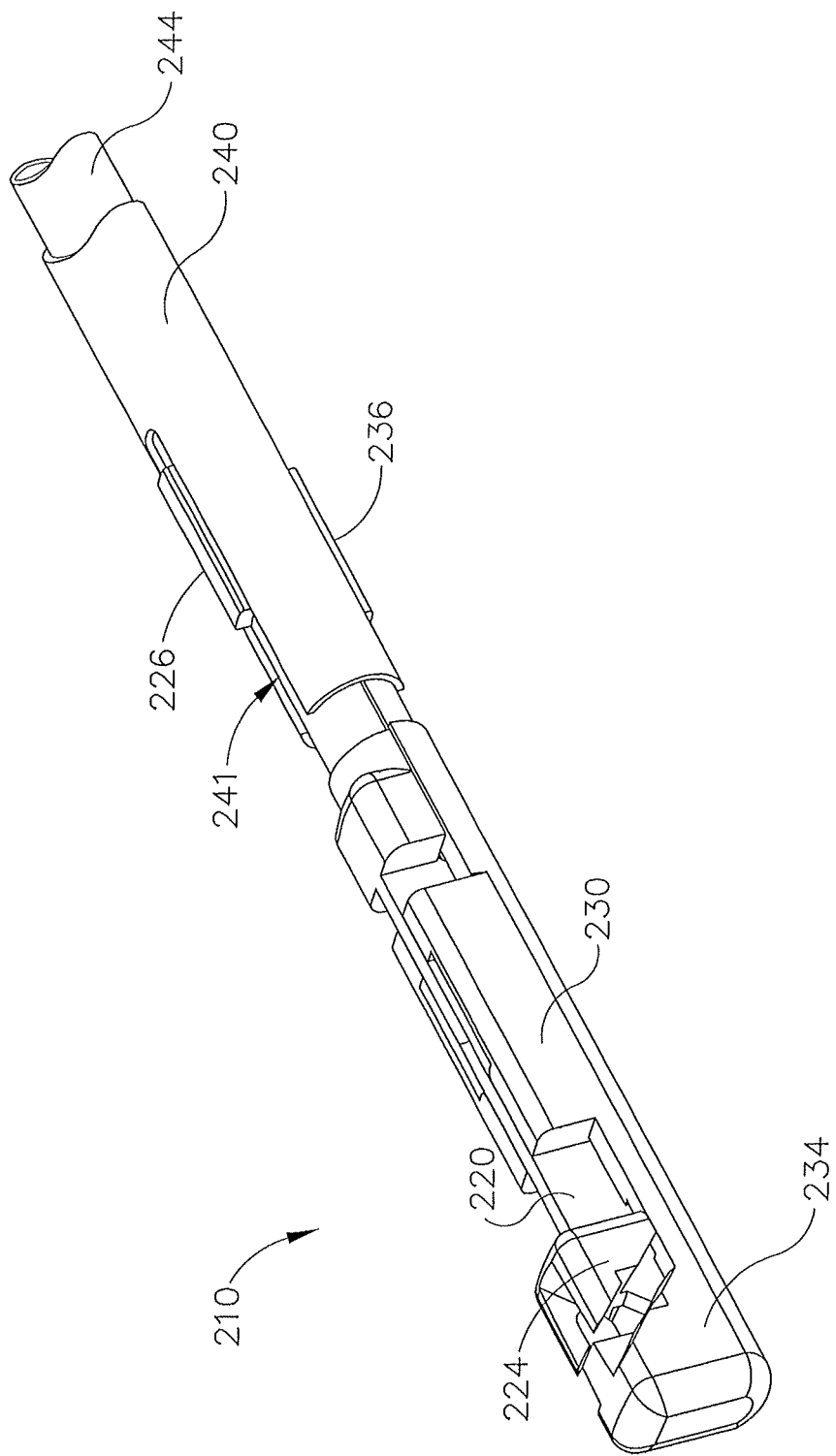
FIG. 3A depicts a first partial perspective view of a first needle grasping arm of the end effector of FIG. 2A
Figure 3B:
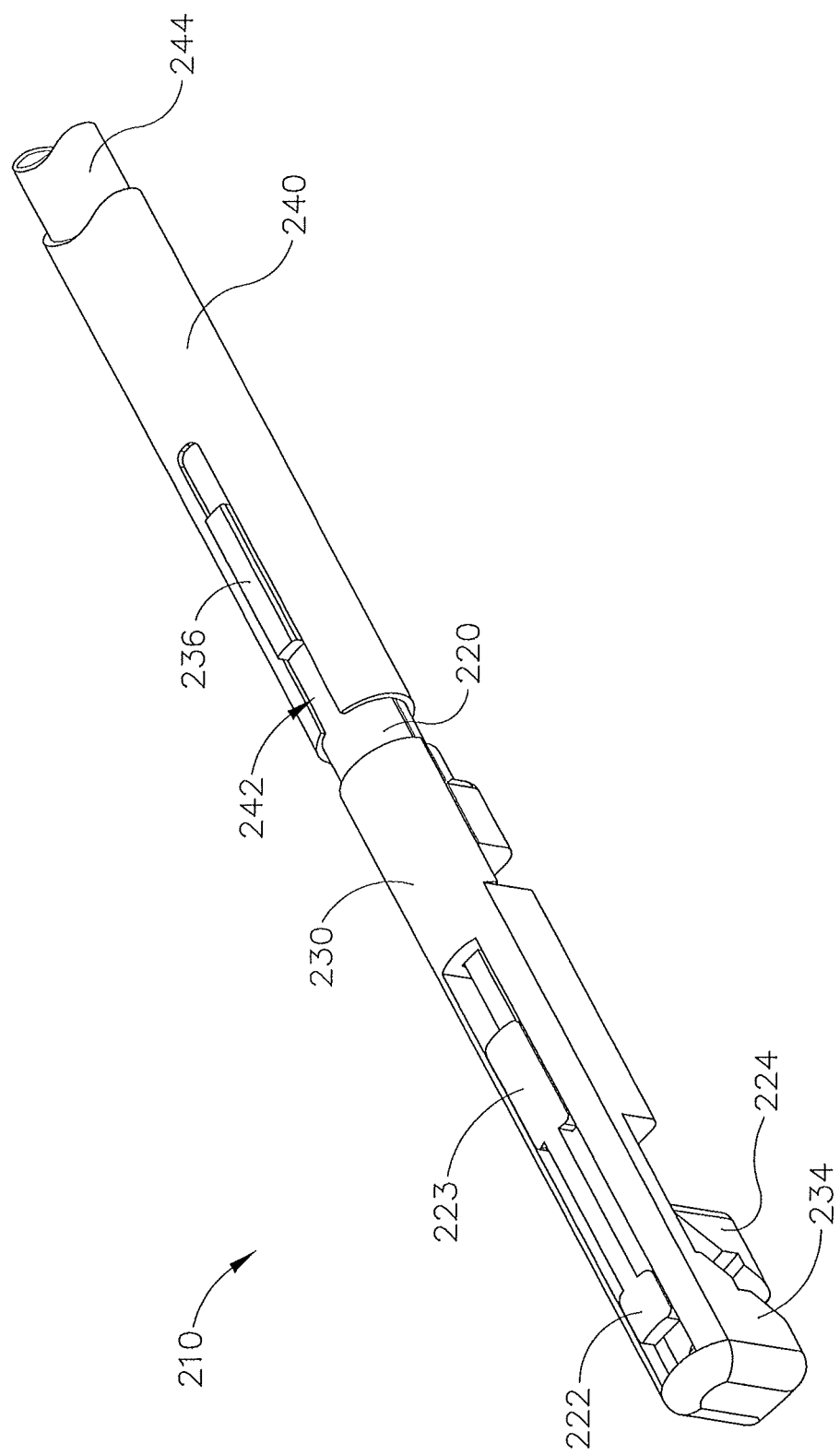
FIG. 3B depicts a second partial perspective view of the first needle grasping arm of FIG. 3A.
Figure 3C:
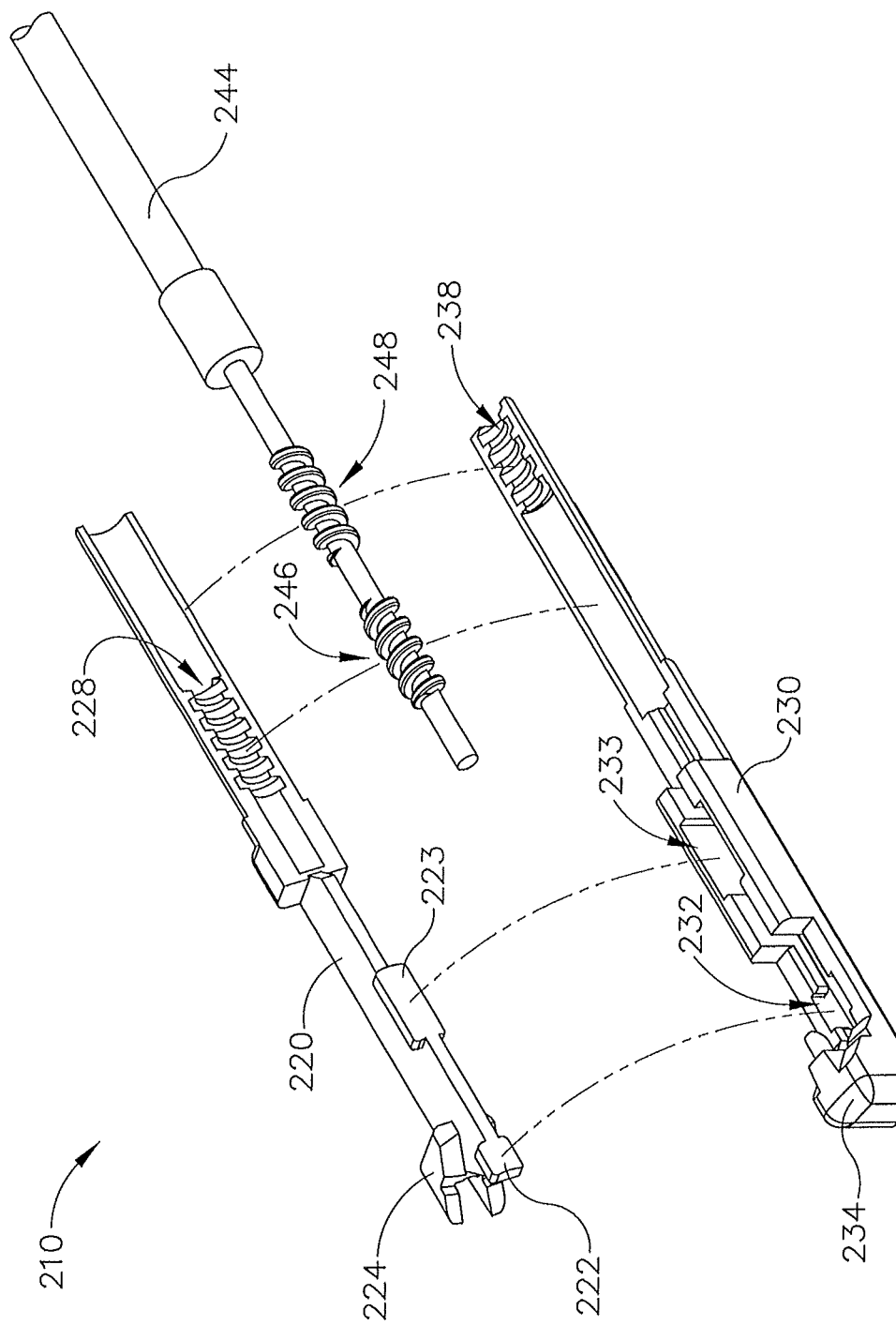
FIG. 3C depicts a partial exploded view of the first needle grasping arm of FIG. 3A.

FIGS. 3A-3C show an exploded view of a first grasping arm (210) in greater detail. First grasping arm (210) comprises a first jaw (220) and a second jaw (230). Referring to FIGS. 3A-3B, jaws (220, 230) substantially align with each other and are slidable longitudinally relative to each other. As shown in FIG. 3B, jaw (220) includes a pair of flanges (222, 223) that are received through corresponding openings (232, 233) of second jaw (230) during assembly of arm (210). Thereafter, flanges (222, 223) substantially prevent jaws (220, 230) from deflecting transversely away from each other. Jaws (220, 230) also include complementary needle grasping features (224, 234) that are configured to selectively grasp needle (50) as will be described in greater detail below. The proximal portion of jaws (220, 230) each includes a transversely extending fin (226, 236). Fins (226, 236) are slidably disposed in corresponding distal slots (241, 242) of a sheath (240) (shown in FIG. 6). Sheath (240) extends along the length of shaft (100) and is substantially fixed within shaft (100). In particular, sheath (240) does not rotate or translate relative to shaft (100) in this example. Sheath (240) thus provides a mechanical ground in the angular direction. It should therefore be understood that the relationship between fins (226, 236) and slots (241, 242) prevent first grasping arm (210) from rotating relative to shaft (100). In some other versions, however, first grasping arm (210) is rotatable relative to shaft (100) (e.g., by rotating sheath (240) within shaft (100), etc.). It should also be understood that, in the present example, the relationship between fins (226, 236) and slots (241, 242) still permits jaws (220, 230) to translate relative to sheath (240) and shaft (100).

Jaws (220, 230) of the present example are simultaneously movable in opposite directions to selectively expand or reduce an opening formed by grasping features (224, 234) to receive needle (50). To open and receive needle (50), first jaw (220) moves proximally toward shaft (100) and second jaw (230) simultaneously moves distally away from shaft (100) to enlarge the opening defined by grasping features (224, 234) to receive needle (50). To close and grip needle (50), first jaw (220) has moved distally away from shaft (100) and second jaw (230) has simultaneously moved proximally toward shaft (100) to reduce the opening defined by grasping features (224, 234) to securely grasp needle (50). In some versions, one jaw (220, 230) remains longitudinally stationary while the other jaw translates longitudinally to grasp or release needle (50) between grasping features (224, 234). However, it should be understood that in versions such as the present example where jaws (220, 230) both move simultaneously in opposite directions, such motion may further promote alignment of needle (50) within grasping features (224, 234) as compared to versions where one jaw (220, 230) always stays longitudinally fixed relative to shaft (100). In other words, having both grasping features (224, 234) always spaced equidistantly away from the intended path of needle (50) (regardless of whether jaws (220, 230) are open or closed) may better accommodate incidental deflections of needle (50) away from that intended path in either direction during use of instrument (10). Arm (210) may thus be particularly suited to accommodate instances where needle (50) has deviated away from the expected perpendicular plane of motion as described above.

As shown in FIG. 3C, to provide the simultaneous opposing motion of jaws (220, 230), a first drive shaft (244) includes a first threaded section (246) and a second threaded section (248). First drive shaft (244) is coaxially positioned within sheath (240), shown in FIG. 6, and is rotatable within sheath (240). First drive shaft (244) of the present example is rotatably driven from within handle portion (400), as will be discussed in greater detail below. The threading of first threaded section (246) is oriented opposite to the threading of second threaded section (248), such that threaded sections (246, 248) have opposite pitches. The proximal portions of jaws (220, 230) together encompass the distal portion of first drive shaft (244). In particular, the proximal portion of first jaw (220) includes threading (228) that meshes with first threaded section (246); while the proximal portion of second jaw (230) includes threading (238) that meshes with second threaded section (248). It should therefore be understood that threading (228) has a pitch that is opposite to the pitch of threading (238). It should also be understood that, due to the relationships and orientations of threaded sections (246, 248) and threading (228, 238), first drive shaft (244) will cause jaws (220, 230) to simultaneously translate away from each other when first drive shaft (244) is rotated in one direction; while first drive shaft (244) will cause jaws (220, 230) to simultaneously translate toward each other when first drive shaft (244) is rotated in the other direction.

It should be understood that the opposing-thread configuration described above may require relatively low torsional force to rotate first drive shaft (244) to drive jaws (220, 230) toward and away from each other. It should also be understood that the opposing-thread configuration described above may provide a relatively high holding force. For instance, when needle grasping features (224, 234) are driven toward each other to secure needle (50) and needle (50) is off-plane for whatever reason (e.g., incidentally oriented slightly obliquely relative to longitudinal axis (130) of shaft (100), etc.), the needle holding forces at grasping features (224, 234) may be self-reinforcing due to opposing forces provided through the opposing thread configuration described above, providing a mechanical advantage to urge needle (50) back into the desired planar orientation, even if tissue or some other structure is resisting such movement of needle (50) into the desired planar orientation. Similarly, the opposing thread configuration described above may provide friction that acts as an anti-backup feature, substantially resisting inadvertent separation of grasping features (224, 234), thereby providing a very secure hold of needle (50). Other suitable components that may be used to provide opposing motion of grasping features (224, 234) (e.g., a pinion with opposing racks, etc.) will be apparent to those of ordinary skill in the art in view of the teachings herein.

It should also be understood that, while first drive shaft (244) rotates about an axis that is parallel to longitudinal axis (130) of shaft (100), alternative drive systems that include a rotary member may provide rotation of such a rotary member about an axis that is not parallel to longitudinal axis (130) of shaft (100). For instance, a pinion based drive system may provide rotation of a drive pinion about an axis that is perpendicular to longitudinal axis (130) of shaft (100). Other suitable ways in which jaws (220, 230) may be actuated will be apparent to those of ordinary skill in the art in view of the teachings herein. First grasping arm (210) may be further constructed in accordance with the teachings of U.S. patent application Ser. No. 13/295,203, entitled "Laparoscopic Suturing Instrument with Dual-Action Needle Graspers," filed Nov. 11, 2011, now U.S. Pat. No. 8,702,732 and/or U.S. patent application Ser. No. 13/295, 210, entitled "Laparoscopic Suturing Instrument with Perpendicular Eccentric Needle Motion," filed Nov. 11, 2011, now U.S. Pat. No. 8,906,043, the disclosures of which are incorporated by reference herein.

B. Exemplary Second Grasping Arm

Figure 4B:
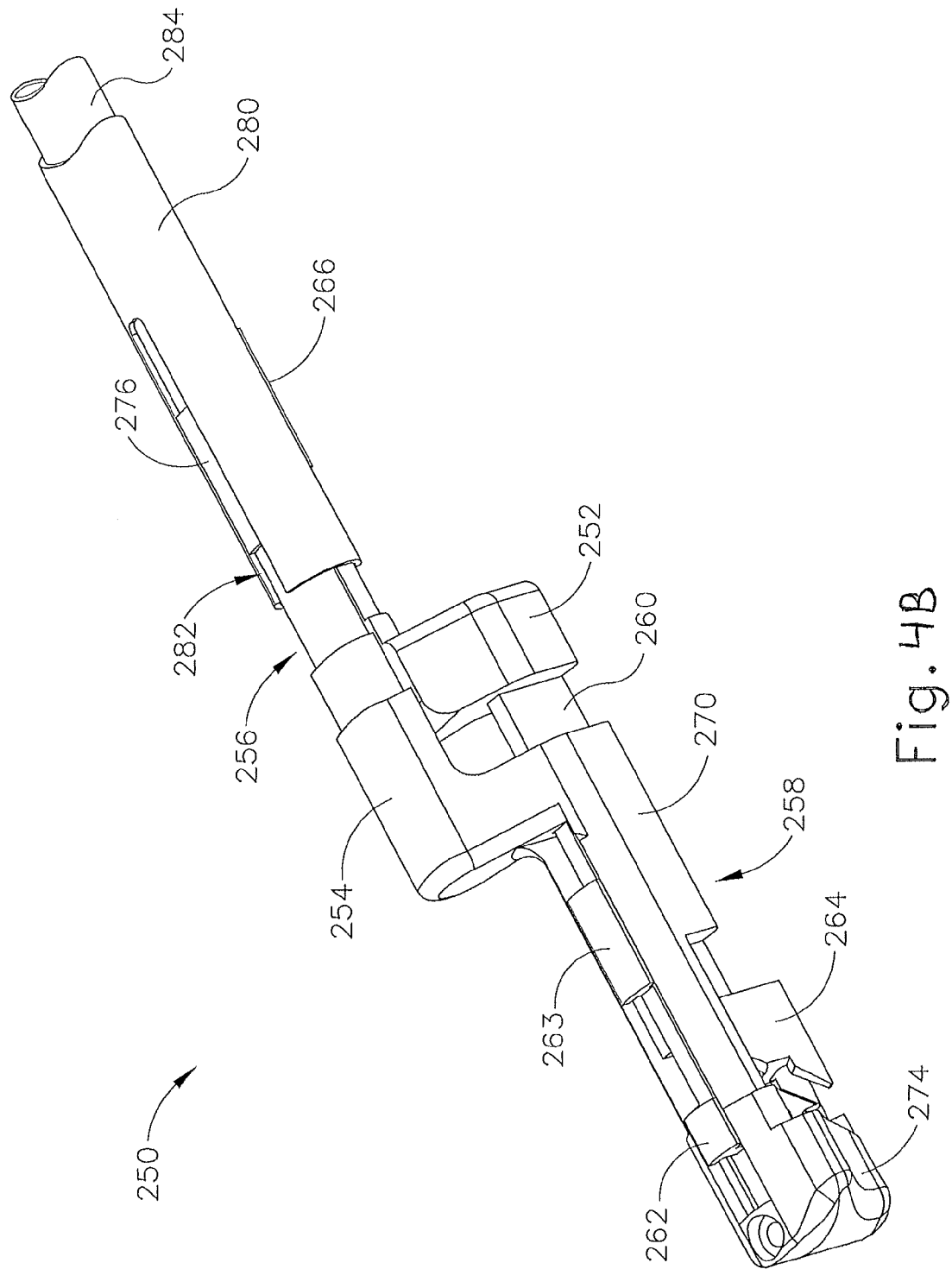
FIG. 4B depicts a second partial perspective view of the second needle grasping arm of FIG. 4A.
Figure 4C:
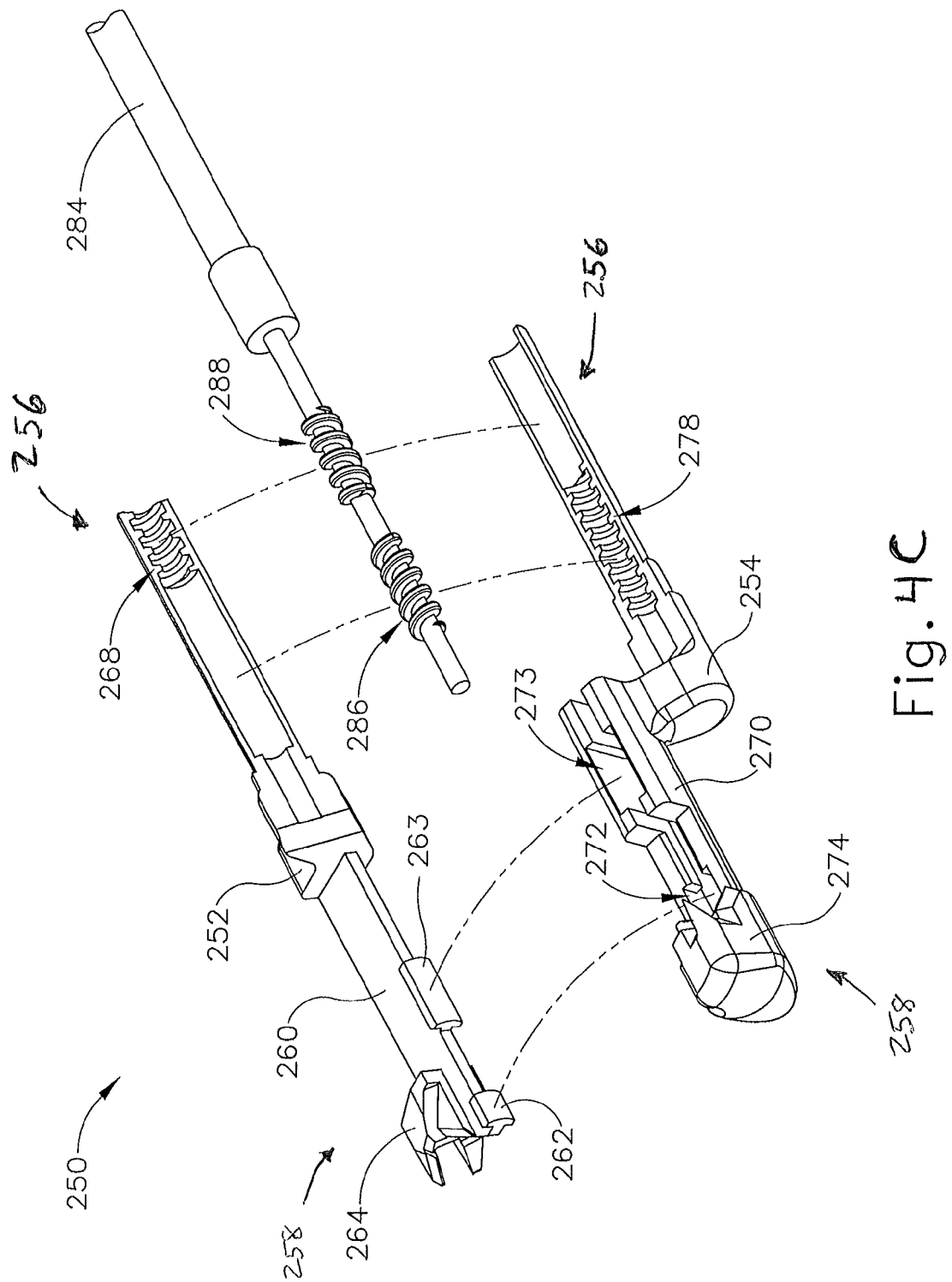
FIG. 4C depicts a partial exploded view of the second needle grasping arm of FIG. 4A.

FIGS. 4A-4C show second grasping arm (250) in greater detail having a first jaw (260) and a second jaw (270). Referring initially to FIGS. 4A-4B, jaws (260, 270) substantially align with each other and are slidable longitudinally relative to each other. As shown in FIG. 4B, first jaw (260) includes a pair of flanges (262, 263) that are received through corresponding openings (272, 273) of second jaw (270) during assembly of arm (250). Thereafter, flanges (262, 263) prevent jaws (260, 270) from deflecting transversely away from each other. Jaws (260, 270) also include complementary needle grasping features (264, 274) that are configured to selectively grasp needle (50) as will be described in greater detail below. The proximal portion of each jaw (260) includes a transversely extending fin (266, 276). Fins (266, 276) are slidably disposed in corresponding distal slots (281, 282) of a sheath (280), shown in FIG. 6. Each jaw (260, 270) of second grasping arm (250) includes a dogleg section (252, 254). Each dogleg section (252, 254) forms a pair of right angles between a proximal portion (256) of grasping arm (250) and a distal portion (258) of grasping arm (250). The configuration of dogleg sections (252, 254) provides distal portion (258) in a parallel yet offset position relative to proximal portion (256). Thus, when grasping arm (250) is rotated about a longitudinal axis (140) extending along the length of the proximal portion (256) of grasping arm (250), the distal portion (258) of grasping arm (250) rotates in an orbital motion about that longitudinal axis (140). Such motion will be described in greater detail below.

Figure 6:
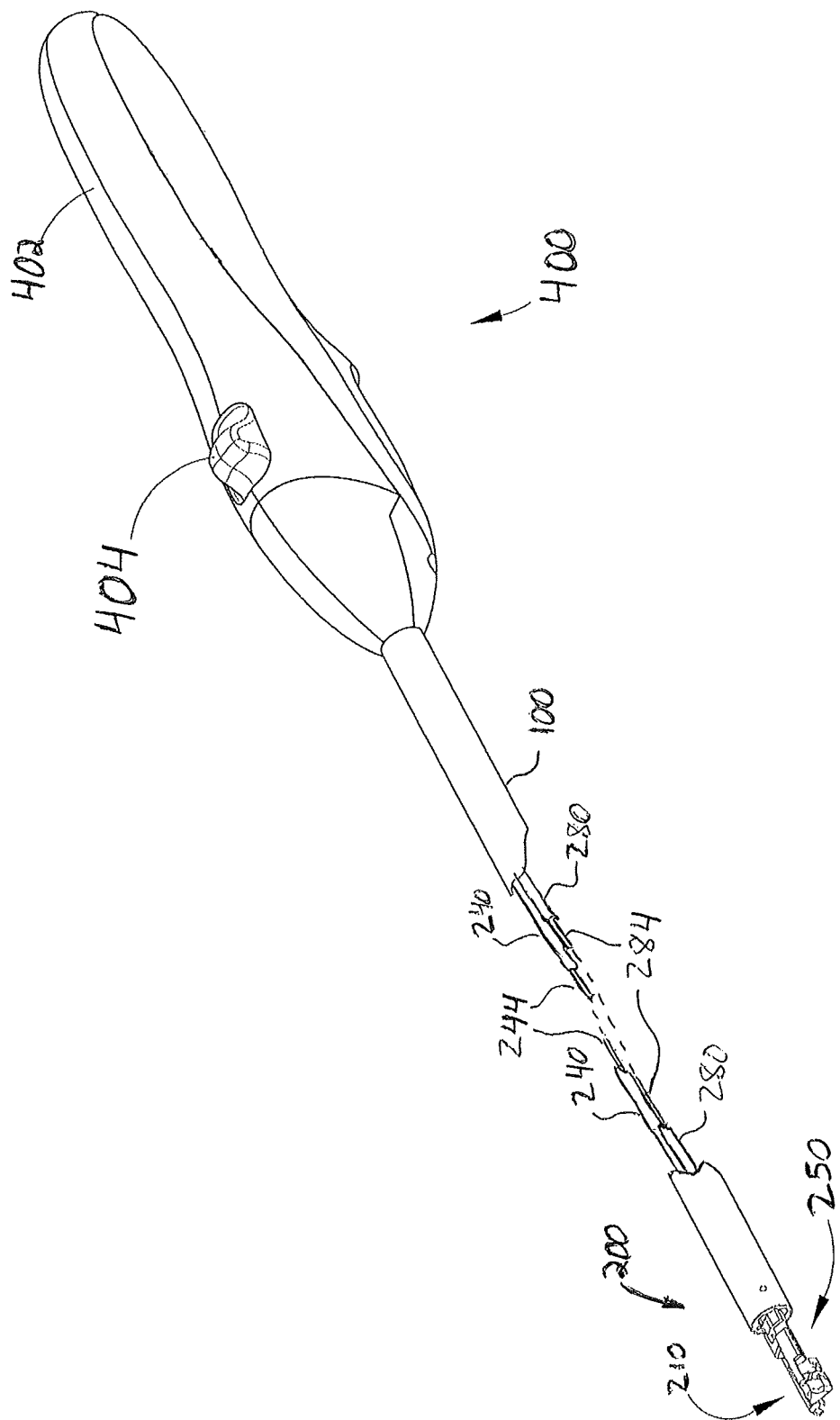
FIG. 6 depicts a perspective view of the laparoscopic suturing instrument of FIG. 1 with a portion of an outer shaft cut away to show the interior shafts.

Sheath (280), shown in FIG. 6, extends along the length of shaft (100) and is partially fixed within shaft (100). In particular, sheath (280) does not translate relative to shaft (100) in this example, though sheath (280) is rotatable relative to shaft (100). For instance, sheath (280) may be selectively rotated in either direction by a motor, trigger, actuator, and/or any other element as will be described in greater detail below. It should therefore be understood that rotation of sheath (280) relative to shaft (100) will provide rotation of second grasping arm (250) relative to shaft (100), due to the relationship between fins (266, 276) and slots (281, 282). As noted above, when second grasping arm (250) is rotated by sheath (280), the distal portion (258) of grasping arm (250) rotates in an orbital motion about longitudinal axis (140) that is defined by both sheath (280) and the proximal portion (256) of grasping arm (250). In some other versions, second grasping arm (250) is non-rotatable relative to shaft (100). It should also be understood that, in the present example, the relationship between fins (266, 276) and slots (281, 282) permits jaws (260, 270) to translate relative to sheath (280) and shaft (100).

In the present example, jaws (260, 270) are simultaneously movable in opposite directions to selectively expand or reduce an opening formed by grasping features (264, 274) to receive needle (50). To open and receive needle (50), first jaw (260) moves proximally toward shaft (100) and second jaw (270) simultaneously moves distally away from shaft (100) to enlarge the opening defined by grasping features (264, 274) to receive needle (50). To close and grip needle (50), first jaw (260) moves distally away from shaft (100) and second jaw (270) simultaneously moves proximally toward shaft (100) to reduce the opening defined by grasping features (264, 274) to securely grasp needle (50). In some versions, one jaw (260, 270) remains longitudinally stationary while the other jaw translates longitudinally to grasp or release needle (50) between grasping features (264, 274). However, it should be understood that in versions such as the present example where jaws (260, 270) both move simultaneously in opposite directions, such motion may further promote alignment of needle (50) within grasping features (264, 274) as compared to versions where one jaw (260, 270) always stays longitudinally fixed relative to shaft (100). In other words, having both grasping features (264, 274) always spaced equidistantly away from the intended path of needle (50) (regardless of whether jaws (260, 270) are open or closed) may better accommodate incidental deflections of needle (50) away from that intended path in either direction during use of instrument (10). Arm (250) may thus be particularly suited to accommodate instances where needle (50) has deviated away from the expected perpendicular plane of motion as described above.

As shown in FIG. 4C, to provide the simultaneous opposing motion of jaws (260, 270), a second drive shaft (284) that includes a first threaded section (286) and a second threaded section (288). Second drive shaft (284) is coaxially positioned within sheath (280) and is rotatable within sheath (280). Second drive shaft (284) of the present example is rotatably driven from within handle portion (400), as will be discussed in greater detail below. The threading of first threaded section (286) is oriented opposite to the threading of second threaded section (288), such that threaded sections (286, 288) have opposite pitches. The proximal portions of jaws (260, 270) together encompass the distal portion of drive shaft (284). In particular, the proximal portion of first jaw (260) includes threading (268) that meshes with first threaded section (286); while the proximal portion of second jaw (270) includes threading (278) that meshes with second threaded section (288). It should therefore be understood that threading (268) has a pitch that is opposite to the pitch of threading (278). It should also be understood that, due to the relationships and orientations of threaded sections (286, 288) and threading (268, 278), second drive shaft (284) will cause jaws (260, 270) to simultaneously translate away from each other when second drive shaft (284) is rotated in one direction; while second drive shaft (284) will cause jaws (260, 270) to simultaneously translate toward each other when second drive shaft (284) is rotated in the other direction.

In some settings, the rotational position of sheath (280) is fixed relative to shaft (100) when second drive shaft (284) is rotated relative to shaft (100). Thus, sheath (280) substantially holds the rotational position of jaws (260, 270) when second drive shaft (284) is rotated. In some other settings, sheath (280) and second drive shaft (284) are rotated simultaneously relative to shaft (100). In some such instances, sheath (280) and second drive shaft (284) are rotated in the same direction and at the same speed, such that second drive shaft (284) and jaws (260, 270) are rotated in the same direction and at the same speed. Thus, the longitudinal positioning of jaws (260, 270) remains fixed during such rotation. As another merely illustrative variation, sheath (280) and second drive shaft (284) may be rotated simultaneously relative to shaft (100), but at different speeds and/or in different directions. Such a scheme provides a rotation differential between jaws (260, 270) and second drive shaft (284), such that jaws (260, 270) may open or close while second grasping arm (250) is simultaneously being rotated relative to shaft (100).

It should be understood that the opposing thread configuration described above may require relatively low torsional force to rotate second drive shaft (284) to drive jaws (260, 270) toward and away from each other. It should also be understood that the opposing thread configuration described above may provide a relatively high holding force. For instance, when needle grasping features (264, 274) are driven toward each other to secure needle (50) and needle (50) is off-plane for whatever reason (e.g., incidentally oriented slightly obliquely relative to longitudinal axis (130) of shaft (100), etc.), the needle holding forces at grasping features (264, 274) may be self-reinforcing due to opposing forces provided through the opposing thread configuration described above, providing a mechanical advantage to urge needle (50) back into the desired planar orientation, even if tissue or some other structure is resisting such movement of needle (50) into the desired planar orientation. Similarly, the opposing thread configuration described above may provide friction that acts as an anti-backup feature, substantially resisting inadvertent separation of grasping features (264, 274), thereby providing a very secure hold of needle (50). Other suitable components that may be used to provide opposing motion of grasping features (264, 274) (e.g., a pinion with opposing racks, etc.) will be apparent to those of ordinary skill in the art in view of the teachings herein.

It should also be understood that, while second drive shaft (284) rotates about a longitudinal axis (140) that is parallel to longitudinal axis (130) of shaft (100), alternative drive systems that include a rotary member may provide rotation of such a rotary member about an axis that is not parallel to longitudinal axis (130) of shaft (100). For instance, a pinion based drive system may provide rotation of a drive pinion about an axis that is perpendicular to longitudinal axis (130) of shaft (100). Other suitable ways in which one or more components of second grasping arm (250) may be actuated will be apparent to those of ordinary skill in the art in view of the teachings herein. Second grasping arm (250) may be further constructed in accordance with the teachings of U.S. patent application Ser. No. 13/295,203, entitled "Laparoscopic Suturing Instrument with Dual-Action Needle Graspers," filed Nov. 11, 2011, now U.S. Pat. No. 8,702,732 and/or U.S. patent application Ser. No. 13/295,210, entitled "Laparoscopic Suturing Instrument with Perpendicular Eccentric Needle Motion," filed Nov. 11, 2011, now U.S. Pat. No. 8,906,043, the disclosures of which are incorporated by reference herein.

III. Exemplary Operation of End Effector

Figure 5A:
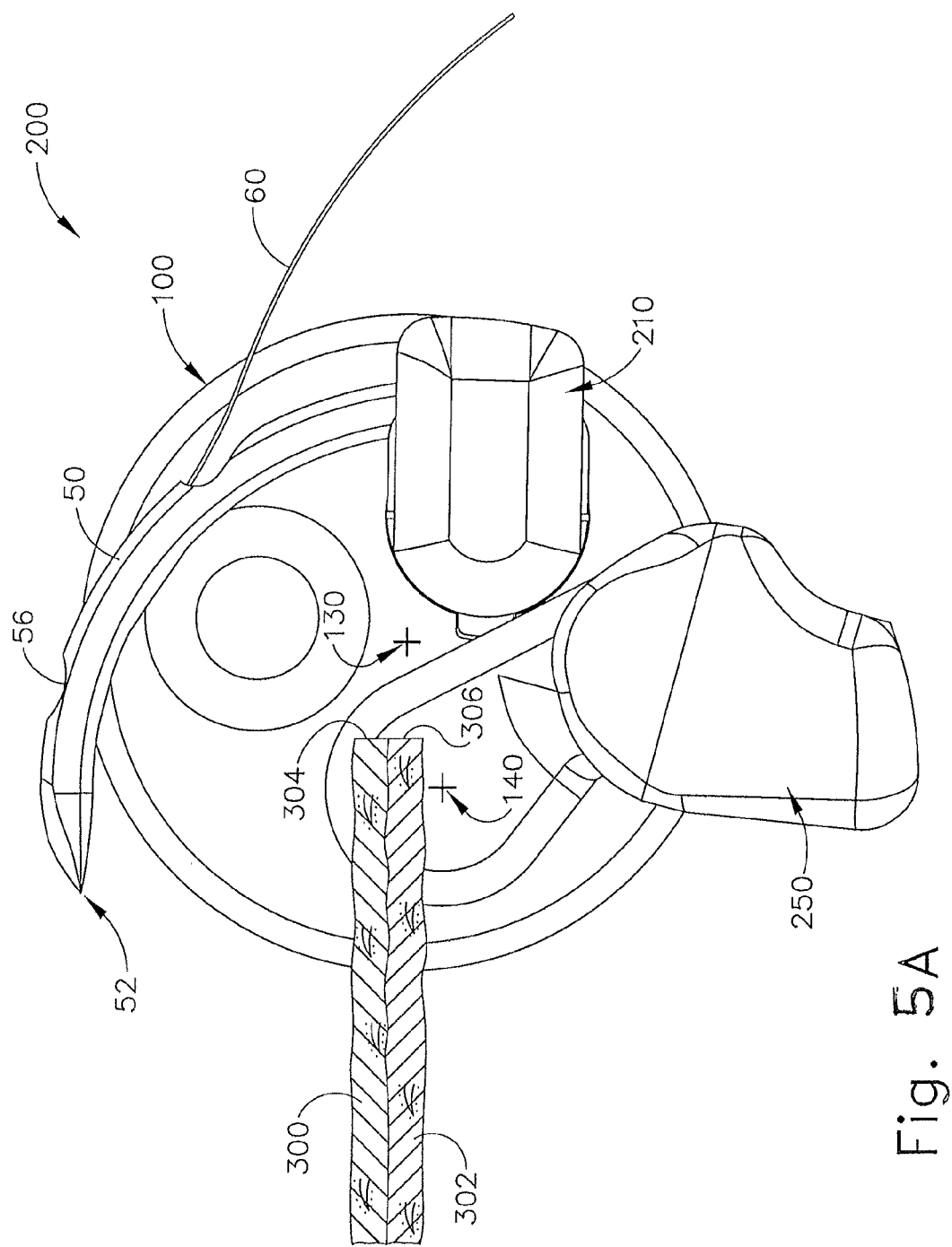
FIG. 5A depicts an end elevation view of the end effector and needle of FIG. 2A, during an exemplary first stage of operation.

FIGS. 5A-5H depict a merely exemplary method for using surgical instrument (10). In particular, FIG. 5A shows end effector (200) positioned adjacent to apposed layers (300, 302) of tissue. End effector (200) is positioned such that longitudinal axis (130) of shaft (100) is substantially parallel to the outer edges (304, 306) of tissue layers (300, 302). In this sense, "substantially parallel" simply means that end effector (200) is oriented in relation to tissue layers (300, 302) in a manner sufficient to enable needle (50) to be passed through tissue layers (300, 302). It should therefore be understood that longitudinal axis (130) need not necessarily be truly parallel with outer edges (304, 306), though longitudinal axis (130) may in fact be truly parallel with outer edges (304, 306) in some instances. It should also be understood that instrument (10) and needle (50) may be used to secure tissue together in an edge-to-edge arrangement rather than securing apposed layers (300, 302) as shown. Other suitable settings in which instrument (10) and needle (50) may be used will be apparent to those of ordinary skill in the art in view of the teachings herein. It should also be understood that the curved configuration of needle (50) may provide a more intuitive operation for the surgeon than a straight needle would, such as by providing better predictability for where sharp tip (52) will come through tissue.

Figure 5B:
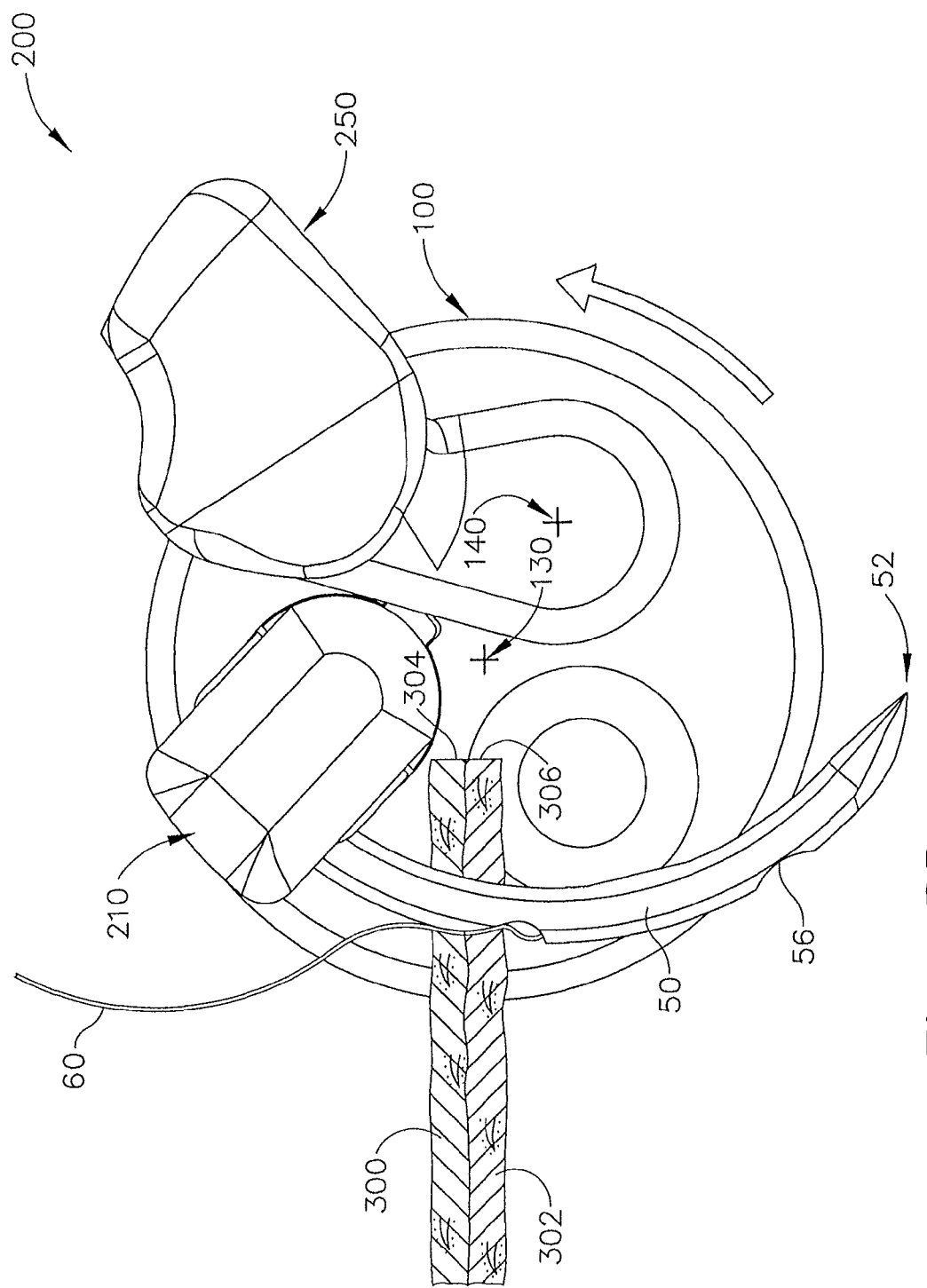
FIG. 5B depicts an end elevation view of the end effector and needle of FIG. 2A, during an exemplary second stage of operation.

As shown in FIG. 5A, first grasping arm (210) is securely holding needle (50), with sharp tip (52) exposed. In particular, grasping portions (224, 234) of jaws (220, 230) hold needle (50) at grasping region (56). Needle (50) is oriented along a plane that is substantially transverse to longitudinal axis (130). Once end effector (200) has been positioned as shown in FIG. 5A, the entire instrument (10) is rotated about longitudinal axis (130) to drive sharp tip (52) through tissue layers (300, 302), as shown in FIG. 5B. In the example shown, the rotational direction for instrument (10) is counterclockwise viewed from the distal end toward the proximal end, though it should be understood that instrument (10) may be rotated clockwise instead (e.g., depending on the orientation of sharp tip (52)). During the transition from the position of FIG. 5A to the position of FIG. 5B, the rotational position of grasping arms (210, 250) relative to shaft (100) remains fixed, such that grasping arms (210, 250) rotate unitarily with shaft (100) about longitudinal axis (130). The longitudinal position of jaws (220, 230, 260, 270) also remains fixed during this transition. As can also be seen in FIG. 5B, needle (50) has started to pull suture (60) through tissue layers (300, 302) at this stage. It should be understood that, in the stages shown in FIGS. 5A-5B, grasping arms (210, 250) and needle (50) are in the same rotational positions relative to shaft (100) as shown in FIG. 2A. It should also be noted that the configuration of end effector (200) and needle (50) may provide the surgeon with enhanced visibility of sharp tip (52) exiting tissue layers (300, 302) during the transition from FIG. 5A to FIG. 5B, particularly with second grasping arm (250) being rotated out of the way at this stage.

Figure 5C:
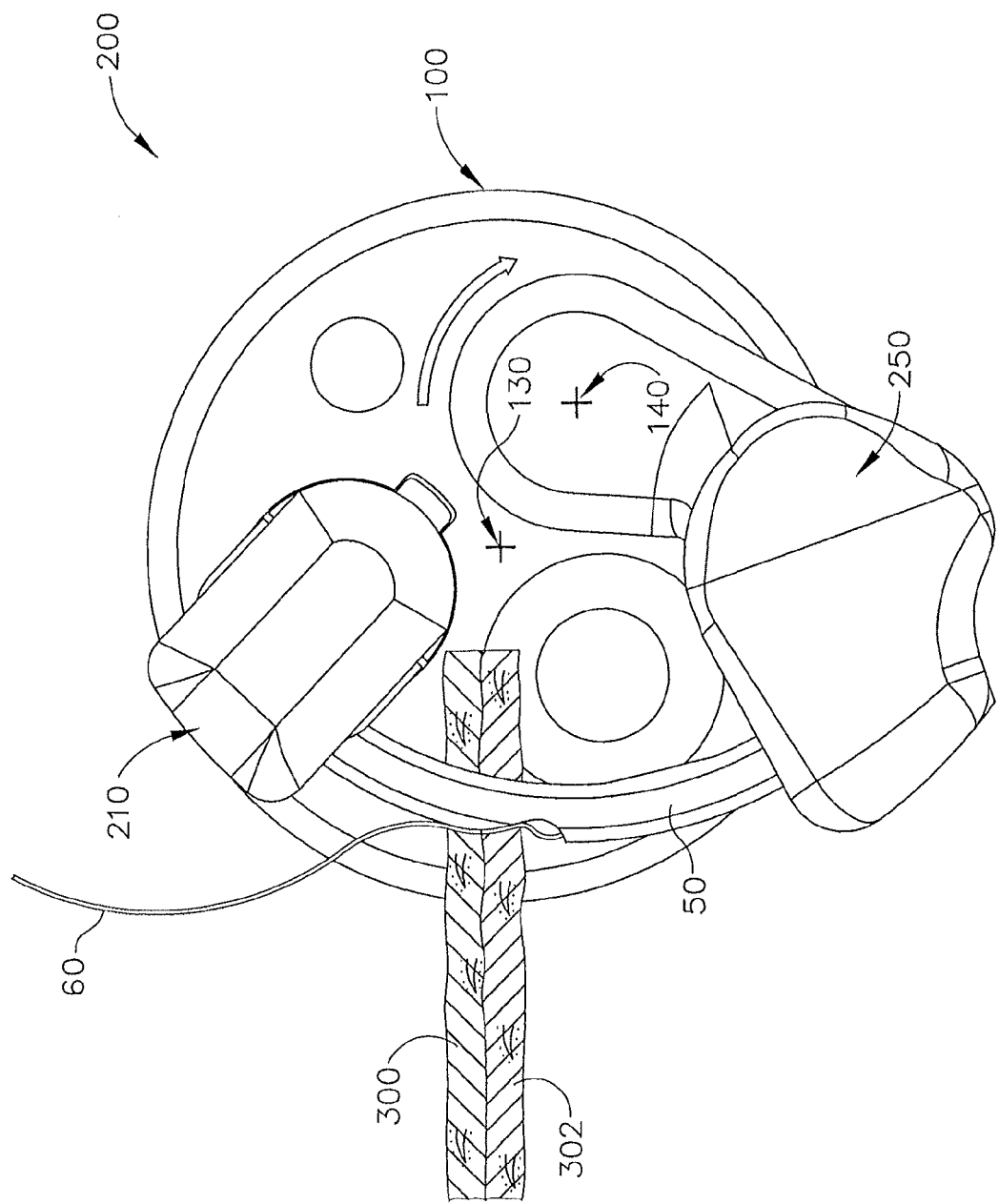
FIG. 5C depicts an end elevation view of the end effector and needle of FIG. 2A, during an exemplary third stage of operation.

After needle (50) has been driven at least partially through tissue layers (300, 302), second grasping arm (250) is rotated about its own axis (140) toward needle (50) as shown in FIG. 5C. Such rotation is provided by rotating sheath (280) relative to shaft (100). The rotational position of shaft (100) relative to longitudinal axis (130) remains fixed during the transition from the configuration shown in FIG. 5B to the configuration shown in FIG. 5C. It should be understood that, in the stage shown in FIG. 5C, grasping arms (210, 250) and needle (50) are in the same rotational positions relative to shaft (100) as shown in FIG. 2B.

In some versions, jaws (260, 270) are already opened by the time second grasping arm (250) starts rotating from the position shown in FIG. 5B to the position shown in FIG. 5C. In other versions, jaws (260, 270) are actively opened during the transition from the position shown in FIG. 5B to the position shown in FIG. 5C, such that jaws (260, 270) are fully open by the time second grasping arm (250) reaches the position shown in FIG. 5C. Once second grasping arm (250) reaches the position shown in FIG. 5C, jaws (260, 270) of second grasping arm (250) close to grasp needle (50) at grasping region (58) with grasping features (264, 274). In addition, jaws (220, 230) of first grasping arm (210) open to release needle (50) from grasping features (224, 234) at grasping region (56). In some versions, jaws (260, 270) of second grasping arm (250) close to grasp needle (50) at substantially the same time as jaws (220, 230) of first grasping needle (210) open to release needle (50). In some other versions, jaws (220, 230) of first grasping arm (210) do not open to release needle (50) until jaws (260, 270) of second grasping arm (250) have closed to grasp needle (50). Various suitable timing schemes and ways in which such schemes may be carried out will be apparent to those of ordinary skill in the art in view of the teachings herein.

Figure 5D:
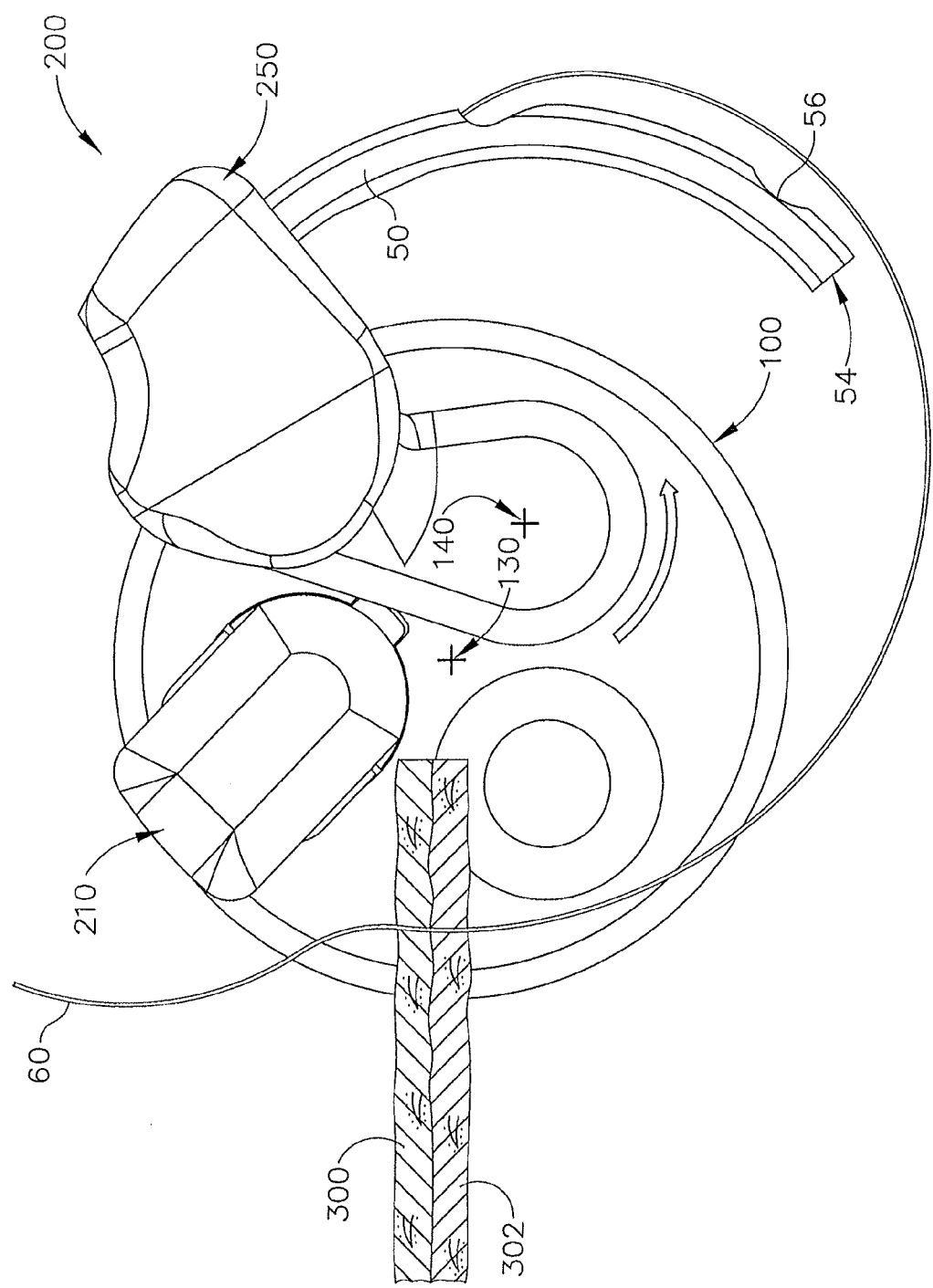
FIG. 5D depicts an end elevation view of the end effector and needle of FIG. 2A, during an exemplary fourth stage of operation.

Once control of needle (50) has been effectively passed from first grasping arm (210) to second grasping arm (250), second grasping arm (250) is rotated about longitudinal axis (140) to the position shown in FIG. 5D. Such rotation is provided by once again rotating sheath (280) relative to shaft (100), as will be described in greater detail below. The rotational position of shaft (100) relative to longitudinal axis (130) continues to be fixed during the transition from the configuration shown in FIG. 5C to the configuration shown in FIG. 5D. It should be understood that, in the stage shown in FIG. 5D, grasping arms (210, 250) and needle (50) are in the same rotational positions relative to shaft (100) as shown in FIG. 2C. As can also be seen in FIG. 5D, grasping arm (250) pulls suture (60) through tissue layers (300, 302) during the transition from FIG. 5C to FIG. 5D.

Figure 5E:
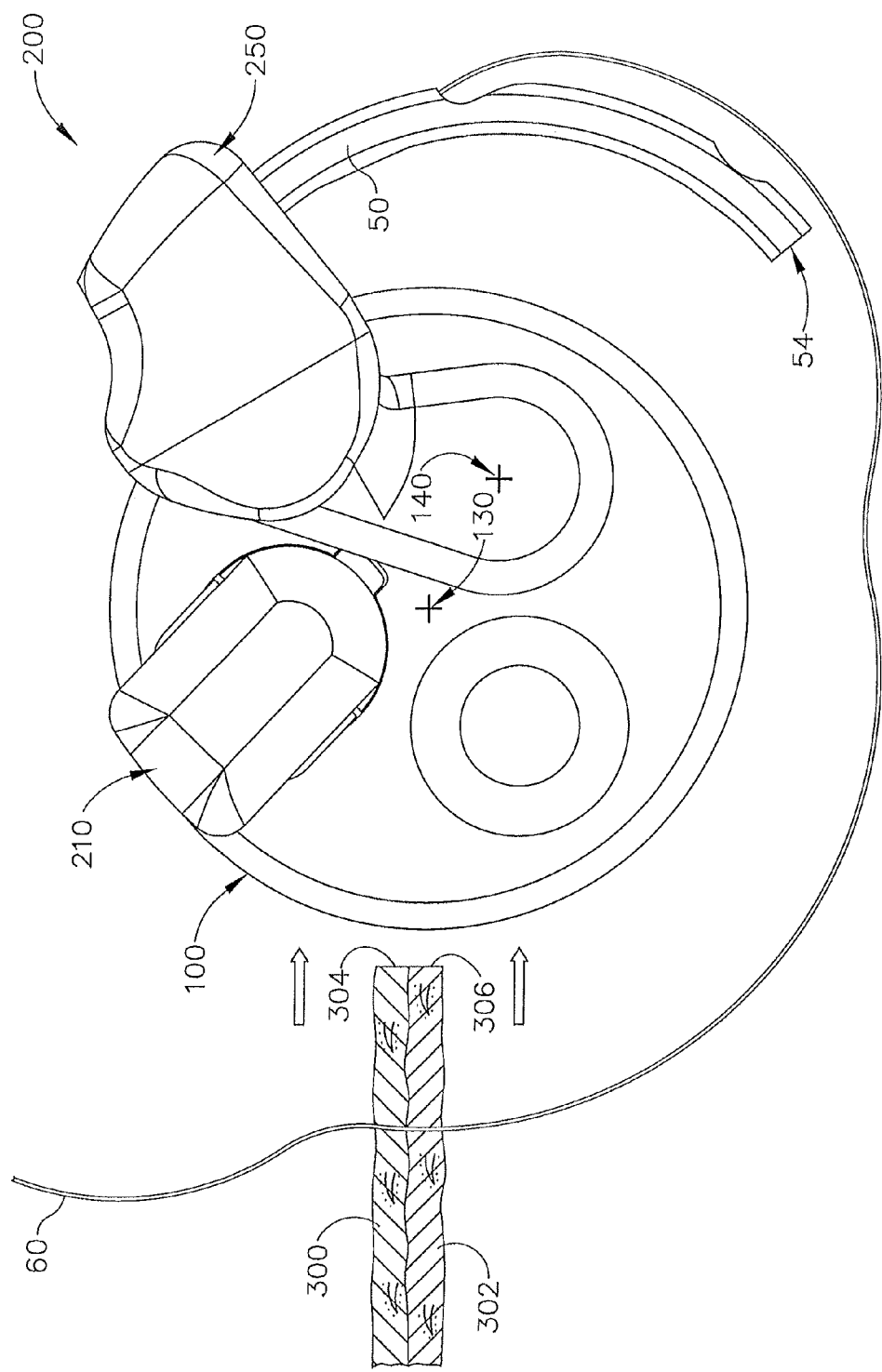
FIG. 5E depicts an end elevation view of the end effector and needle of FIG. 2A, during an exemplary fifth stage of operation.

After reaching the configuration shown in FIG. 5D, the surgeon pulls the entire end effector (200) away from tissue layers (300, 302), along a path that is substantially transverse to longitudinal axis (130), as shown in FIG. 5E. It should be understood that this path may be oblique relative to longitudinal axis (130) and/or edges (304, 306), helical, and/or of any other suitable orientation. It should also be understood that neither arm (210, 250) is rotated relative to shaft (100) in the present example during the transition from the position shown in FIG. 5D to the position shown in FIG. 5E. Thus, in the stage shown in FIG. 5E, grasping arms (210, 250) and needle (50) are still in the same rotational positions relative to shaft (100) as shown in FIG. 2C. In moving instrument (10) away from tissue layers (300, 302) during the transition to the position shown in FIG. 5E, suture (60) is pulled further through tissue layers (300, 302).

Figure 5F:
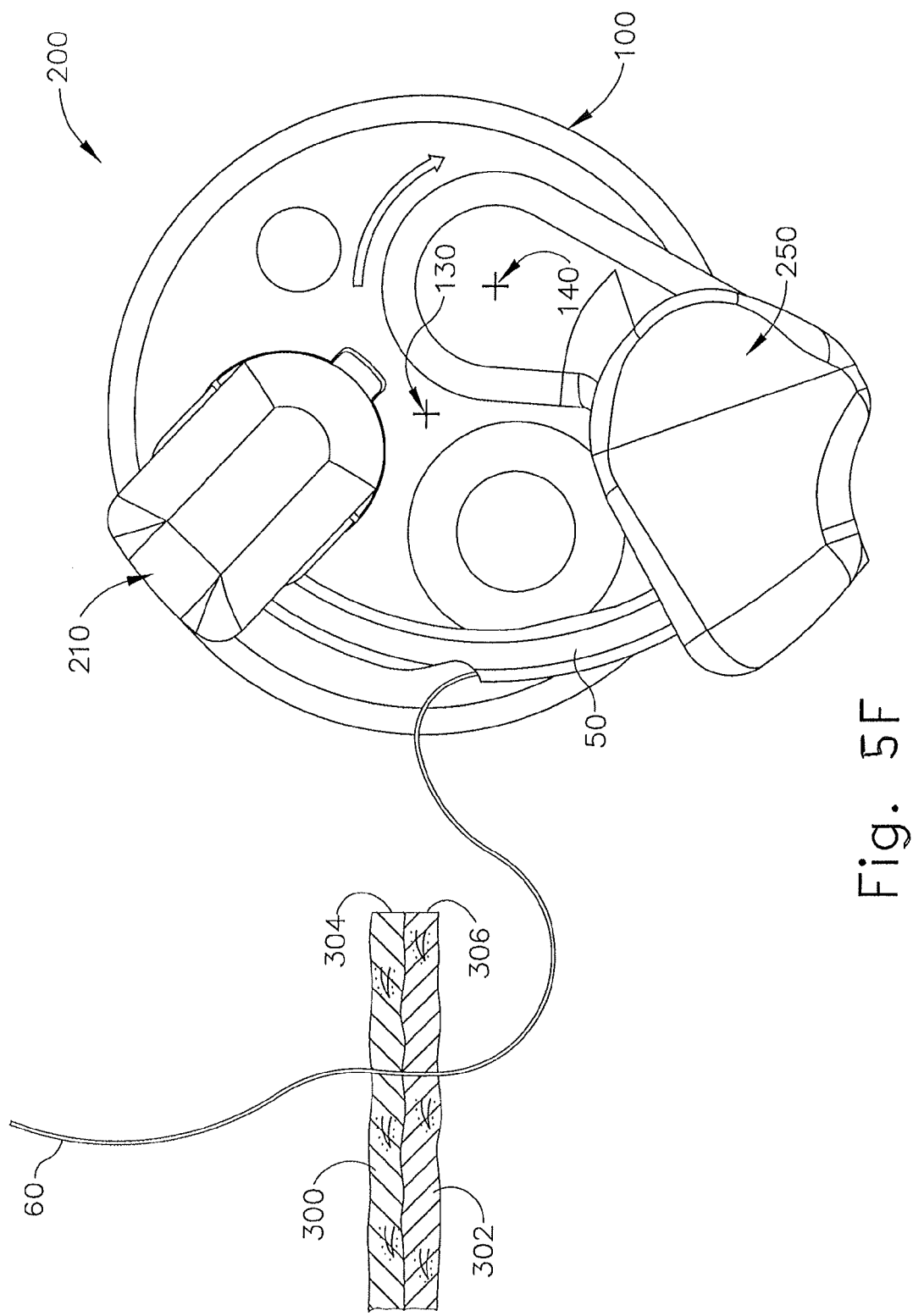
FIG. 5F depicts an end elevation view of the end effector and needle of FIG. 2A, during an exemplary sixth stage of operation.

With end effector (200) positioned sufficiently away from tissue layers (300, 302), second grasping arm (250) is rotated about longitudinal axis (140) to the position shown in FIG. 5F. The rotational position of shaft (100) relative to longitudinal axis (130) remains fixed during the transition from the configuration shown in FIG. 5E to the configuration shown in FIG. 5F. It should be understood that, in the stage shown in FIG. 5F, grasping arms (210, 250) and needle (50) are in the same rotational positions relative to shaft (100) as shown in FIG. 2B. End effector (200) is positioned far enough away from tissue layers (300, 302) during the transition from the position shown in FIG. 5E to the position shown in FIG. 5F such that blunt end (54) of needle (50) does not touch tissue layers (300, 302). The rotation of second grasping arm (250) to the position shown in FIG. 5F places grasping region (58) of needle (50) back between grasping portions (224, 234) of jaws (220, 230) of first grasping arm (210).

In some versions, jaws (220, 230) of first grasping arm (210) are already opened by the time second grasping arm (250) starts rotating from the position shown in FIG. 5E to the position shown in FIG. 5F. In other versions, jaws (220, 230) of first grasping arm (210) are actively opened during the transition from the position shown in FIG. 5E to the position shown in FIG. 5F, such that jaws (220, 230) are fully open by the time second grasping arm (250) reaches the position shown in FIG. 5F. Once second grasping arm (250) reaches the position shown in FIG. 5F, jaws (220, 230) of first grasping arm (210) close to grasp needle (50) at grasping region (56) with grasping portions (224, 234). In addition, jaws (260, 270) of second grasping arm (250) open to release needle (50) from grasping portions (264, 274) at grasping region (58). In some versions, jaws (220, 230) of first grasping arm (210) close to grasp needle (50) at substantially the same time as jaws (260, 270) of second grasping arm (250) open to release needle (50). In some other versions, jaws (260, 270) of second grasping arm (250) do not open to release needle (50) until jaws (220, 230) of first grasping arm (210) have closed to grasp needle (50). Various suitable timing schemes and ways in which such schemes may be carried out will be described in greater detail below while others will be apparent to those of ordinary skill in the art in view of the teachings herein.

Figure 5G:
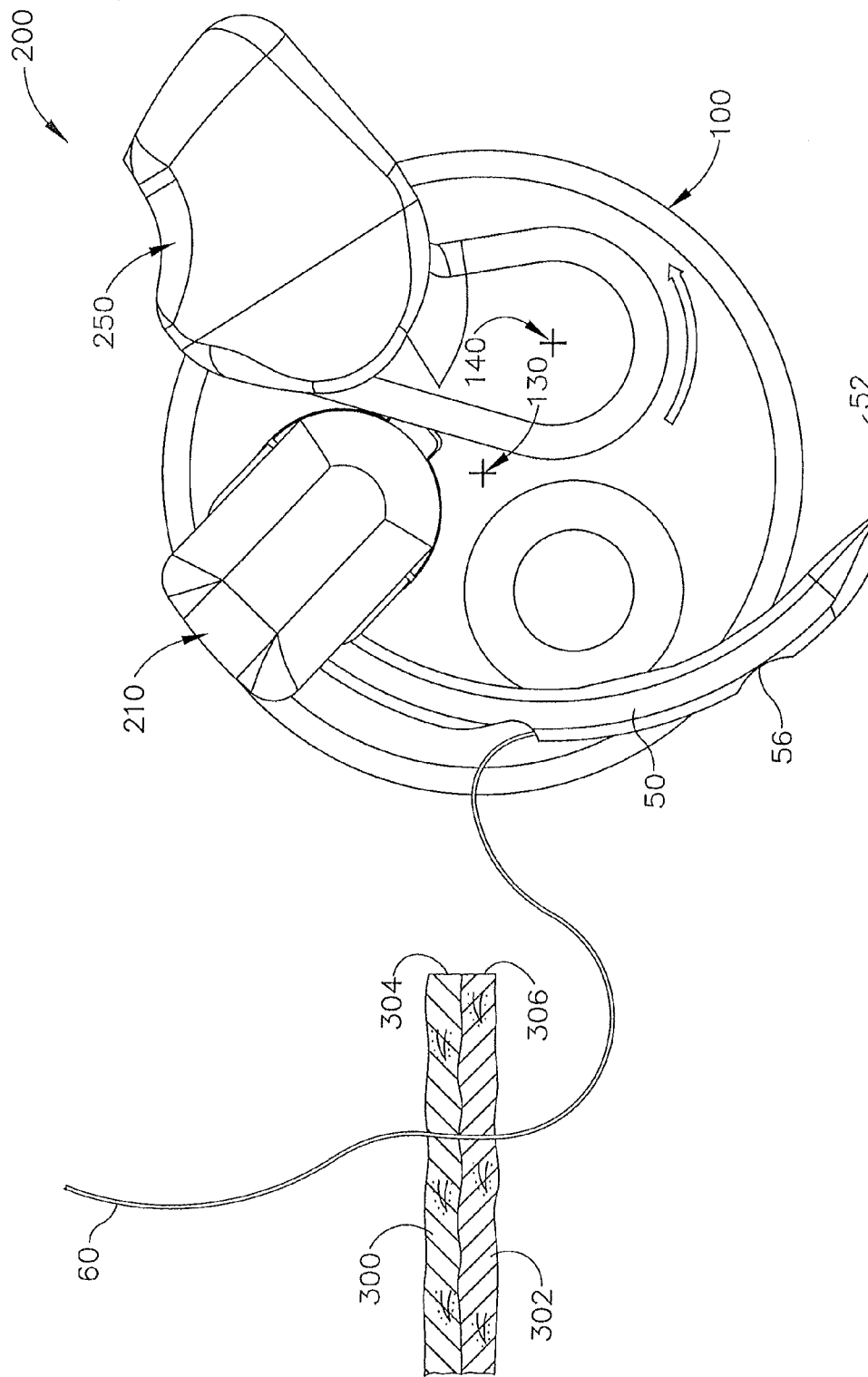
FIG. 5G depicts an end elevation view of the end effector and needle of FIG. 2A, during an exemplary seventh stage of operation.

Once control of needle (50) has been effectively passed from second grasping arm (250) back to first grasping arm (210), second grasping arm (250) is rotated about longitudinal axis (140) to the position shown in FIG. 5G. Such rotation is provided by once again rotating sheath (280) relative to shaft (100). The rotational position of shaft (100) relative to longitudinal axis (130) continues to be fixed during the transition from the position shown in FIG. 5F to the position shown in FIG. 5G. It should be understood that, in the stage shown in FIG. 5G, grasping arms (210, 250) and needle (50) are in the same rotational positions relative to shaft (100) as shown in FIG. 2A.

Once second grasping arm (250) has been rotated away from needle (50) as shown in FIG. 5G, the entire instrument (10) is once again rotated about longitudinal axis (130) to position sharp tip (52) above tissue layers (300, 302), as shown in FIG. 5H. In the example shown, the rotational direction for instrument (10) is again counterclockwise viewed from the distal end toward the proximal end, though it should be understood that instrument (10) may be rotated clockwise instead (e.g., depending on the orientation of sharp tip (52)). During this transition, the rotational position of grasping arms (210, 250) relative to shaft (100) remains fixed, such that grasping arms (210, 250) rotate unitarily with shaft (100) about longitudinal axis (130). The longitudinal position of jaws (220, 230, 260, 270) also remains fixed during this transition. In the stage shown in FIG. 5H, grasping arms (210, 250) and needle (50) remain in the same rotational positions relative to shaft (100) as shown in FIG. 2A.

Having reached the configuration shown in FIG. 5H, end effector (200) may be moved back toward tissue layers (300, 302), such as along a path transverse to longitudinal axis (130), to again reach the position shown in FIG. 5A. The above described cycle may then be repeated as many times as desired until an appropriate number of stitches have been made through tissue layers (300, 302). The free end of suture (50) may then be knotted, clipped, or otherwise secured.

It should be understood that instrument (10) may be advanced distally or proximally along longitudinal axis (130) in each stitching cycle, each stitching cycle being represented by the succession of stages depicted in FIGS. 5A-5H. For instance, instrument (10) may be advanced distally or proximally along axis (130) during the transition from the position shown in FIG. 5E to the position shown in FIG. 5F. As another merely illustrative example, instrument (10) may be advanced distally or proximally along longitudinal axis (130) during the transition from the position shown in FIG. 5G to the position shown in FIG. 5H. Other suitable stages at which instrument (10) may be advanced distally or proximally will be apparent to those of ordinary skill in the art in view of the teachings herein. It should be understood that the distance of each incremental distal or proximal movement of instrument (10) during successive stitching cycles may be selected based on a desired stitch density along the length of the tissue being sutured. It should also be understood that, once stitching is complete, suture (60) may define a generally helical path through tissue layers (300, 302). Other suitable ways in which instrument (10) may be used will be apparent to those of ordinary skill in the art in view of the teachings herein.

As should be apparent to those of ordinary skill in the art, needle (50) of the present example orbits about longitudinal axis (140), which is offset from longitudinal axis (130) of shaft (100) in the present example. This may enable needle (50) to travel about an arc having a radius that is greater than the radius of a trocar through which shaft (100) is inserted. In other words, the circumferential path of needle (50) need not be limited to the circumference of the trocar through which shaft (100) is inserted when the orbital axis of needle (50) is offset from longitudinal axis (130) of shaft (100). Thus, the configuration of end effector (200) in the present example may permit a larger radius needle to be used, and larger stitches to be made, than what would be permitted if the orbital motion of needle (50) were centered about longitudinal axis (130) of shaft (100). In some other versions, needle (50) does move in an orbital fashion about longitudinal axis (130) of shaft (100). Surgical instrument (10) may be further operated in accordance with the teachings of U.S. patent application Ser. No. 13/295,203, entitled "Laparoscopic Suturing Instrument with Dual-Action Needle Graspers," filed Nov. 11, 2011, now U.S. Pat. No. 8,702,732 and/or U.S. patent application Ser. No. 13/295,210, entitled "Laparoscopic Suturing Instrument with Perpendicular Eccentric Needle Motion," filed Nov. 11, 2011, now U.S. Pat. No. 8,906,043, the disclosures of which are incorporated by reference herein.

IV. Exemplary Shaft

As noted above, surgical instrument (10) comprises a shaft (100) extending between handle assembly (400) and end effector (100). As shown in FIG. 6, shaft (100) comprises an outer tubular member encasing a pair of sheaths (240, 280) and drive shafts (244, 284). In the present example, a first sheath (240) and first drive shaft (244) extend from handle assembly (400) to first grasping arm (210). First drive shaft (244) is coaxial to and nested within first sheath (240). As noted above, sheath (240) is mechanically ground in the angular direction relative to shaft (100) and first grasping arm (210) via fins (226, 236) and slots (241, 242) described above. Accordingly, sheath (240) remains in a first position while first drive shaft (244) is rotatable therein. When first drive shaft (244) is rotated a first direction, jaws (220, 230) of first grasping arm (210) simultaneously translate away from each other, thereby allowing first grasping arm (210) to receive or catch needle (50). When first drive shaft (244) is rotated in the other direction, jaws (220, 230) of first grasping arm (210) simultaneously translate toward each other, thereby grasping needle (50) with first grasping arm (210).

A second sheath (280) and second drive shaft (284) extend from handle assembly (400) to second grasping arm (250). Second drive shaft (284) is coaxial to and nested within second sheath (280). In the present example, second sheath (280) is mechanically ground in the angular direction relative second grasping arm (250) via fins (266, 276) and slots (281, 282) described above; however, in the present example, second sheath (280) is rotatable relative to shaft (100). Accordingly, second sheath (280) is operable to rotate second grasping arm (250) relative to shaft (100) when second sheath (280) is rotated. In the present example, second drive shaft (284) is rotatable within and relative to second sheath (280). Thus, when second drive shaft (284) is rotated a first direction, jaws (260, 270) of second grasping arm (250) simultaneously translate away from each other, thereby allowing second grasping arm (250) to receive or catch needle (50). When second drive shaft (284) is rotated in the other direction, jaws (260, 270) of second grasping arm (250) simultaneously translate toward each other, thereby grasping needle (50) with second grasping arm (250). In some instances, second drive shaft (284) and second sheath (280) may be simultaneously rotated together relative to shaft (100) to maintain jaws (260, 270) in a substantially fixed longitudinal position while second grasping arm (250) is rotated about longitudinal axis (140).

In some versions, shaft (100), first sheath (240), and/or second sheath (280) may include one or more bushings along a corresponding longitudinal axis (130, 140) to support first sheath (240) and/or second sheath (280) while still permitting rotation of first sheath (240) and/or second sheath (280) relative to shaft (100). By way of example only, such bushings may comprise a plurality of thermoplastic parts disposed about first sheath (240) and/or second sheath (280) at predetermined longitudinal positions. In addition, or in the alternative, shaft (100) may include interiorly mounted bushings. Of course other features and/or components may be used instead of bushings, such as bearings, pillow blocks, etc.

It should be understood that the foregoing description of the mechanical linkage of handle assembly (400) to end effector (200) is merely exemplary and other components and/or assemblies will be apparent to one of ordinary skill in the art in view of the teachings herein. For example, drive shafts (244, 284) may comprise resilient or bendable drive shafts. In some versions, one or more motors or actuators may be situated proximal to end effector (200) and coupled to one or more of sheaths (240, 280) and/or drive shafts (244, 284) to effect rotation. In such a version, a rotational sensor (not shown) may be disposed within handle assembly (400) to transmit instructions to the one or more motors or actuators. Still other configurations will be apparent to one of ordinary skill in the art in view of the teachings herein.

V. Exemplary Handle Assemblies

To control the operation of end effector (200) and grasping arms (210, 250) in accordance with the operation described in reference to FIGS. 5A-5H, an assembly (or assemblies) needs to control the opening and/or closing of jaws (220, 230, 260, 270) as well as the rotation of second grasping arm (250) relative to shaft (100). In the present example, sheaths (240, 280) and drive shafts (244, 284) are operable to control the opening and/or closing of jaws (220, 230, 260, 270) and the rotation of second grasping arm (250). The rotation of sheaths (240, 280) and/or drive shafts (244, 284) are controlled via handle assembly (400). In some versions, it may be desirable to control the rotation of sheaths (240, 280) and/or drive shafts (244, 284) through a single actuation assembly, such as a rack. Accordingly, various exemplary control assemblies that may be used with handle assembly (400) will now be discussed, while other examples will be apparent to those of ordinary skill in the art in view of the teachings herein.

A. Exemplary Rack Actuation Assembly

Figure 7:
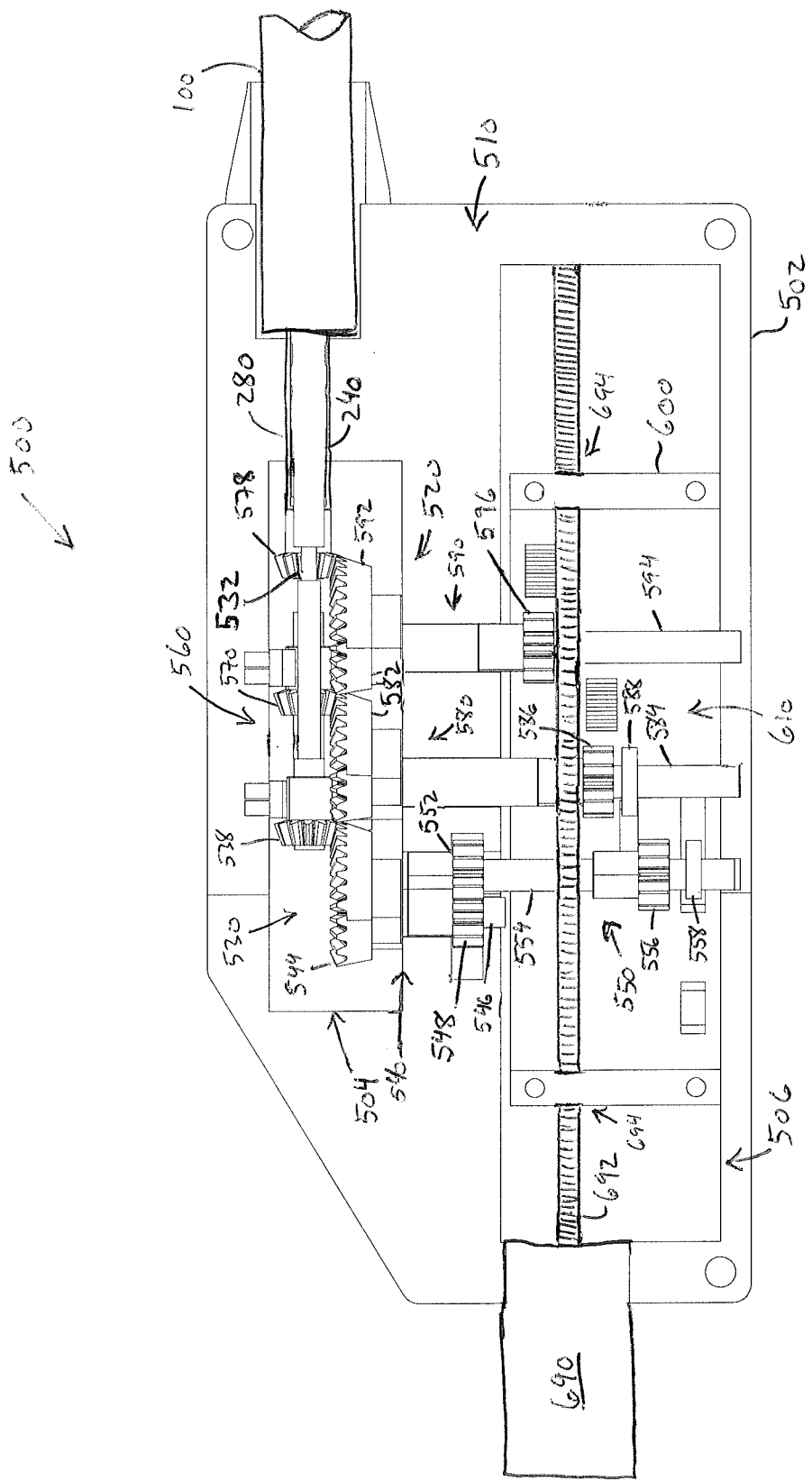
FIG. 7 depicts a side elevation view of an exemplary handle assembly having a portion of a casing removed to show an exemplary rack actuation assembly.

FIGS. 7-11F depict an exemplary handle assembly (500) having an exemplary rack actuation assembly (510) therein. Rack actuation assembly (510) is operable to control grasping arms (210, 250) in accordance with the operations described above in reference to FIGS. 5A-5H. As shown in FIG. 7, handle assembly (500) includes a casing (502) that may be gripped by a user and that accommodates rack actuation assembly (510). A motor (690) is operatively coupled to rack actuation assembly (510) such that motor (690) controls grasping arms (210, 250), as will be described in greater detail below. It should be understood, however, that motor (690) is merely optional. Shaft (100) is rotationally fixed to casing (502) and extends distally therefrom. As noted above, shaft (100) encases sheaths (240, 280) and drive shafts (244, 284) and provides a mechanical ground relative to sheaths (240, 280) and drive shafts (244, 284). In the present example, second sheath (280) and drive shafts (244, 284) extend proximally from shaft (100) and into a transfer section (504) of casing (502) to engage with a transfer assembly (520) of rack actuation assembly (510), as will be described in greater detail below. Casing (502) is subdivided into a transfer section (504) and a rack section (506), though this is merely optional. Rack actuation assembly (510) is likewise subdivided into a transfer assembly (520) and a rack (600). Transfer assembly (520) is located within transfer section (504) and rack (600) is located within rack section (506).

i. Exemplary Transfer Assembly

Transfer assembly (520) is operable to rotate in response to the control features (610) of rack (600) such that second sheath (280) and drive shafts (244, 284) rotate to control the movement of grasping arms (210, 250) of end effector (200). As will be described in greater detail below, transfer section (504) houses a plurality of bevel gears (538, 544, 570, 578, 582, 592) of transfer assembly (520) such that rotational control from rack (600), spur gears (556, 586, 596), cams (558, 588, 598), rack gears (612, 614, 616, 618, 6120, 622), and cam surfaces (624, 626, 628, 630) is transferred to second sheath (280) and/or drive shafts (244, 284). It should be understood that in the present example first sheath (240) is rotationally fixed relative to shaft (100) and does not extend into transfer section (504), though this is merely optional. For instance, in some versions first sheath (240) also extends proximally into transfer section (504) and may be controlled by rack (600) in a similar manner to second sheath (280). In addition, in some versions, shaft (100) may not be fixed relative to casing (502), but may instead also be rotationally controlled via rack (600) as well. For instance, a distal end of shaft (100) may include gear teeth disposed about an outer surface of shaft (100). The gear teeth may mesh with a spur gear and drive shaft assembly such that the rotation of shaft (100) may also be controlled by rack (600). Of course still further configurations will be apparent to one of ordinary skill in the art in view of the teachings herein.

Figure 8:
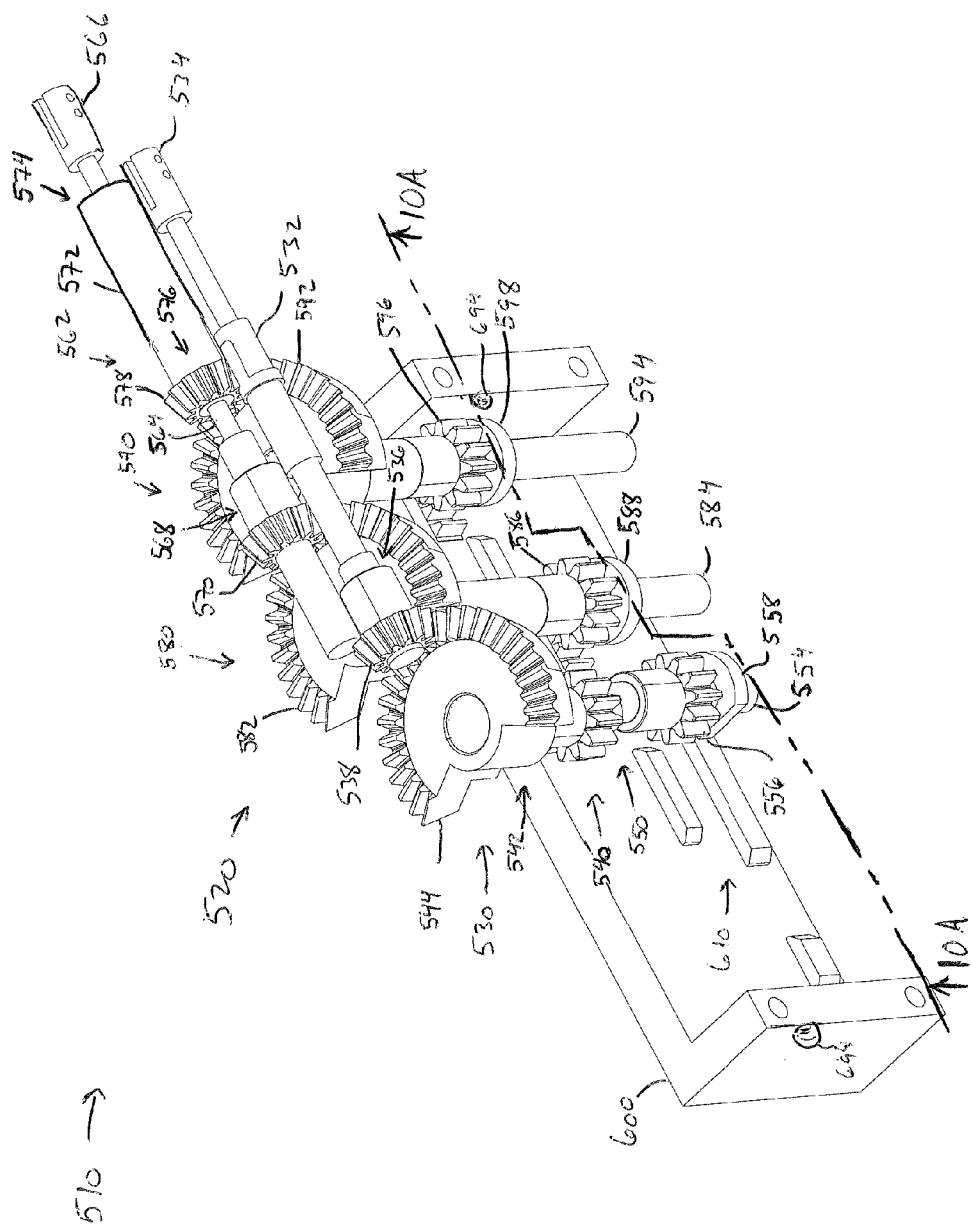
FIG. 8 depicts a perspective view of the rack actuation assembly of FIG. 7.

As shown in FIG. 7-8, transfer assembly (520) of the present example comprises a first grasping arm control assembly (530) and a second grasping arm control assembly (560). In the present example, first grasping arm control assembly (530) comprises a first transfer shaft (532) and a first transfer assembly member (540). In the present example, first transfer shaft (532) is rotationally coupled at a distal end (534) to first drive shaft (244) and engages with a first transfer assembly member (540) at a proximal end (536). By way of example only, first transfer shaft (532) may be coupled to first drive shaft (244) via transverse pins, threading, spline features, adhesives, and/or any other feature as will be apparent to one of ordinary skill in the art in view of the teachings herein. First transfer shaft (532) engages first transfer assembly member (540) at proximal end (536) via a first bevel gear (538) coupled to first transfer shaft (532).

First transfer assembly member (540) comprises a main assembly (542) and an offset assembly (550). In the present example, main assembly (542) comprises a second bevel gear (544) mounted to a first end of a shaft (546) and a spur gear (548) mounted to a second end of shaft (546). Second bevel gear (544) is configured to engage with first bevel gear (538) such that rotation of main assembly (542) rotates first drive shaft (244). In the example shown, second bevel gear (544) comprises a cut-out sector to reduce the longitudinal dimension of transfer assembly (520), though this is merely optional. Offset assembly (550) comprises a spur gear (552) mounted to a first end of a first shaft (554), a first spur gear (556) mounted to first shaft (554), and a first cam (558) mounted to first shaft (554). As will be described in greater detail below in reference to rack (600), first spur gear (556) and first cam (558) engage control features (610) of rack (600) such that the rotation of first grasping arm control assembly (530) (and therefore the opening and closing of jaws (220, 230) of first grasping arm (210)) is controlled by rack (600). As shown in FIG. 8, offset assembly (550) is positioned to be coplanar to second and third shafts (584, 594) of second grasping arm control assembly (560) described below. In the present example, although first transfer assembly member (540) lies in a plane that is offset from the plane containing second and third transfer assemblies (580, 590), offset assembly (550) is provided such that a single rack (600) can control all three transfer assembly members (540, 580, 590) as rack (600) moves longitudinally. Of course still further configurations for first grasping arm control assembly (530) will be apparent to one of ordinary skill in the art in view of the teachings herein. For instance, in versions where first sheath (240) is rotatable, first grasping arm control assembly (530) may further include another transfer assembly that is substantially similar to first transfer assembly member (540).

Second grasping arm control assembly (560) comprises a second transfer shaft (562), a second transfer assembly member (580), and a third transfer assembly member (590). In the present example, second transfer shaft (562) comprises an interior shaft (564) and an exterior sheath (572). Interior shaft (564) is rotationally coupled at a distal end (566) to second drive shaft (284) and engages with a second transfer assembly member (580) at a proximal end (568). By way of example only, interior shaft (564) may be coupled to second drive shaft (284) via transverse pins, threading, spline features, adhesives, and/or any other feature as will be apparent to one of ordinary skill in the art in view of the teachings herein. Interior shaft (564) engages second transfer assembly member (580) at proximal end (568) via a third bevel gear (570) coupled to interior shaft (564). Similarly, exterior sheath (572) is rotationally coupled at a distal end (574) to second sheath (280) and engages with a third transfer assembly member (590) at a proximal end (576). By way of example only, exterior sheath (572) may be coupled to second sheath (280) via transverse pins, threading, spline features, adhesives, and/or any other feature as will be apparent to one of ordinary skill in the art in view of the teachings herein. Exterior sheath (572) engages third transfer assembly member (590) at proximal end (576) via a fifth bevel gear (578) coupled to exterior sheath (572).

Second transfer assembly member (580) comprises a fourth bevel gear (582) mounted to a first end of a second shaft (584), a second spur gear (586) mounted to second shaft (584), and a second cam (588) mounted to second shaft (584). Fourth bevel gear (582) is configured to engage with third bevel gear (570) such that rotation of second transfer assembly member (580) rotates second drive shaft (284). In the example shown, fourth bevel gear (582) comprises a cut-out sector to reduce the longitudinal dimension of transfer assembly (520), though this is merely optional. As will be described in greater detail below in reference to rack (600), second spur gear (586) and second cam (588) engage control features (610) of rack (600) such that the rotation of second grasping arm control assembly (560) (and therefore the opening and closing of jaws (260, 270) of second grasping arm (250)) is controlled by rack (600).

Third transfer assembly member (590) comprises a sixth bevel gear (592) mounted to a first end of a third shaft (594), a third spur gear (596) mounted to third shaft (594), and a third cam (598) mounted to third shaft (594). Sixth bevel gear (592) is configured to engage with fifth bevel gear (578) such that rotation of third transfer assembly member (590) rotates second sheath (280). In the example shown, sixth bevel gear (592) comprises a cut-out sector to reduce the longitudinal dimension of transfer assembly (520), though this is merely optional. As will be described in greater detail below in reference to rack (600), third spur gear (596) and third cam (598) engage control features (610) of rack (600) such that the rotation of second grasping arm control assembly (560) (and therefore the rotation of second grasping arm (250)) is controlled by rack (600). Of course still further configurations for second grasping arm control assembly (560) will be apparent to one of ordinary skill in the art in view of the teachings herein.

In the present example, shafts (532, 546, 554, 562, 584, 594) are rotatably mounted within casing (502) such that shafts (532, 546, 554, 562, 584, 594) may rotate relative to casing (502). In some versions, shafts (532, 546, 554, 562, 584, 594) may include one or more bushings to support shafts (532, 546, 554, 562, 584, 594) relative to casing (502) while still permitting rotation. By way of example only, such bushings may comprise a plurality of thermoplastic parts disposed about shafts (532, 546, 554, 562, 584, 594) at predetermined positions. Of course other features and/or components may be used instead of bushings, such as bearings, pillow blocks, etc.

Still further configurations for transfer assembly (520) will be apparent to one of ordinary skill in the art in view of the teachings herein.

ii. Exemplary Rack

Referring back to FIG. 7, exemplary rack (600) is longitudinally actuatable within rack portion (506) of casing (502). Motor (690) is coupled to a proximal end of casing (502) and is coupled to a worm gear (692) that extends longitudinally through a rack section (506) of casing (502) and rack (600). Rack (600) includes a pair of threaded portions (694) that engage worm gear (692) such that rack (600) is longitudinally translatable when worm gear (692) is rotated by motor (690). It should be understood that in the present example, rack portion (506) of casing (502) prevents rack (600) from merely rotating about worm gear (692). Accordingly, motor (690) and worm gear (692) are operable to translate rack (600) longitudinally within rack section (506) such that control features (610) of rack (600) are operable to control the rotation of second sheath (280) and drive shafts (244, 284). In some other versions, motor (690) and/or worm gear (692) are omitted. For instance, rack (600) may be translated manually in some versions (e.g., using an integral slider grip or other feature). It should also be understood that detents and/or other features may be provided to produce audible and/or tactile feedback to indicate completion of each operational stage and/or at the end of motion for rack (600). Still other suitable features and configurations will be apparent to one of ordinary skill in the art in view of the teachings herein.

Figure 9:
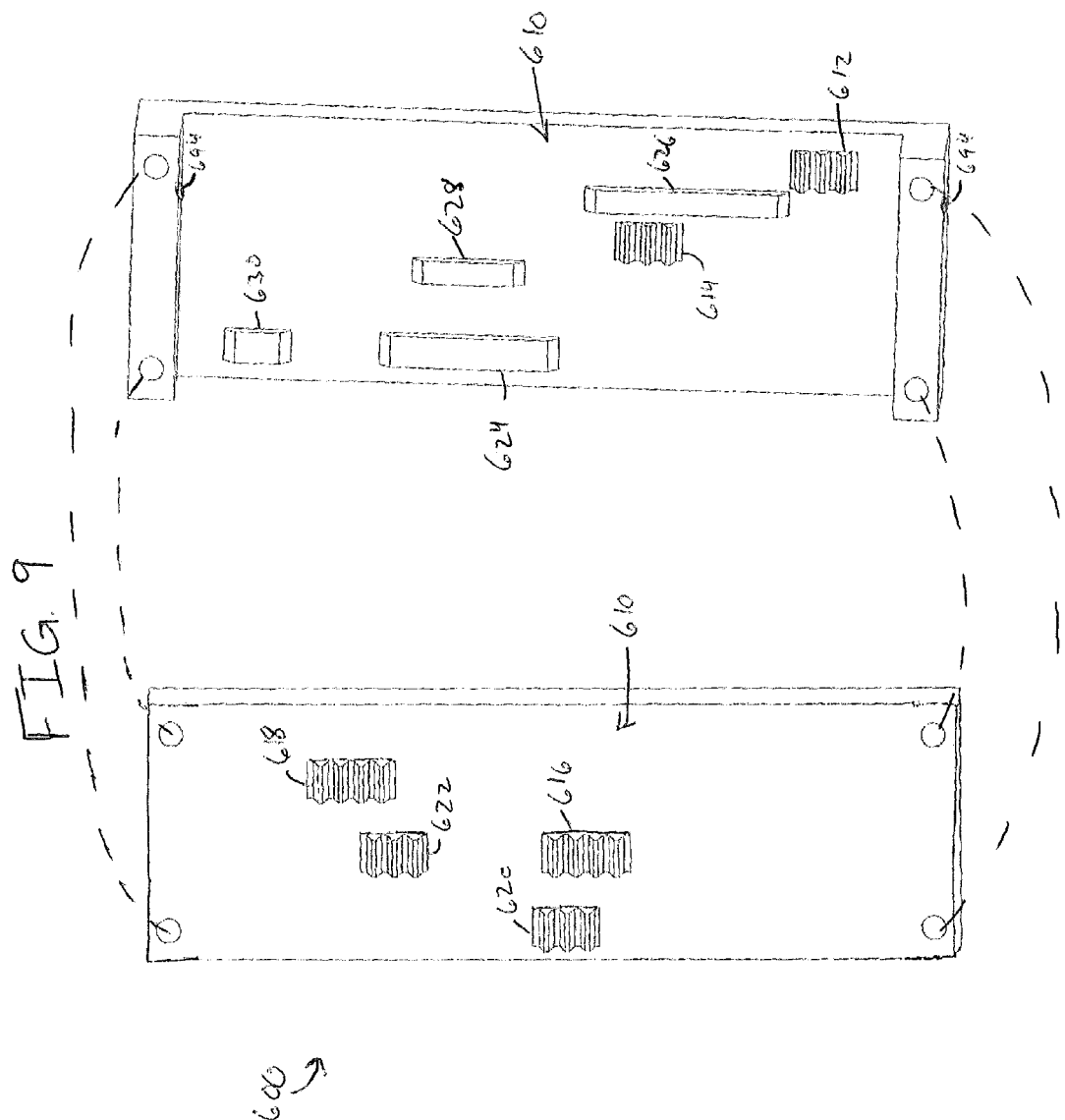
FIG. 9 depicts a perspective view of an exemplary rack of the rack actuation assembly of FIG. 7, with rack portions separated from each other.

As shown best in FIG. 9, rack (600) of the present example comprises a two-piece assembly having a plurality of control features (610) that engage with spur gears (556, 586, 596) and cams (558, 588, 598) of transfer assemblies (540, 580, 590) to control the rotational motion of second sheath (280) and drive shafts (244, 284). Control features (610) may be integrally formed with rack (600) and/or may be fixedly coupled to rack (600). In the present example, control features (610) include a plurality of rack gears (612, 614, 616, 618, 620, 622) and cam surfaces (624, 626, 628, 630). Rack gears (612, 614, 616, 618, 620, 622) and cam surfaces (624, 626, 628, 630) are configured to engage with spur gears (556, 586, 596) and cams (558, 588, 598) of transfer assemblies (540, 580, 590) to control the rotational motion of second sheath (280) and drive shafts (244, 284). As will be discussed below in reference to FIGS. 10A-11F, rack gears (612, 614, 616, 618, 620, 622) and cam surfaces (624, 626, 628, 630) are positioned on rack (600) at locations such that a desired motion of second sheath (280) and/or drive shafts (244, 284) is obtained. As shown in FIGS. 7-8, each spur gear (556, 586, 596) and cam (558, 588, 598) is located at a different vertical height relative to one another such that each engages with a different portion of rack (600). In addition, as shown in FIGS. 9-11F, rack (600) is positioned on both sides of spur gears (556, 586, 596) and cams (558, 588, 598) such that control features (610) may be positioned on either side of spur gears (556, 586, 596) and cams (558, 588, 598) and rotate spur gears (556, 586, 596) and/or cams (558, 588, 598) in either direction. Of course the foregoing rack (600) and control features (610) are merely exemplary and other configurations and arrangements will be apparent to one of ordinary skill in the art in view of the teachings herein.

iii. Exemplary Operation of Rack Actuation Assembly

Figure 10A:
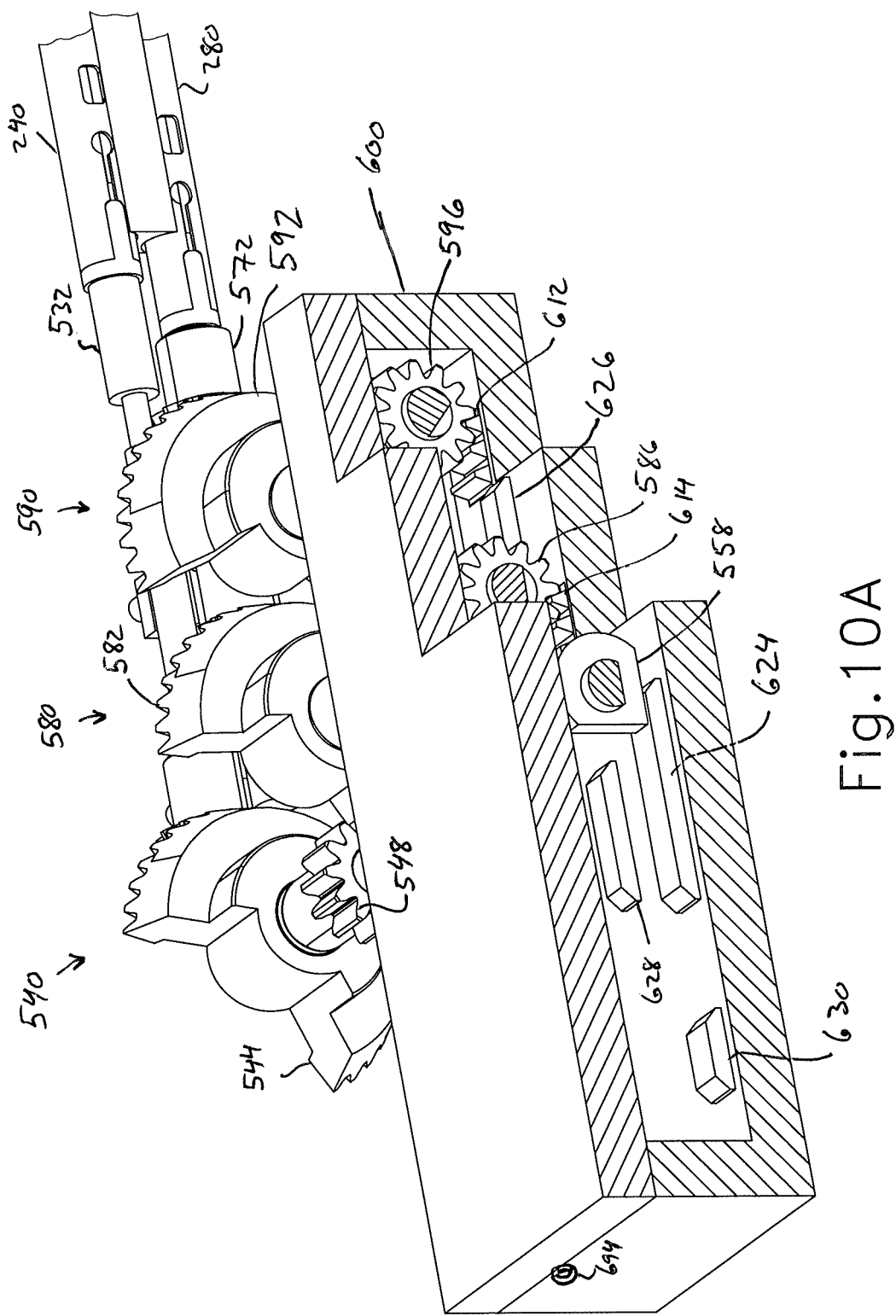
FIG. 10A depicts a perspective view of a tiered cross-section taken along section line 10A-10A in FIG. 8 showing the rack actuation assembly in a first position.

FIGS. 10A-11F depict perspective and multi-tiered cross-sectional views showing rack (600), rack gears (612, 614, 616, 618, 620, 622), cam surfaces (624, 626, 628, 630), spur gears (556, 586, 596), and cams (558, 588, 598) engaged at various positions during one longitudinal actuation of rack (600). FIGS. 10A and 11A generally depict an initial position of rack (600), rack gears (612, 614, 616, 618, 620, 622), cam surfaces (624, 626, 628, 630), spur gears (556, 586, 596), and cams (558, 588, 598) that corresponds to the position of end effector (200) shown in FIGS. 5A-5B. In this position, first grasping arm (210) has needle (50) grasped between jaws (220, 230) and second grasping arm (250) is pivoted away from first grasping arm (210) about longitudinal axis (140) with jaws (260, 270) initially in an open position. As specifically shown in FIG. 11A, first cam (558) is engaged with first cam surface (624) such that first transfer assembly member (540) is held substantially rotationally fixed. Accordingly, needle (50) is held within first grasping arm (210) and first drive shaft (244) is substantially prevented from rotating via the engagement of first cam (558) with first cam surface (624). In addition, first rack gear (612) is shown beginning to engage with third spur gear (596) and second rack gear (614) is shown beginning to engage with second spur gear (586).

Figure 10B:
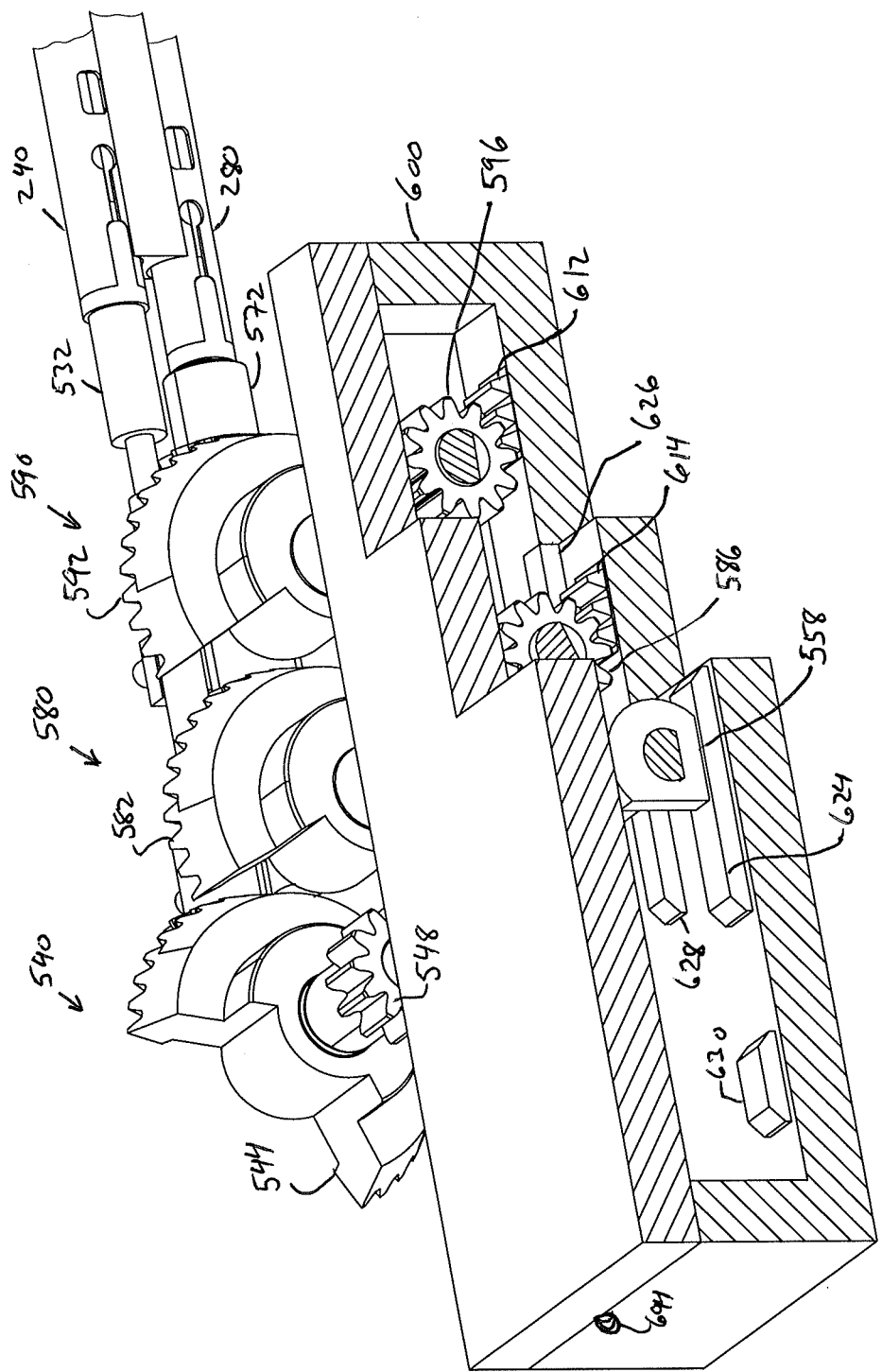
FIG. 10B depicts a perspective view of a tiered cross-section showing the rack actuation assembly of FIG. 10A advanced to a second position.
Figure 11A:
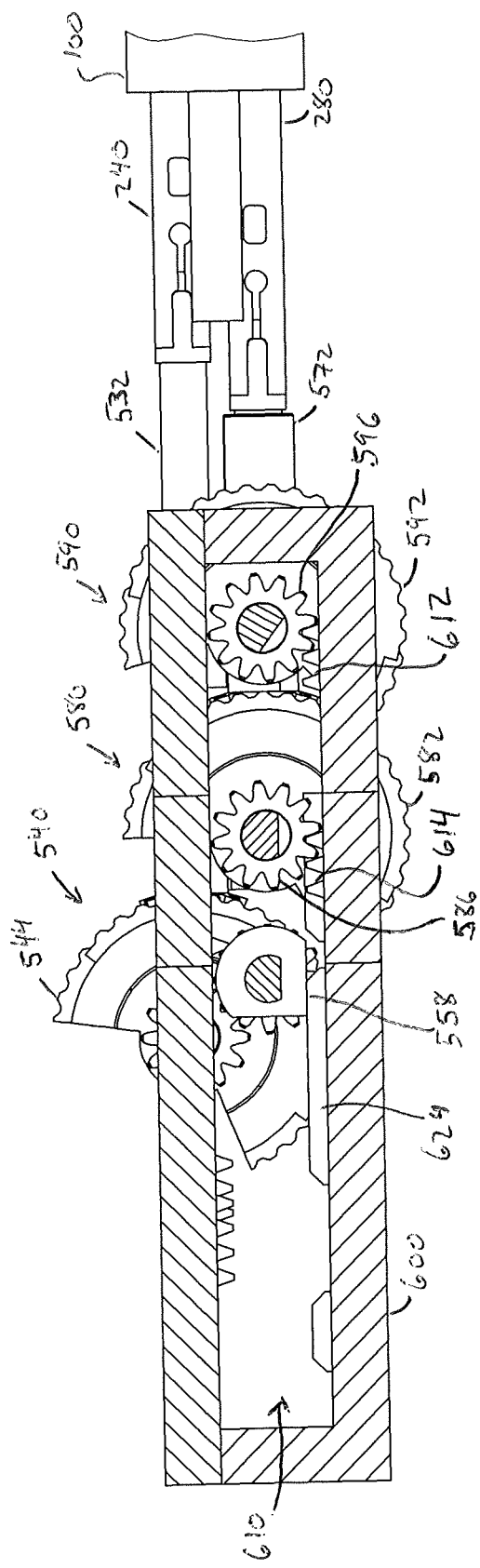
FIG. 11A depicts a tiered cross-sectional view of the rack actuation assembly of FIG. 10A showing the rack actuation assembly in the first position.
Figure 11B:
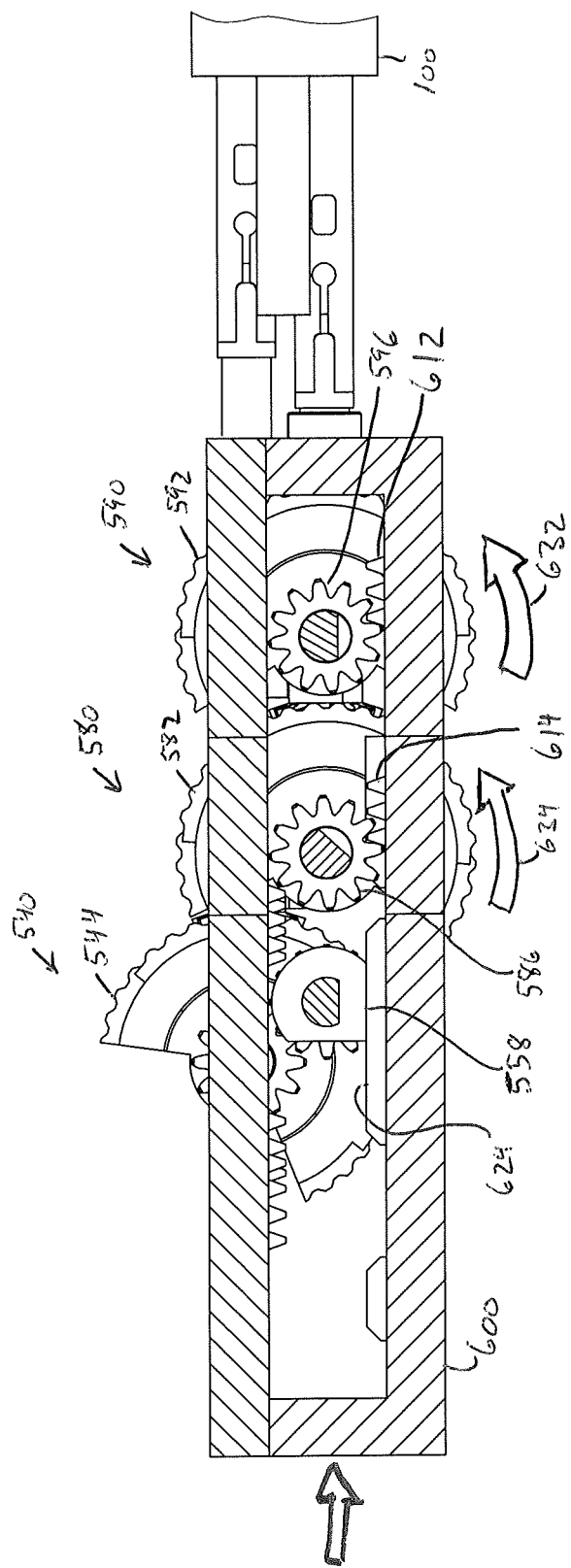
FIG. 11B depicts a tiered cross-sectional view of the rack actuation assembly of FIG. 10B showing the rack actuation assembly in the second position.

As rack is advanced distally by motor (690) and worm gear (692) to the position shown in FIGS. 10B and 11B, first rack gear (612) engages with third spur gear (596) and second rack gear (614) engages with second spur gear (586) to rotate third and second transfer assembly members (590, 580), respectively, in the direction of arrows (632, 634). As shown in FIG. 11B, rack gears (612, 614) are positioned to engage their corresponding spur gears (596, 586) substantially simultaneously. Accordingly, both second sheath (280) and second drive shaft (284) are substantially rotated together. As a result, second grasping arm (250) is pivoted about longitudinal axis (140) to the position shown in FIG. 5C. In addition, first cam (558) remains engaged and slides along first cam surface (624) such that needle (50) remains held within first grasping arm (210) and first drive shaft (244) remains substantially prevented from rotating via the engagement of first cam (558) with first cam surface (624).

Figure 10C:
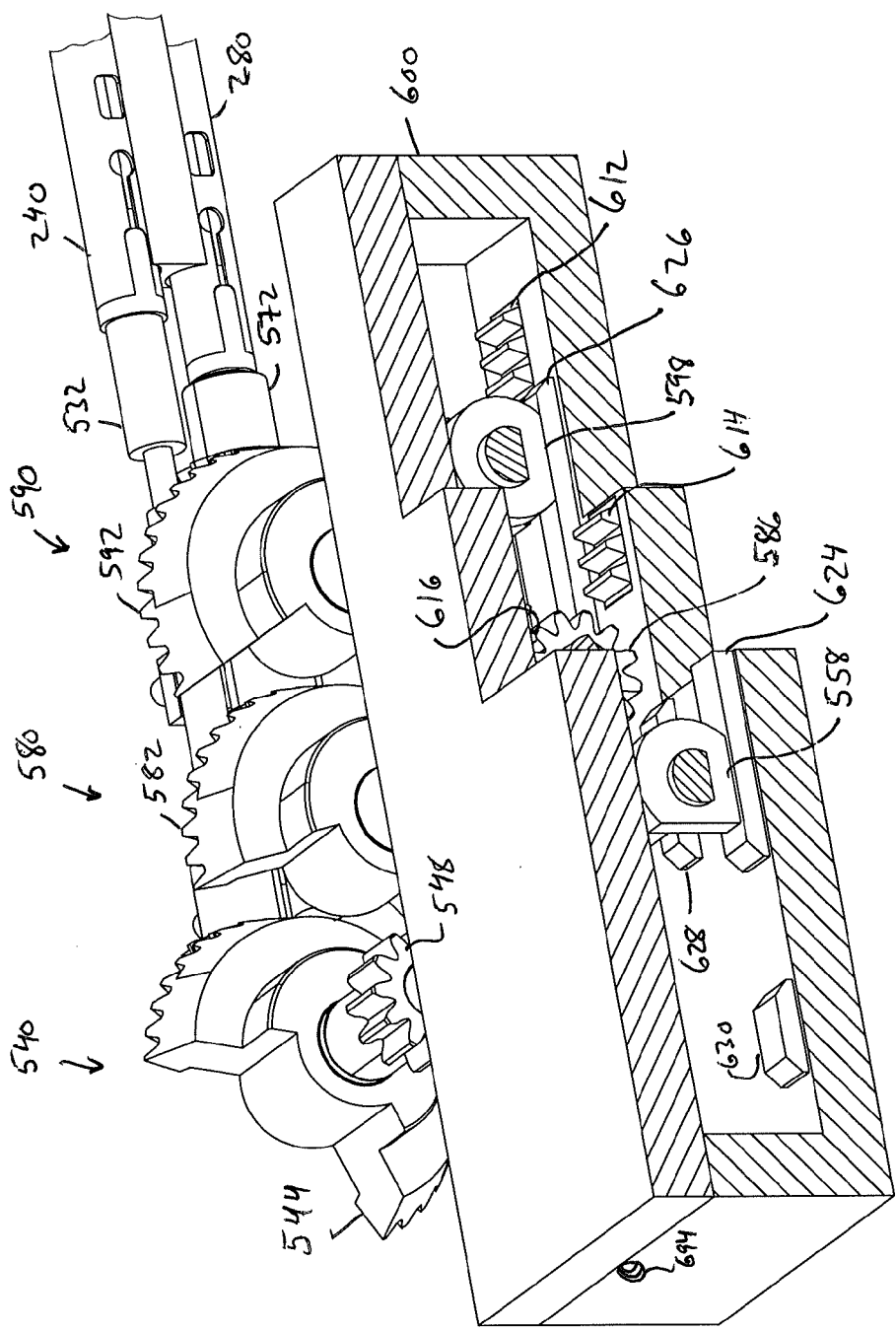
FIG. 10C depicts a perspective view of a tiered cross-section showing the rack actuation assembly of FIG. 10A advanced to a third position.
Figure 11C:
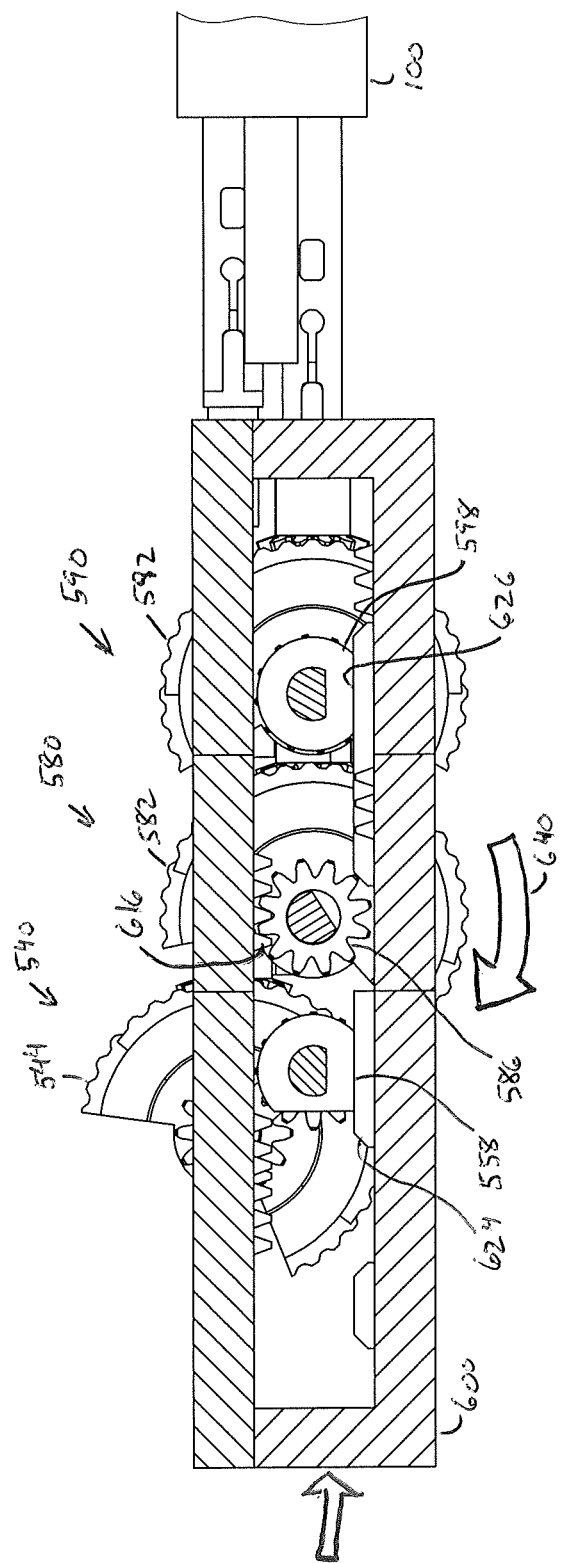
FIG. 11C depicts a tiered cross-sectional view of the rack actuation assembly of FIG. 10C showing the rack actuation assembly in the third position.

As rack (600) continues to advance distally to the position shown in FIGS. 10C and 11C, second spur gear (586) engages with third rack gear (616) to rotate second transfer assembly member (580) in the direction of arrow (640). As with the configuration shown in FIG. 11B, first cam (558) remains engaged and slides along first cam surface (624) such that needle (50) remains held within first grasping arm (210) and first drive shaft (244) remains substantially prevented from rotating via the engagement of first cam (558) with first cam surface (624). In addition, third cam (598) engages a second cam surface (626) such that third transfer assembly member (590) is held substantially rotationally fixed. As a result, second drive shaft (284) is rotated while second sheath (280) and first drive shaft (284) remain substantially rotationally fixed. Accordingly, jaws (260, 270) of second grasping arm (250) are driven toward each other by threaded sections (286, 288) to grasp needle (50) while the rotational position of second grasping arm (250) remains fixed in the position shown in FIG. 5C. Thus, in this position needle (50) is grasped by both first grasping arm (210) and second grasping arm (250).

Figure 10D:
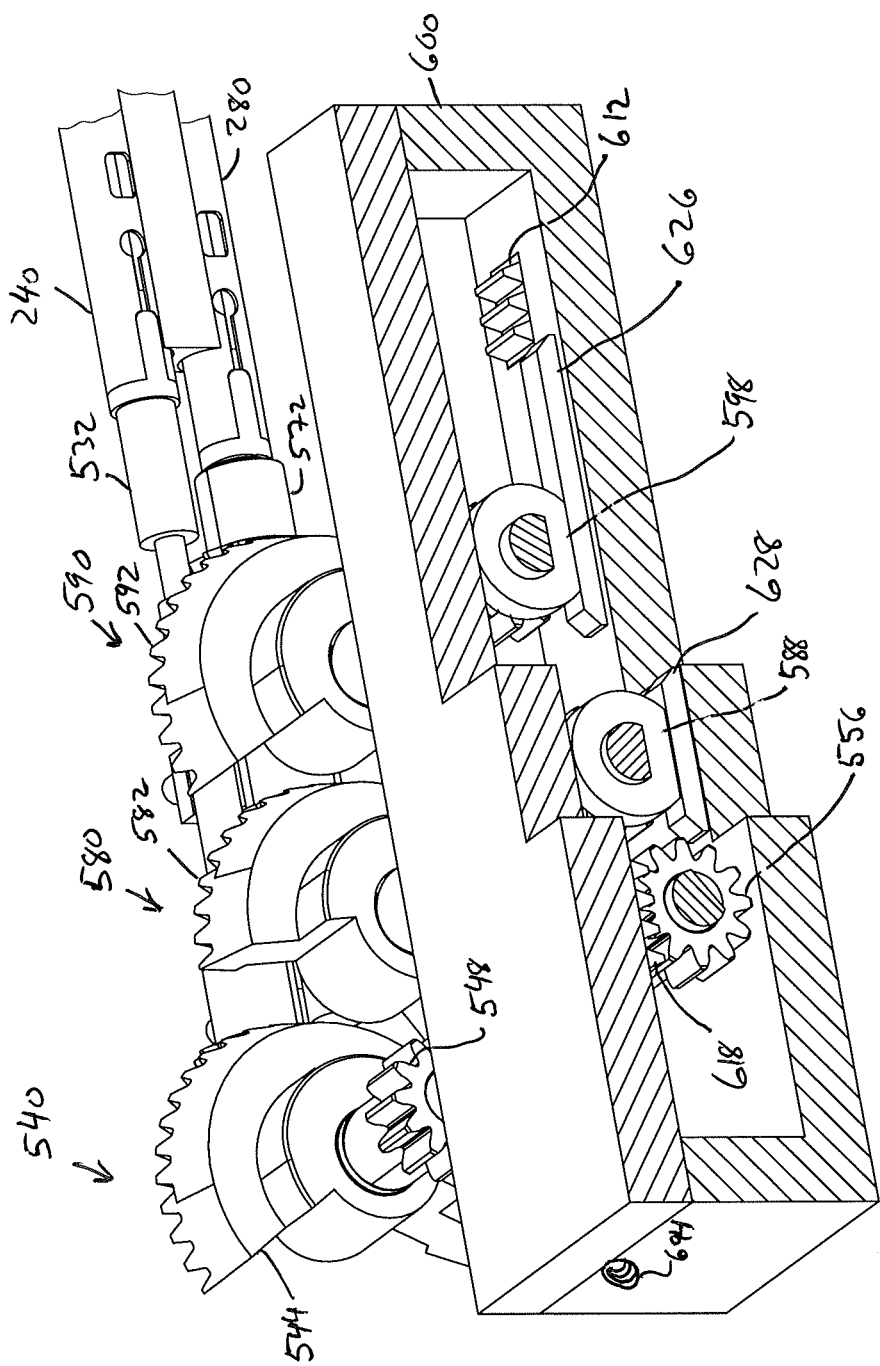
FIG. 10D depicts a perspective view of a tiered cross-section showing the rack actuation assembly of FIG. 10A advanced to a fourth position.
Figure 11D:
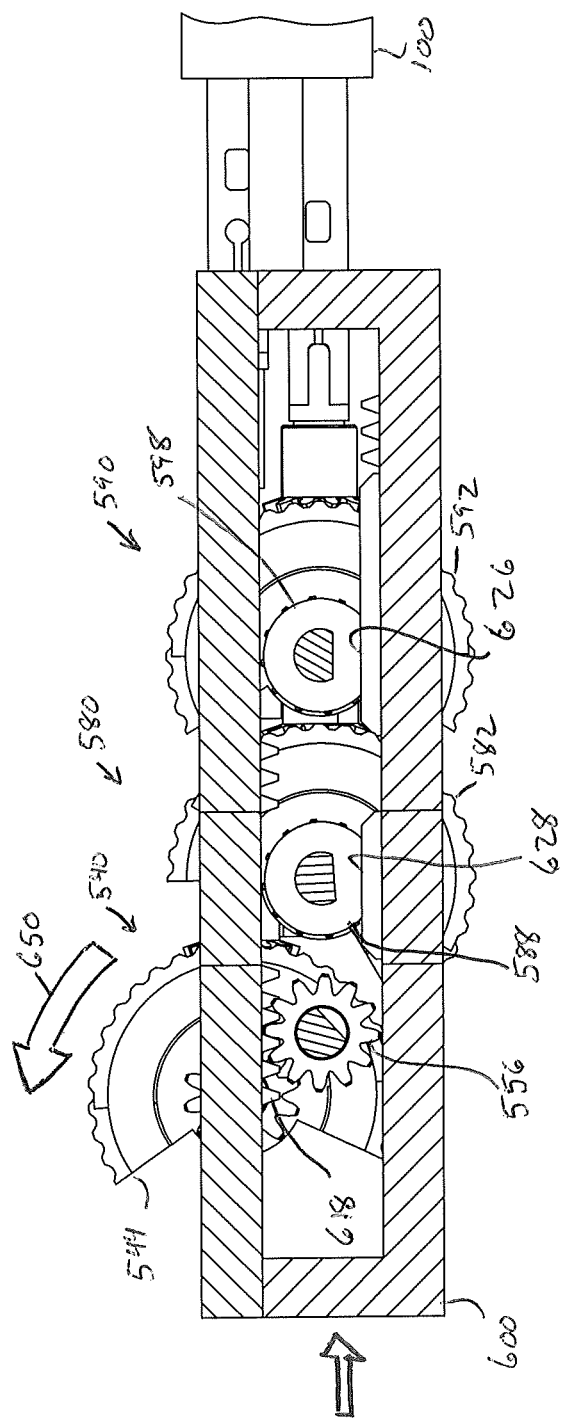
FIG. 11D depicts a tiered cross-sectional view of the rack actuation assembly of FIG. 10D showing the rack actuation assembly in the fourth position.

When rack (600) continues to advance distally, as shown in FIGS. 10D and 11D, first spur gear (556) engages with fourth rack gear (618) to rotate first transfer assembly member (540) in the direction of arrow (650). As a result of the rotation of first transfer assembly member (540), first drive shaft (244) is rotated such that jaws (220, 230) of first grasping member (210) are driven apart to release needle (50) from the grasp of first grasping member (210). In this position, third cam (598) remains engaged with second cam surface (626) such that third transfer assembly member (590) is held substantially rotationally fixed. In addition, second cam (588) engages a third cam surface (628) such that second transfer assembly member (580) is also held substantially rotationally fixed. Accordingly, both second sheath (280) and second drive shaft (284) remain substantially rotationally fixed while first drive shaft (244) causes first grasping arm (210) to release the grip of jaws (220, 230) on needle (50). Accordingly, control of needle (50) is fully transferred from first grasping arm (210) to second grasping arm (250) while second grasping arm (250) remains in the rotational position shown in FIG. 5C.

Figure 10E:
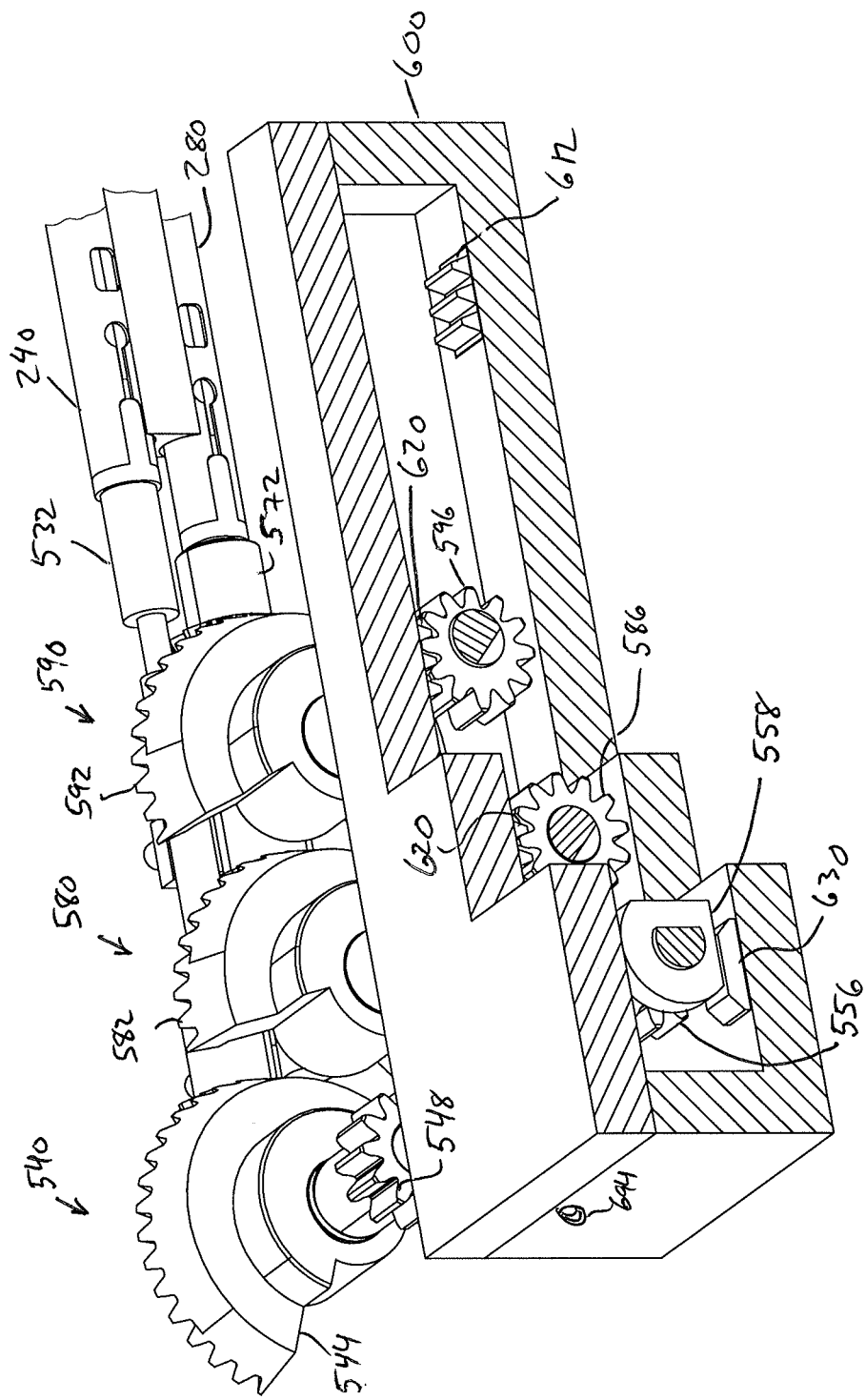
FIG. 10E depicts a perspective view of a tiered cross-section showing the rack actuation assembly of FIG. 10A advanced to a fifth position.
Figure 10F:
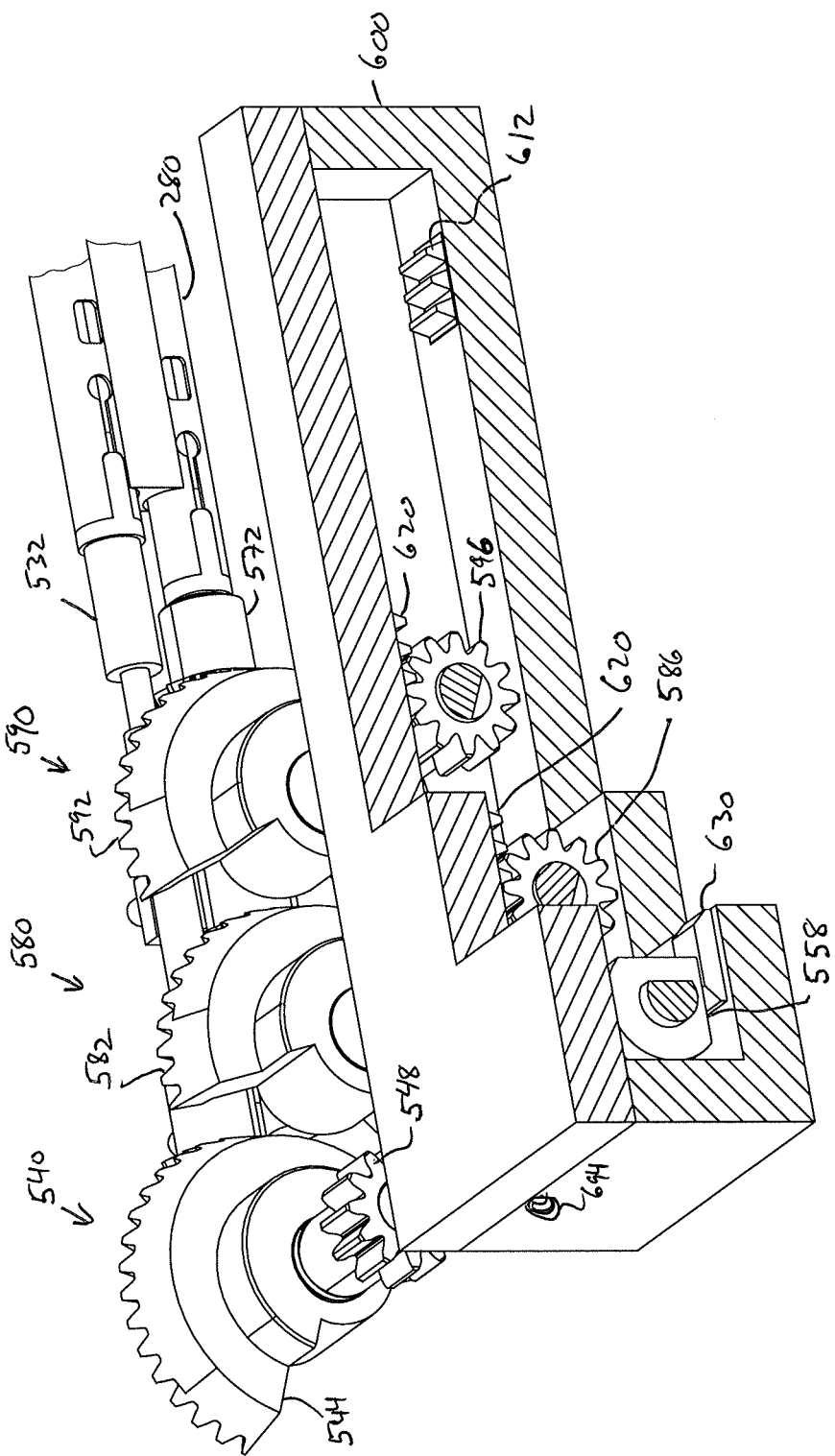
FIG. 10F depicts a perspective view of a tiered cross-section showing the rack actuation assembly of FIG. 10A advanced to a sixth position.
Figure 11E:
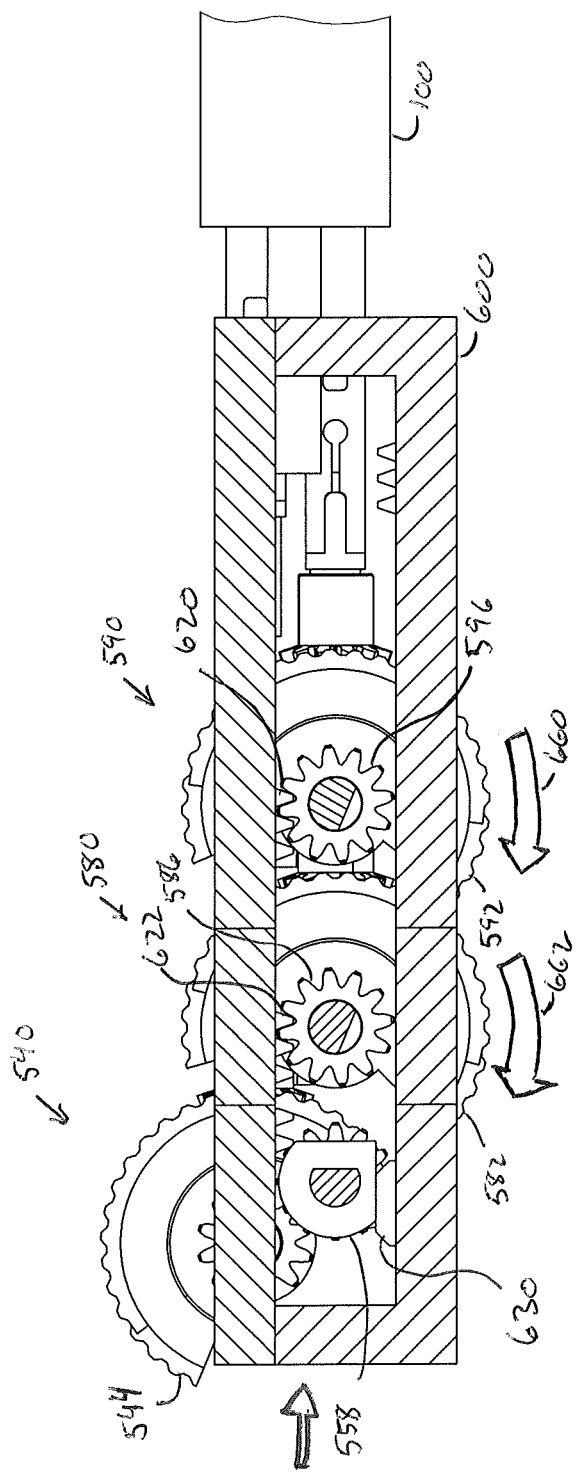
FIG. 11E depicts a tiered cross-sectional view of the rack actuation assembly of FIG. 10E showing the rack actuation assembly in the fifth position.
Figure 11F:
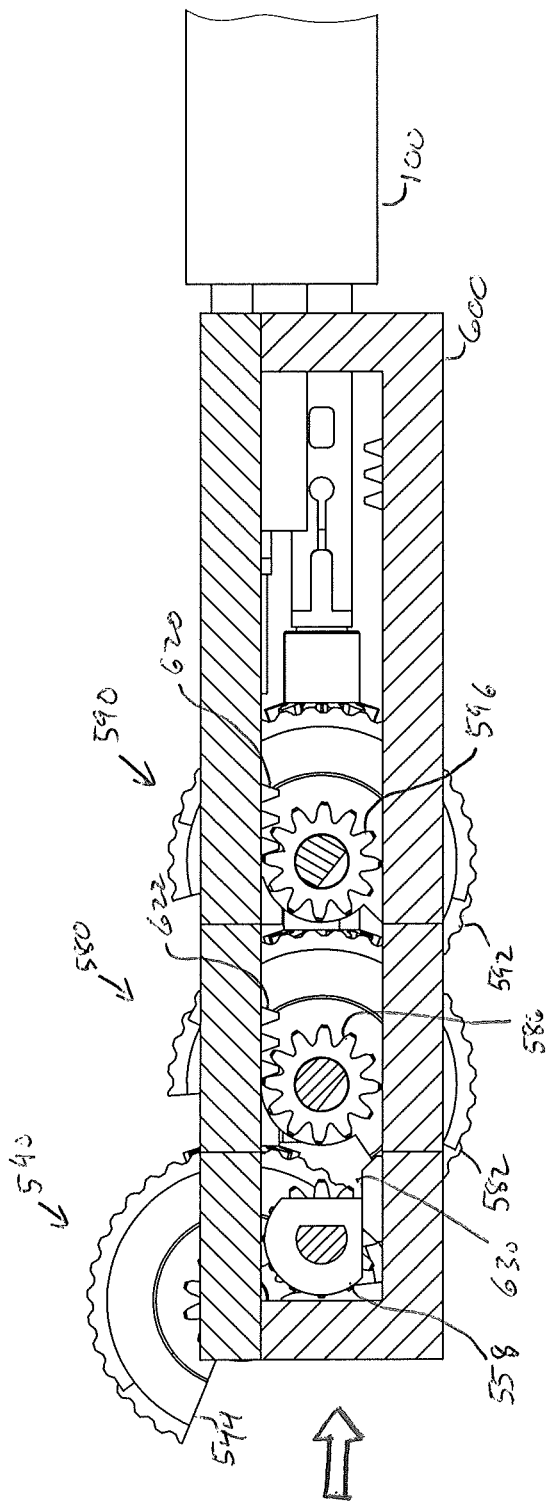
FIG. 11F depicts a tiered cross-sectional view of the rack actuation assembly of FIG. 10F showing the rack actuation assembly in the sixth position.

As rack (600) advances to the position shown in FIGS. 10E and 11E, fifth rack gear (620) engages with third spur gear (596) and sixth rack gear (622) engages with second spur gear (586) to rotate third and second transfer assembly members (590, 580), respectively, in the direction of arrows (660, 662). Rack gears (620, 622) are positioned to engage their corresponding spur gears (596, 586) substantially simultaneously. Accordingly, both second sheath (280) and second drive shaft (284) are substantially rotated together. As a result, second grasping arm (250) is pivoted about longitudinal axis (140) to the position shown in FIG. 5D. In addition, first cam (558) engages with and slides along fourth cam surface (630) such that first drive shaft (244) remains substantially prevented from rotating via the engagement of first cam (558) with fourth cam surface (630). Accordingly, jaws (220, 230) of first grasping arm (210) remain open to receive needle (50). FIGS. 10F and 11F depict a final position of rack (600) with third spur gear (596) and second spur gear (586) fully rotated by fifth rack gear (620) and sixth rack gear (622) to rotate second grasping arm (250) to the end position shown in FIG. 5D.

Rack (600) may then be actuated in the reverse direction to reverse the foregoing motions of grasping arms (210, 250) (e.g., to transition arms (210, 250) from the stage shown in FIG. 5E to the stage shown in FIG. 5F; then to the stage shown in FIG. 5G). In addition, it should be understood that motor (690) may be stopped at any position, including those not shown in FIGS. 10A-11F, to halt or pause the motion of end effector (200). Of course still further configurations for rack (600) and/or arrangements for control features (610) will be apparent to one of ordinary skill in the art in view of the teachings herein.

For instance, in some versions transfer section (504), and/or transfer assembly (540) may be omitted and spur gears (556, 586, 596) and cams (558, 588, 598) may be directly coupled to and rotate second sheath (280) and/or drive shafts (244, 284). By way of example only, rack (600) may be vertically translatable via motor (690) and worm gear (692) relative to second sheath (280) and/or drive shafts (244, 284). In addition, while a motor (690) and worm gear (692) are included in the present example, it should be understood that rack (600) may be manually actuated via a lever or a handle coupled to worm gear (692).

Figure 12:
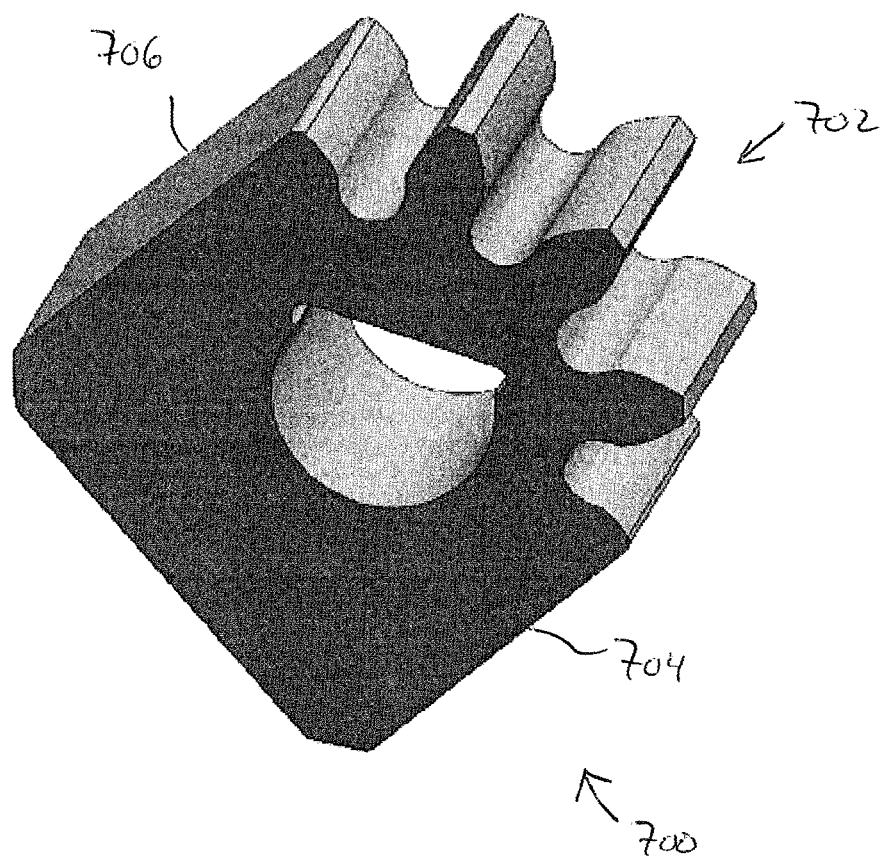
FIG. 12 depicts a perspective view of an exemplary hybrid gear.

In some versions, spur gears (556, 586, 596) and cams (558, 588, 598) may be combined into a single hybrid gear (700) shown in FIG. 12. Gear (700) comprises a spur gear portion (702) and one or more cam portions (704, 706). Accordingly, gear (700) may replace each combination of spur gears (556, 586, 596) and cams (558, 588, 598) for transfer assembly members (540, 580, 590). Accordingly, control features (610) of rack (600) may be reduced to a single linear line of control features (610) such that gear portion (702) engages rack gears (612, 614, 616, 618, 620, 622) and cam portions (704, 706) engage cam surfaces (624, 626, 628, 630) as rack (600) is actuated relative to gear (700). Of course it should be understood that gear (700) may comprise a plurality of gear portions (702) and cam portions (704, 706) in any arrangement, as will be apparent to one of ordinary skill in the art in view of the teachings herein.

Figure 13:
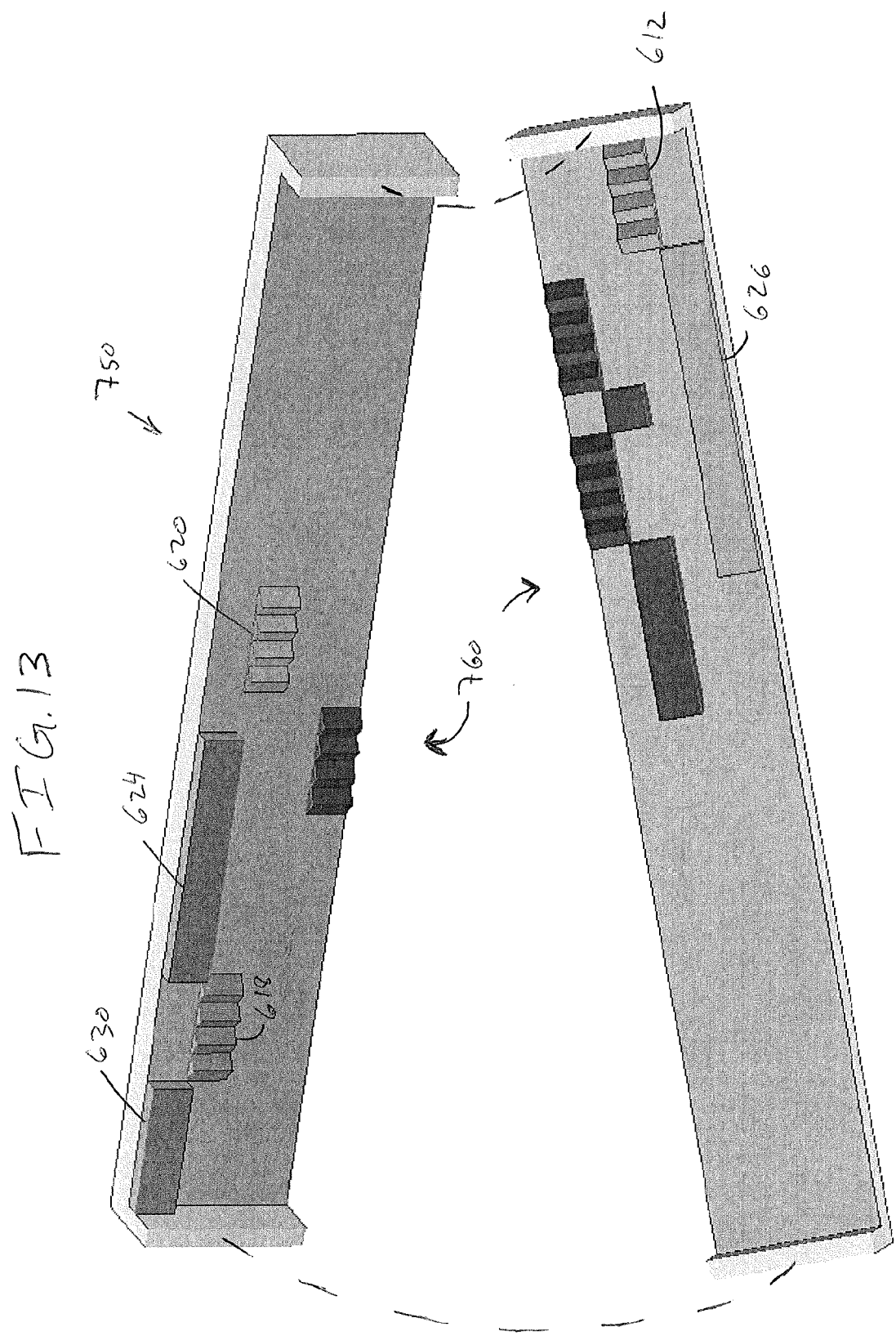
FIG. 13 depicts a perspective view of an exemplary alternative rack, with rack portions separated from each other.

In addition, or in the alternative, the foregoing assemblies may be used with an alternative rack (750) shown in FIG. 13. Rack (750) comprises a two-tiered rack having control features (760) positioned such that the spur gears (556, 586, 596) and cams (558, 588, 598) for two transfer assembly members (540, 580, 590) are at the same vertical level. It should be understood that the shafts (554, 584, 594) of these two transfer assembly members (540, 580, 590) are sufficiently horizontally spaced such that control feature (760) may be positioned on the same vertical level. By way of example only, as shown in FIG. 13 rack gears (612, 620) and second cam surface (626) that engage third spur gear (596) and third cam (598) are shown on the same vertical level as fourth rack gear (618) and cam surfaces (624, 630) that engage first spur gear (556) and first cam (558). In yet a further version, all rack gears (612, 614, 616, 618, 620, 622)

may lie within the same vertical level and all cam surfaces (624, 626, 628, 630) may lie within the same vertical level such that a single longitudinally extending rack (600) may be used.

B. Exemplary Vertical Rack Assembly

Figure 14:
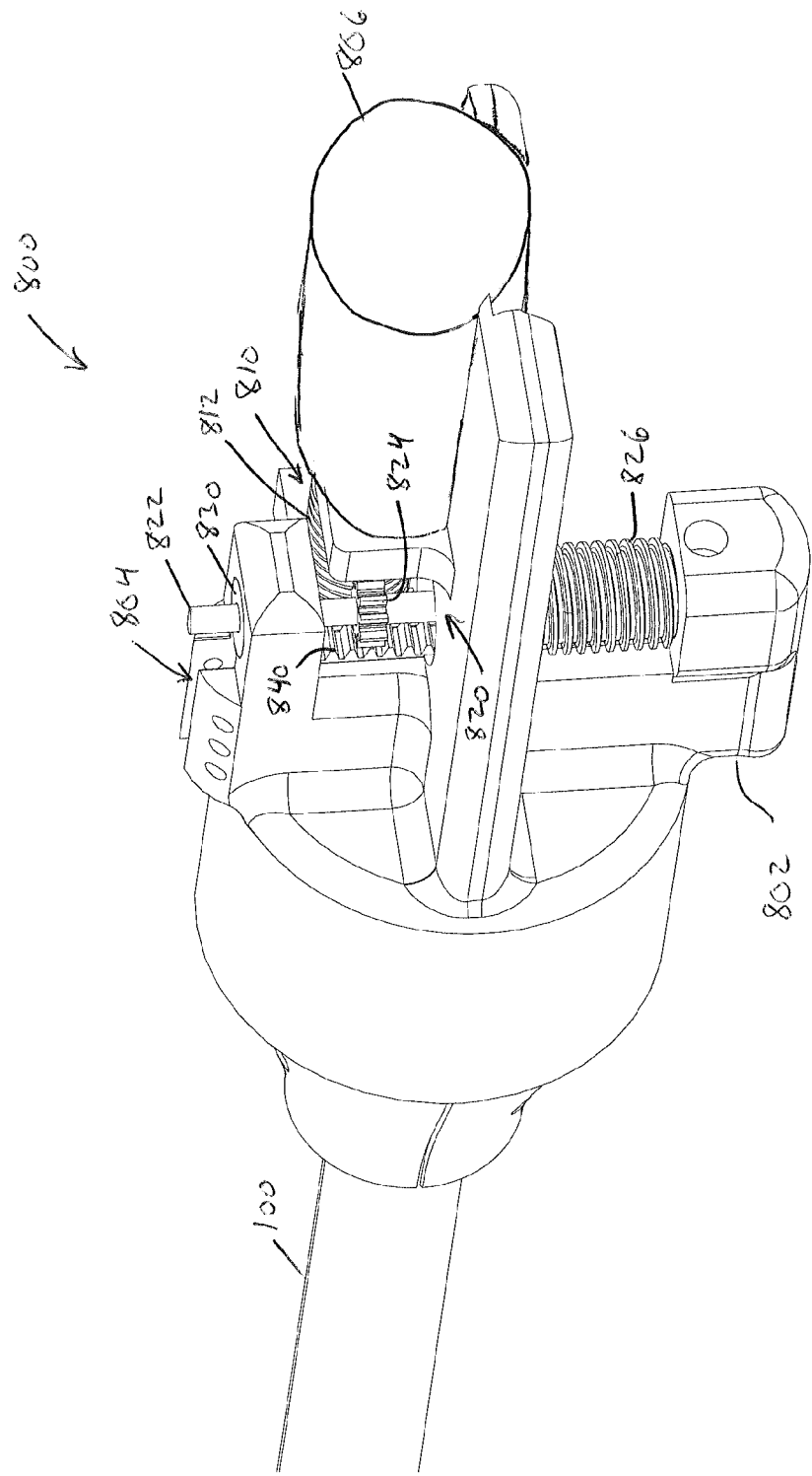
FIG. 14 depicts a perspective view of an exemplary vertical rack assembly.
Figure 15:
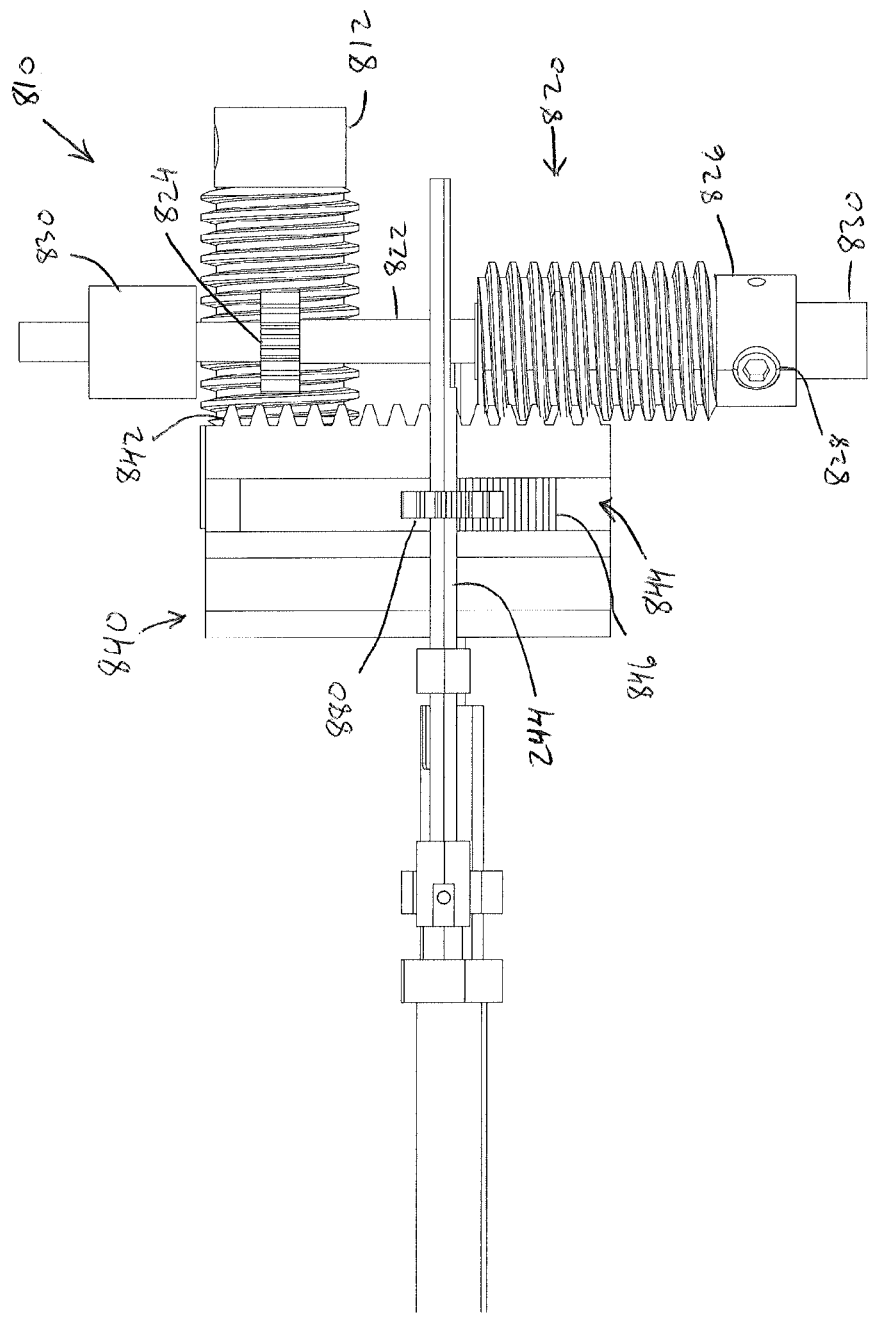
FIG. 15 depicts a first side elevation view of the vertical rack assembly of FIG. 14 omitting the frame.
Figure 16:
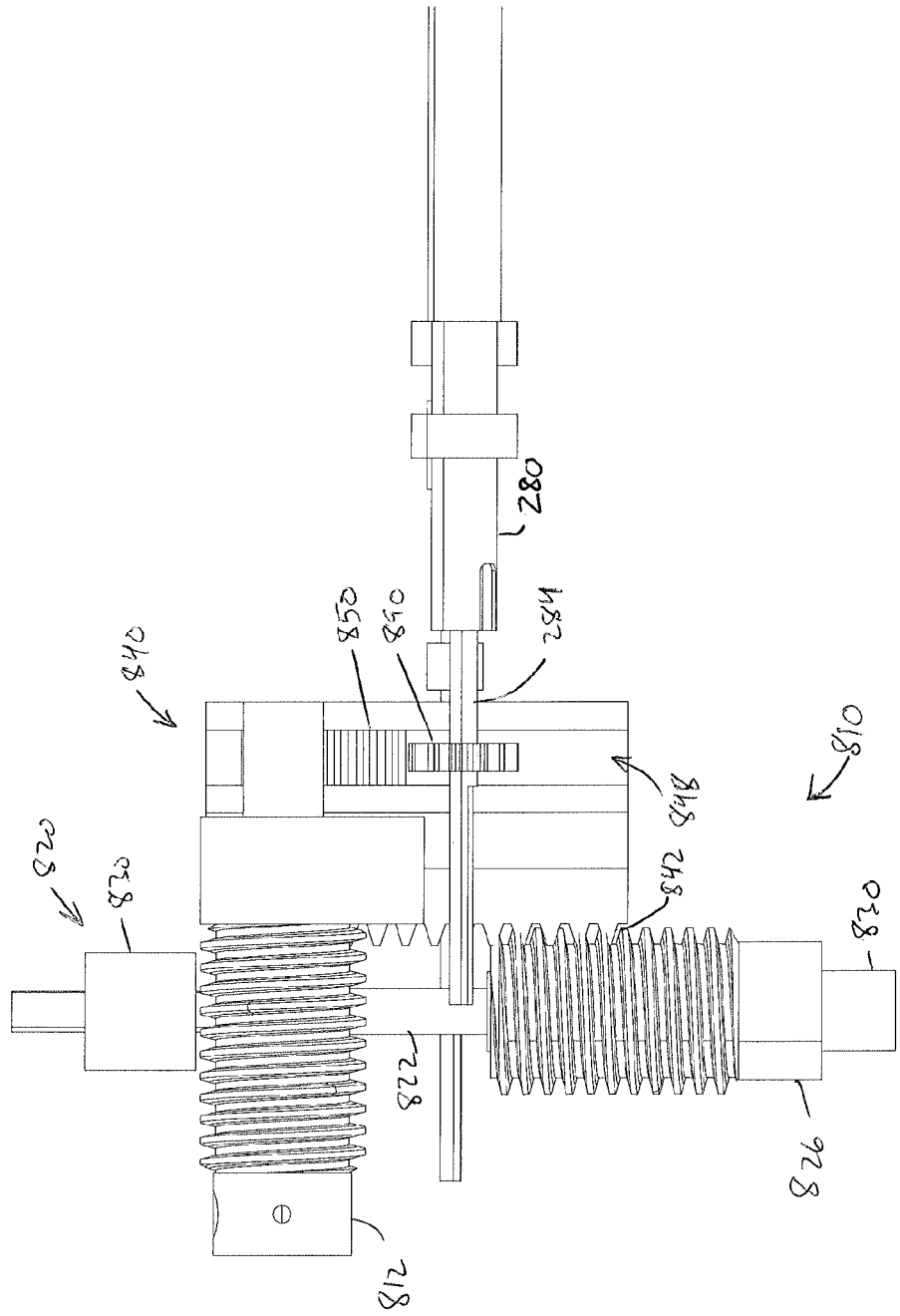
FIG. 16 depicts a second side elevation view of the vertical rack assembly of FIG. 14.

FIGS. 14-16 depict an exemplary vertical rack assembly (800) that is operable to control grasping arms (210, 250) in accordance with at least some of the operations described above in reference to FIGS. 5A-5H. In the present example, vertical rack assembly (800) comprises a frame (802) (shown in FIG. 13, but omitted from FIGS. 14-15), a motor (806), a transmission assembly (810), and a vertical rack (840). As shown in FIG. 14, shaft (100) is fixedly coupled to and extends distally from frame (802). Motor (806) is mounted to frame (802) and is operatively coupled to horizontal worm gear (812) of transmission assembly (810). Transmission assembly (810) is engaged with vertical rack (840) and is operable to vertically translate vertical rack (840) relative to frame (802). As shown in FIGS. 15-16, vertical rack (840) engages with first and second spur gears (880, 890) that are fixedly coupled to drive shafts (244, 284). Accordingly, when motor (806) operates transmission assembly (810) to actuate vertical rack (840), drive shafts (244, 284) rotate in opposing directions. As described above in reference to FIGS. 5B-5C, such motion of drive shafts (244, 284) is operable to transfer control of needle (50) from one grasping arm (210, 250) to the other grasping arm (210, 250). To transfer control back, motor (806) is reversed to actuate vertical rack (840) in the opposing direction. While the following example is described in reference to transferring control of needle (50) between grasping arms (210, 250), it should be understood that other racks, cam surfaces, and/or other control features for vertical rack (840) may be included to control the motion of other components. For example, rotation of shaft (100), second sheath (280), first sheath (240), etc.

Referring to FIGS. 15-16, transmission assembly (810) comprises a horizontal worm gear (812) and a vertical transfer shaft assembly (820) engaged with worm gear (812). Vertical transfer shaft assembly (820) comprises a shaft (822), a third spur gear (824) rotationally fixed to shaft (822), and a vertical worm gear (826) rotationally fixed to shaft (822). By way of example only, a set screw (828) couples vertical worm gear (826) to shaft (822), though this is merely optional. As shown in FIG. 14, vertical transfer shaft assembly (820) is rotatably mounted to frame (802) by bushings (830) such that vertical transfer shaft assembly (820) is rotatable relative to frame (802) while remaining vertically fixed relative to frame (802). Third spur gear (824) is engaged with horizontal worm gear (812) and is operable to rotate shaft (822) when horizontal worm gear (812) rotates via motor (806). Vertical worm gear (826) is engaged with outer teeth (842) of vertical rack (840) such that rotation of vertical worm gear (826) actuates vertical rack (840) relative to frame (802). Accordingly, when motor (806) is operated, transmission assembly (810) is operable to actuate vertical rack (840) relative to frame (802). It should be understood that in some versions vertical transfer shaft assembly (820) may be omitted and motor (806) may be operatively coupled to vertical worm gear (826). Still further configurations for transmission assembly (810) will be apparent to one of ordinary skill in the art in view of the teachings herein.

Vertical rack (840) of the present example comprises outer teeth (842), a first rack track (844) (shown in FIG. 15), and a second rack track (848) (shown in FIG. 16). As described above, outer teeth (842) engage with vertical worm gear (826) to actuate vertical rack (840) relative to frame (802). As shown in FIG. 14, vertical rack (840) is contained within a vertical recess (804) and is vertically supported by the engagement with vertical worm gear (826). As shown in FIG. 15, first rack track (844) extends vertically on a side of vertical rack (840). First rack track (844) of the present example comprises a recessed trough having a first rack gear (846) disposed therein. Such a trough permits first spur gear (880) to be partially enveloped within vertical rack (840) to reduce the width-wise dimension of vertical rack assembly (800). Likewise, as shown in FIG. 16, second rack track (848) extends vertically on an opposing side of vertical rack (840) that is opposite to the side with first rack track (844). Second rack track (848) includes a recessed trough having a second rack gear (850) disposed therein. Such a trough permits second spur gear (890) to also be partially enveloped within vertical rack (840) to reduce the width-wise dimension of vertical rack assembly (800).

In addition, first rack track (844) and second rack track (848) are longitudinally offset in the present example with second rack track (848) located distal of first rack track (844). First rack gear (846) and second rack gear (850) are positioned within first rack track (844) and second rack track (848), respectively, to engage first and second spur gears (880, 890) substantially consecutively. By way of example only, when vertical rack (840) is actuated upwardly, first rack gear (846) initially engages first spur gear (880) to rotate first drive shaft (244). Once first drive shaft (244) is fully rotated, an open region in both rack tracks (844, 848) provides a pause before second rack gear (846) engages second spur gear (890) to rotate second drive shaft (284). Accordingly, this gap may assist in ensuring that needle (50) is grasped by at least one grasping arm (210, 250) prior to other grasping arm (210, 250) releasing needle (50). Of course this is merely optional and other positions for first rack gear (844) and/or second rack gear (850) will be apparent to one of ordinary skill in the art in view of the teachings herein.

Still further configurations for vertical rack assembly (800) will be apparent to one of ordinary skill in the art in view of the teachings herein. For instance, in some versions, motor (806) may be omitted and vertical rack assembly (800) is manually operated. In other versions, vertical rack (840) may instead be longitudinally oriented with first and second drive shafts (244, 284). In such an arrangement, a transmission may be provided between rack (840) and spur gears (880, 890) to transfer the longitudinal motion of rack (840) to rotational motion for spur gears (880, 890). In yet a further configuration, transmission assembly (810) and vertical rack (840) may be omitted entirely and, instead, horizontal worm gear (816) coupled to motor (806) may directly engage helical gears coupled to first and second drive shafts (244, 284).

It should be understood that features of vertical rack assembly (800) may be combined with or used in lieu of features of rack actuation assembly (510) and vice-versa. For instance, control features (610) of rack (600) and/or rack (750) may be included on a vertical rack (840) that vertically translates between first grasping arm control assembly (540) and second grasping arm control assembly (560) to control the motion of second sheath (280), second drive shaft (284), and first drive shaft (244). In addition, or in the alternative, an additional set of rack teeth (not shown) may be included on vertical rack (840) to engage a spur gear (not shown) that is fixedly coupled to second sheath (280) (shown in FIG. 16). This additional set of rack teeth may be positioned to correspond with a second section of second rack gear (850)

such that both second drive shaft (284) and second sheath (280) rotate substantially simultaneously to cause second grasping arm (250) to rotate in the manner shown in FIGS. 5B-5D and 5F-5G. Still other configurations will be apparent to one of ordinary skill in the art in view of the teachings herein.

VI. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
   (a) a shaft, wherein the shaft has a distal end and a proximal end;
   (b) an end effector located at the distal end of the shaft, wherein the end effector comprises:
      i. a first needle grasping member, and
      ii. a second needle grasping member,
      wherein the first needle grasping member and second needle grasping member are each operable to grasp and release a needle; and
   (c) a handle assembly coupled to the proximal end of the shaft, wherein the handle assembly comprises:
      i. a casing, and
      ii. an actuatable control assembly at least partially slidably disposed within the casing, wherein the actuatable control assembly further comprises:
         A. an actuatable rack configured to linearly actuate along a linear path,
         B. at least one rack gear fixed to the actuatable rack,
      wherein the control assembly is operable to control the first needle grasping member or the second needle grasping member in response to actuation of the control assembly relative to the casing, wherein the control assembly is operable to grasp the needle with the second needle grasping member and release the needle from the first needle grasping member when the actuatable rack and the at least one rack gear are actuated along the linear path.

2. The apparatus of claim 1 wherein the rack comprises a plurality of control features.

3. The apparatus of claim 2 wherein the control features comprise cam surfaces.

4. The apparatus of claim 1 wherein the rack is coupled to a motor, wherein the motor is operable to actuate the rack relative to the casing.

5. The apparatus of claim 1 wherein the first needle grasping member comprises a first sheath and a first drive shaft, wherein the first drive shaft is operable to cause the first needle grasping member to grasp and release the needle in response to rotation of the first drive shaft, wherein the second needle grasping member comprises a second sheath and a second drive shaft, wherein the second drive shaft is operable to cause the second needle grasping member to grasp and release the needle in response to rotation of the second drive shaft, wherein the control assembly is operable to rotate the second drive shaft and the first drive shaft.

6. The apparatus of claim 5 wherein the control assembly comprises a vertically actuatable rack.

7. The apparatus of claim 6 wherein the first drive shaft is coupled to a first gear, wherein the second drive shaft is coupled to a second gear, wherein the vertically actuatable rack is operable to rotate the first gear and the second gear, wherein the first gear engages a first side of the vertically actuatable rack and wherein the second gear engages a second side of the vertically actuatable rack.

8. The apparatus of claim 5 wherein the control assembly further comprises a motor and a transmission assembly, wherein the motor is operatively coupled to the transmission assembly, wherein the transmission assembly is operable to actuate the vertically actuatable rack vertically relative to the shaft.

9. The apparatus of claim 5 wherein the control assembly comprises a transfer assembly and a rack, wherein the transfer assembly is operable to rotate the second drive shaft and the first drive shaft, and wherein the rack comprises a plurality of control features, wherein the control features selectively engage with the transfer assembly as the rack is actuated relative to the transfer assembly.

10. The apparatus of claim 9 wherein the transfer assembly is further operable to rotate the second sheath relative to the shaft.

11. The apparatus of claim 10 wherein the handle assembly further comprises a motor, wherein the motor is operable to longitudinally actuate the rack relative to the transfer assembly.

12. The apparatus of claim 9 wherein the control features positioned on the rack to engage the transfer assembly to sequentially rotate the second drive shaft and the first drive shaft.

13. The apparatus of claim 1 wherein the control assembly comprises a second gear having a toothed sector and a flat cam sector along an outer perimeter of the second gear.

14. An apparatus comprising:
(a) a shaft, wherein the shaft has a distal end and a proximal end;
(b) an end effector located at the distal end of the shaft;
(c) a drive shaft assembly coupled to the end effector and extending through the shaft to the proximal end of the shaft, wherein the drive shaft assembly comprises an inner drive shaft and an outer sheath, wherein the inner drive shaft and the outer sheath are each independently rotatable relative to the shaft; and
(d) a body assembly coupled to the proximal end of the shaft, the body assembly comprising a casing and an actuatable control assembly, wherein the control assembly comprises a cam surface and a gear, wherein the cam surface and the gear are configured to unitarily actuate along a linear path, wherein the control assembly is operable to control the rotation of the inner drive shaft and the outer sheath of the drive shaft assembly in a predetermined sequence in response to an actuation of the control assembly along the linear path within the casing.

15. The apparatus of claim 14 wherein the control assembly is operable to synchronously rotate the inner drive shaft and the outer sheath.

16. The apparatus of claim 14 wherein one of the inner drive shaft or the outer sheath is operable to provide linear motion to the end effector.

17. The apparatus of claim 16 the control assembly is operable to synchronously translate the inner drive shaft and the outer sheath.

18. An apparatus comprising:
(a) a shaft, wherein the shaft has a distal end and a proximal end;
(b) an end effector located at the distal end of the shaft, wherein the end effector comprises:
  i. a first needle grasping member comprising:
    A. a first jaw,
    B. a second jaw translatable relative to the first jaw,
    C. a first outer sheath supporting the first jaw and the second jaw, wherein the first outer sheath is fixedly coupled to the shaft, and
    D. a first drive shaft extending through the first outer sheath wherein the first drive shaft is rotatable relative to the first outer sheath,
  wherein the first drive shaft is operable to longitudinally actuate the first jaw and the second jaw to grasp a needle, and
  ii. a second needle grasping member comprising:
    A. a third jaw,
    B. a fourth jaw translatable relative to the third jaw,
    C. a second outer sheath supporting the third jaw and the fourth jaw, wherein the second outer sheath is rotatably coupled to the shaft, and
    D. a second drive shaft extending through the second outer sheath, wherein the second drive shaft is rotatable relative to the second outer sheath,
  wherein the second drive shaft is operable to longitudinally actuate the third jaw and the fourth jaw to grasp the needle; and
(c) a handle assembly coupled to the proximal end of the shaft, the handle assembly comprising a casing and an actuatable control assembly comprising a cam surface and a gear, wherein the actuatable control assembly is configured to linearly actuate the cam surface and the gear unitarily along a linear path, wherein the control assembly is operable to rotate the first drive shaft and the second drive shaft in response to actuation of the control assembly relative to the casing along the linear path, wherein the control assembly is operable to grasp the needle with the second needle grasping member and release the needle from the first needle grasping member when the control assembly is actuated along the linear path.

* * * * *